US011434279B2

(12) United States Patent
Song et al.

(10) Patent No.: US 11,434,279 B2
(45) Date of Patent: Sep. 6, 2022

(54) ANTI-FACTOR D ANTIBODIES AND USES THEREOF

(71) Applicant: The Trustees of the University of Pennsylvania, Philadelphia, PA (US)

(72) Inventors: Wenchao Song, Bryn Mawr, PA (US); Lin Zhou, Bryn Mawr, PA (US); Sayaka Sato, Philadelphia, PA (US); Takashi Miwa, Bala Cynwyd, PA (US); Damodar Gullipalli, Philadelphia, PA (US); Madhu Golla, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 163 days.

(21) Appl. No.: 16/484,962

(22) PCT Filed: Feb. 9, 2018

(86) PCT No.: PCT/US2018/017537
§ 371 (c)(1),
(2) Date: Aug. 9, 2019

(87) PCT Pub. No.: WO2018/148486
PCT Pub. Date: Aug. 16, 2018

(65) Prior Publication Data
US 2019/0359699 A1    Nov. 28, 2019

Related U.S. Application Data

(60) Provisional application No. 62/457,477, filed on Feb. 10, 2017.

(51) Int. Cl.
*C07K 16/18* (2006.01)
*C07K 16/28* (2006.01)
(Continued)

(52) U.S. Cl.
CPC .......... *C07K 16/18* (2013.01); *A01K 67/0278* (2013.01); *A61P 37/06* (2018.01);
(Continued)

(58) Field of Classification Search
None
See application file for complete search history.

(56) References Cited

U.S. PATENT DOCUMENTS 8,124,090 B2    2/2012  Fung
8,273,352 B2    9/2012  Huang
(Continued)

FOREIGN PATENT DOCUMENTS

AU    2013200988 A1    3/2013
AU    2016202258 A1    5/2016
(Continued)

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*
(Continued)

*Primary Examiner* — Aurora M Fontainhas
(74) *Attorney, Agent, or Firm* — Riverside Law LLP

(57) ABSTRACT

This invention relates to selective inhibition of the alternative pathway (AP) of the complement system using an anti-factor D antibody. Specifically, the invention relates to methods of treating an AP-mediated disease or AP-mediated disorder in an individual by contacting the individual with an anti-factor D antibody.

16 Claims, 26 Drawing Sheets

Specification includes a Sequence Listing.

(51) Int. Cl.
*A61P 37/06* (2006.01)
*A01K 67/027* (2006.01)
*A61K 39/00* (2006.01)

(52) U.S. Cl.
CPC .... *A01K 2207/15* (2013.01); *A01K 2217/072* (2013.01); *A01K 2227/105* (2013.01); *A01K 2267/0306* (2013.01); *A61K 2039/505* (2013.01); *A61K 2039/54* (2013.01); *C07K 2317/24* (2013.01); *C07K 2317/34* (2013.01); *C07K 2317/565* (2013.01); *C07K 2317/94* (2013.01)

(56) References Cited

U.S. PATENT DOCUMENTS

| | | |
|---|---|---|
| 8,372,403 B2 | 2/2013 | An |
| 2005/0232920 A1 | 10/2005 | Fung |
| 2006/0105389 A1 | 5/2006 | Kordyum |
| 2009/0041749 A1 | 2/2009 | Dennis |
| 2013/0110249 A1 | 5/2013 | Schwarz |
| 2014/0212433 A1 | 7/2014 | Huang |
| 2015/0030600 A1 | 1/2015 | Marks |
| 2016/0017052 A1 | 1/2016 | Kelley |
| 2016/0031977 A1 | 2/2016 | Lu |
| 2017/0355756 A1* | 12/2017 | Julien .................. A61P 21/02 |

FOREIGN PATENT DOCUMENTS

| | | | |
|---|---|---|---|
| CN | 103483447 | 1/2014 | |
| JP | 2002503706 | 2/2002 | |
| JP | 2013049724 | 3/2013 | |
| JP | 2016145205 | 8/2016 | |
| WO | 2008055206 | 5/2008 | |
| WO | WO-2008068048 A2 * | 6/2008 | ............ C07K 16/14 |
| WO | 2015168468 A1 | 11/2015 | |

OTHER PUBLICATIONS

Kussie et al., A single engineered amino acid substitution changes antibody fine specificity.J Immunol. Jan. 1, 1994;152(1):146-52. (Year: 1994) (Year: 1994).*

Edwards et al., The remarkable flexibility of the human antibody repertoire; isolation of over one thousand different antibodies to a single protein, BLyS. J Mol Biol. Nov. 14, 2003;334(1):103-18. (Year: 2003) (Year: 2003).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

"Uncharacterized protein", UniProtKB, (May 3, 2011), Database accession No. FOVM61_NEOCL [A] 2, 3, (18, 19)/(2, 3) (5 pages).

"Uncharacterized protein", UniProtKB, (Oct. 3, 2012), Database accession No. J2YS19_9ACTO [A] 2, 3, (18, 19)/(2, 3) (2 pages).

International Preliminary Report on Patentability for PCT/US2018/17537 dated Aug. 13, 2019 (7 pages).

International Search Report for PCT/US2018/17537 dated Jun. 21, 2018 (7 pages).

Katschke et al., "Inhibiting Alternative Pathway Complement Activation by Targeting the Factor D Exosite", J. Biol. Chem., 2012, 287:12886-12892.

Kimura et al., "Genetic and therapeutic targeting of properdin in mice prevents complement-mediated tissue injury", J. Clinic. Investig., 2010, 120:3545-3554.

Kimura Y et al., "Activator-specific requirement of properdin in the initiation and amplification of the alternative pathway complement", Blood, 2008, 111:732-740.

Kohler et al., "Continuous cultures of fused cells secreting antibody of predefined specificity", Nature, 1975, 256:495-497.

Miwa T et al., "Crry, but not CD59 and DAF, is indispensable for murine erythrocyte protection in vivo from spontaneous complement attack", Blood, 2002, 99:3707-3716.

Written Opinion of the International Searching Authority for PCT/US2018/17537 dated Jun. 21, 2018 (6 pages).

Egorova A, 2012, "The role of the complement system in the pathogenesis of age-related macular degeneration. Methods of drug exposure (literature review)", Ophthalmologicheskie, 2:77-82.

Rudikoff et al., 1981, "Single Amino Acid Substitution Altering Antigen-binding Specificity", Proc. Natl. Acad. Sci., 79:1979-1983.

Yarlina A., 1999, Osnovy immunologii: Textbook.—M.: Medicine, 608:172-173.

Loyet et al., 2014, "Complement Inhibition in Cynomolgus Monkeys by Anti-Factor D Antigen-Binding Fragment for the Treatment of an Advanced Form of Dry Age-Related Macular Degeneration", The Journal of Pharmacology and Experimental Therapeutics, 351:527-537.

* cited by examiner

```
CTCAAGGTCCTTACAatgaaatgcagctgggtatgtcttcctgatggcagtggttaca
 L  K  V  L  T  M  K  C  S  W  V  I  V  F  L  M  A  V  V  T
gggtcaattcagaggttcagctgcagcagtctggggcagacttgtgaggccagggggcc
 G  V  N  S  E  V  Q  L  Q  Q  S  G  A  D  L  V  R  P  G  A
tcagtcaagttgtcctgcacaacttctggcttcaacattaaagacacctatgtgcactgg      CDR1 (SEQ ID NO: 3)
 S  V  K  L  S  C  T  T  S  G  F  N  I  K  D  T  Y  V  H  W
gtgaaacagaggcctgaacagggcctggaatggattggaaggattgatcctgaatggt       CDR2 (SEQ ID NO: 4)
 V  K  Q  R  P  E  Q  G  L  E  W  I  G  R  I  D  P  A  N  G
cttactacattgatccgaggttccagggccactataacagcagacacatcctcc
 L  Y  Y  I  D  P  R  F  Q  G  K  A  T  I  T  A  D  T  S  S
aatacggctacctgcagtcagcagcctgacatctgaggacactgcggtctattactgt
 N  T  A  Y  L  Q  L  S  S  L  T  S  E  D  T  A  V  Y  Y  C
acatatgctatggaatattgggtcaaggaacctcagtcaccgtctcctcagcaaaacg       CDR3 (SEQ ID NO: 5)
 T  Y  A  M  E  Y  W  G  Q  G  T  S  V  T  V  S  S  A  K  T
acaccccatcctgtctatccactggcccc (SEQ ID NO: 1)
 T  P  P  S  V  Y  P  L  A    (SEQ ID NO: 2)
```

Figure 3A ggaccaagttcaaagacaaaatg gatttcaagtgcagatttcagcttcctgctaatc
 G  P  K  F  K  D  K  M   D  F  Q  V  Q  I  F  S  F  L  L  I
agtgcctcagtcatgctgtcagagga cacaaattgtctctccagtctccagcaatcatg
 S  A  S  V  M  L  S  R  G   Q  I  V  L  T  Q  S  P  A  I  M
tctgcatctccaggggagaggtcacc atgacctgcagtgccagatcagatgtaagttac
 S  A  S  P  G  E  R  V  T   M  T  C  S  A  R  S  D  V  S  Y
atgtattggtatcagcagaagccaga gcctcccccagtctgattatatgacatcc
 M  Y  W  Y  Q  Q  K  P  G   S  S  P  R  L  I  Y  D  T  S
aacctggcttctggagtccctgtt cgcttcagtggcagtgggtctgggacctcttactct
 N  L  A  S  G  V  P  V  R   F  S  A  S  G  S  G  T  S  Y  S
ctcaccatcagccgaatggaggctg aagatgctgccacttactactactgccagcagtggagt
 L  T  I  S  R  M  E  A  E   D  A  A  T  Y  Y  C  Q  Q  W  S
agttaccccacggtcggacgttcg gtggaggcaccaagctggaaatcaaacgggctgatgct
 S  Y  P  T  F  G  G  G  T   K  L  E  I  K  R  A  D  A
gcaccaac (SEQ ID NO: 6)
 A  P  (SEQ ID NO: 7)

CDR1 (SEQ ID NO: 8)
CDR2 (SEQ ID NO: 9)
CDR3 (SEQ ID NO: 10)

Figure 3B

```
gccCAAGTCTTAGACATCatggattggctgtgtggaacttgctgtattcctgatggcagctgcc
 A  Q  V  L  D  I  M  D  W  L  C  V  E  L  A  V  F  L  M  A  A  A
caaagtgcccaagatccagagcacagatccagtcgtgtcagtctgacctgagctgaagaagctgga
 Q  S  A  Q  I  Q  L  V  Q  S  G  P  E  L  K  K  P  G
gagacagtcaagatctcctgcaaggcttctggatacctcacaaacttgaatgaac
 E  T  V  K  I  S  C  K  A  S  G  Y  T  F  T  N  F  E  N
tgggtgaagcaggctccaggacagggtctaaactgatggctataaacactacact
 W  V  K  Q  A  P  G  Q  G  L  N  W  M  G  C  I  N  T  Y  T
ggagacccaatatgctgactgcagatcacctcttctgtgaacctct
 G  D  P  Y  A  D  F  R  G  R  F  A  F  S  L  E  T  S
gcccactgcctattgcagatcacacctcaaatgaggacatggctacatattt
 A  S  T  A  Y  L  Q  I  N  N  L  K  N  E  D  M  A  T  Y  F
tgttcaagagaggaggggggactactgggccaggcaccactcacgtctcctca
 C  S  R  E  G  G  D  Y  W  G  Q  G  T  T  L  T  V  S  S
gccaaacgac (SEQ ID NO: 11)
 A  K  T       (SEQ ID NO: 12)
```

CDR1  (SEQ ID NO: 13)
CDR2  (SEQ ID NO: 14)
CDR3  (SEQ ID NO: 15)

Figure 4A ggaaatacatcaggcaggcaagggcatcaagatgaagtcacagacccagtctctgtattt
                              M  K  S  Q  T  Q  V  F  V  F
ctactgctcctctgtgtcttggtgtcatggagtattgtgatgaccagactcccaaattc
 L  L  L  L  C  V  G  A  H  G  S  I  V  M  T  Q  T  P  K  F
ctgcttgtatcagcaggagacagggtaccataacctgcaaggccagtcagagtgtgact
 L  L  V  S  A  G  D  R  V  T  I  T  C  K  A  S  Q  S  V  T
aatgatgtagcttggtaccaacagaagccaggacagtctcctagattgctgatataccat
 N  D  V  A  W  Y  Q  Q  K  P  G  Q  S  P  R  L  L  I  Y  H
gcatccaatcgctacactggagtccctgagcgtttcactggcagtggatatggacggat
 A  S  N  R  Y  T  G  V  P  E  R  F  T  G  S  G  Y  G  D
ttcactttcaccatcaacactgtgcaggctgaagacctggcagttatttctgtcagcag
 F  T  F  T  I  N  T  V  Q  A  E  D  L  A  V  Y  F  C  Q  Q
gattatagctctcctcggacgttcggtggaggcaccaagctggaaatcaaacgggctgat
 D  Y  S  S  P  R  T  F  G  G  G  T  K  L  E  I  K  R  A  D
gctgccaac  (SEQ ID NO: 16)
 A  A  N   (SEQ ID NO: 17)

CDR1 (SEQ ID NO: 18)
CDR2 (SEQ ID NO: 19)
CDR3 (SEQ ID NO: 20)

Figure 4B

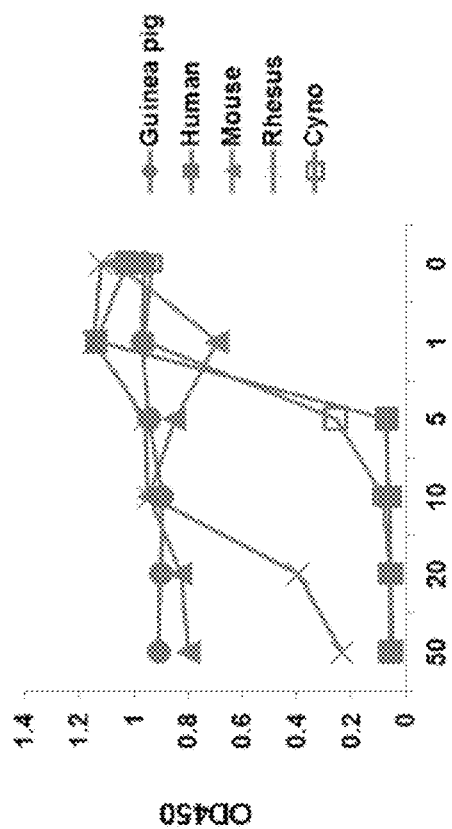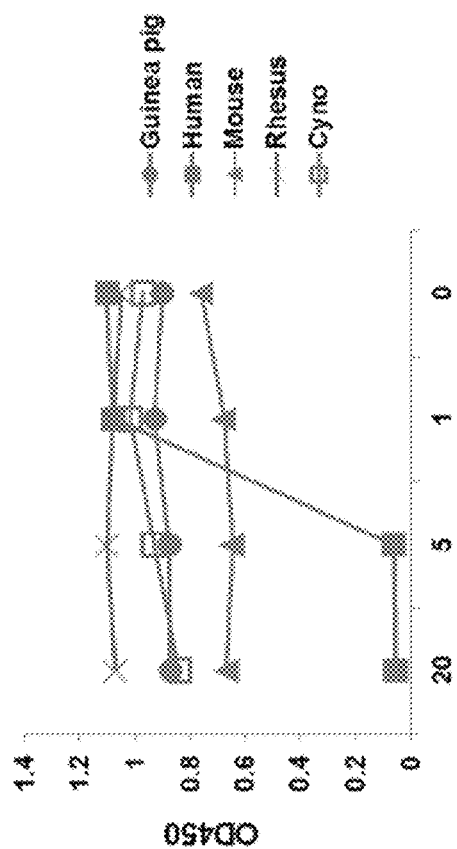
Figure 5

A

ILGGREAEAHARPYMASVQLNGAHLCGGVLVAEQWVLSAAHCLEDAADGKVQVLLG
AHSLSQPEPSKRLYDVLRAVPHPDSQPDTIDHDLLLQLSEKATLGPAVRPLPWQRVDR (SEQ ID NO: 21)
DVAPGTLCJDVAGWGIVNHAGRRPDSLQHVLLPVLDRATCNRRTHHDXGATTERLMCAES (SEQ ID NO: 22)
NRRDSCKGDSGGPLVCGGVLEGVVTSGSRVCGNRKKPGIYTRVASYAAWIDSVLA

Figure 11B

A  ILGGREAEAHARPYMASVQLNGAHLCGGVLVAEQWVLSAAHCLEDAADGKVQVLLG
AHSLSQPEPSKRLYDVLRAVPHPDSQPDTIDHDLLLQLSEKATLGPAVRPLPWQRVDR
DVAPGTLCDVAGWGIVNHAGRRPDSLQHVLLPVLDRATCNRRTHDGAITERLMCAES
NRRDSCKGDSGGPLVCGGVLEGVVTSGSRVCGNRKKPGIYTRVASYAAWIDSVLA
(SEQ ID NO: 23)   (SEQ ID NO: 24)
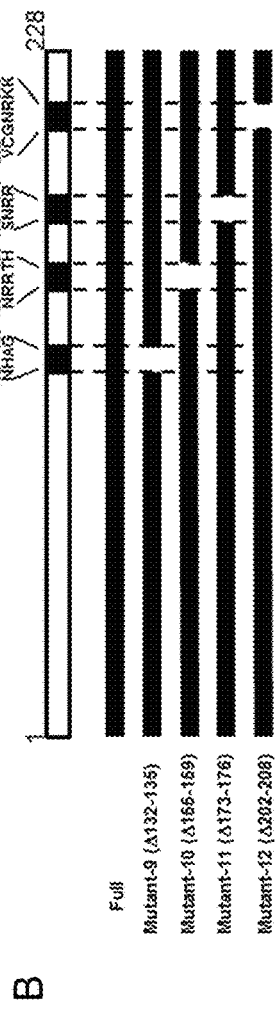
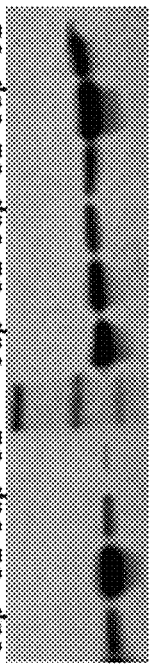
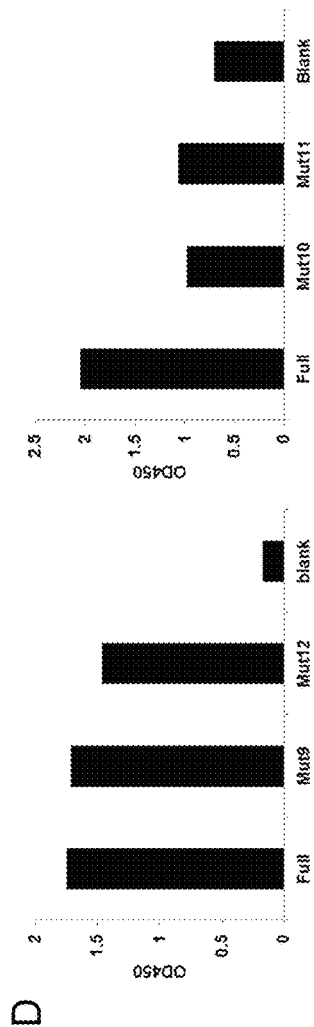
Figure 19

ANTI-FACTOR D ANTIBODIES AND USES THEREOF

CROSS-REFERENCE TO RELATED APPLICATION

This application is a U.S. national phase application filed under 35 U.S.C. § 371 claiming benefit to International Patent Application No. PCT/US2018/017537, filed Feb. 9, 2018, which is entitled to priority under 35 U.S.C. § 119(e) to U.S. Provisional Patent Application No. 62/457,477, filed Feb. 10, 2017, each of which applications is hereby incorporated herein by reference in its entirety.

STATEMENT REGARDING FEDERALLY SPONSORED RESEARCH OR DEVELOPMENT

This invention was made with government support under NIH AI085596 and NIH AI117410 awarded by the National Institutes of Health (NIH). The government has certain rights in the invention.

BACKGROUND OF THE INVENTION

The complement system provides a first line of host defense against invading pathogens. Complement also plays a pathogenic role in human inflammatory diseases. Activation of the complement system occurs via three different pathways, the classical pathway (CP), the lectin pathway (LP) and the alternative pathway (AP). The CP is initiated by antigen-antibody binding. The LP is triggered when mannose-binding lectins (MBL) interact with surface sugar molecules on microorganisms. Activation of both pathways leads to the assembly of the CP C3 convertase C4b2a, although direct cleavage of C3 by MBL-associated serine proteases can also occur. The AP is a self-amplification loop driven by the AP C3 convertase, C3bBb. AP activation can occur secondary to CP or LP activation, or is initiated independently. In the latter case, a low level spontaneous C3 'tick-over' generates the initial C3bBb, which rapidly propagates the AP in the absence of adequate regulation. Thus, it is generally assumed that AP activation on non-self surfaces with no or insufficient negative regulation is considered a default process, whereas autologous cells typically avoid this outcome with the help of multiple membrane-bound and fluid phase complement inhibitory proteins. Under certain conditions, altered, damaged or stressed autologous cells and tissues can also activate AP and cause inflammatory injury.

Factor D (FD) is an essential enzyme for AP complement activation. It cleaves factor B after the latter is bound to C3b to produce an active C3 convertase, C3bBb. Factor D is a serine protease of approximately 24 kDa in size and it circulates in the blood as a constitutively active enzyme after being generated from pro-factor D by enzymatic action of mannose binding lectin-associated serine protease-3 (MASP-3). Compared with other complement proteins in blood, the concentration of factor D in blood is rather low (approximately 2 µg/ml). While the latter fact may suggest that therapeutic inhibition of factor D activity in blood is possible and might be easily achieved, previous studies have shown that factor D has a fast turnover, and accordingly the consensus in the complement research field is that it would not be feasible to block factor D systemically. There is a need in the field for anti-human factor D mAbs that can inhibit AP complement activity systemically and thereby treat AP complement-dependent pathologies, and there is a need in the field for appropriate animal models to test and validate such anti-human factor D mAbs. The present invention addresses and meets these and other needs.

SUMMARY

This invention relates to anti-factor D antibodies and methods of inhibiting the alternative pathway (AP) of complement using an anti-factor D antibody.

In one embodiment, the invention is a composition comprising antibodies that specifically binds to factor D. In some embodiments, the factor D is human factor D. In some embodiments, the antibodies of the invention are monoclonal antibodies. In some embodiments, the antibodies of the invention are humanized antibodies. In some embodiments, the antibody of the invention is a chimeric antibody. In some embodiments, the antibody is a full-length antibody. In some embodiments, the antibody is an antibody fragment, which includes, but is not limited to, Fab, Fab', F(ab)2, F(ab')2, and scFv. In some embodiments, the antibody is part of a construct, for example a fusion construct comprising the antibody and a targeting moiety or an effector moiety. In some embodiments, the antibody is part of a conjugate construct, such as an antibody drug conjugate construct.

In one embodiment, an antibody of the invention comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, an antibody of the invention comprises a heavy chain comprising the amino acid sequence of SEQ ID NO:2, or a variant thereof. In one embodiment, an antibody of the invention comprises a light chain comprising the amino acid sequence of SEQ ID NO:7, or a variant thereof. In another embodiment, an antibody of the invention comprises a heavy chain comprising the amino acid sequence of SEQ ID NO:2 and a light chain comprising the amino acid sequence of SEQ ID NO:7, or a variant or variants thereof.

In one embodiment, the antibody of the invention comprises at least one of the CDRs selected from the group consisting of: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20, or a variant or variants thereof. In another embodiment, the antibody of the invention is an antibody that comprises a heavy chain comprising the amino acid sequence of SEQ ID NO:12, or a variant thereof. In one embodiment, the antibody of the invention comprises a light chain comprising the amino acid sequence of SEQ ID NO:17, or a variant thereof. In another embodiment, the antibody of the invention is an antibody that comprises a heavy chain comprising the amino acid sequence of SEQ ID NO:12 and a light chain comprising the amino acid sequence of SEQ ID NO:17, or a variant or variants thereof.

In one embodiment, the antibody of the invention is mAb 11-8A1 or mAb 1F10-5. In one embodiment, the antibody of the invention is an antibody that binds to factor D and competes with the binding of at least one other anti-factor D antibody. In one embodiment, the antibody of the invention is an antibody that binds to factor D and competes with the binding of at least one of the anti-factor D antibodies described herein. In another embodiment, the antibody of the invention is an antibody that binds to factor D and competes with the binding of the antibody designated mAb 11-8A1 to factor D. In another embodiment, the antibody of the invention is an antibody that binds to factor D and competes with the binding of the antibody designated mAb 1F10-5 to factor D.

In another embodiment, the invention is a method of treating an alternative pathway (AP)-mediated disease or disorder in an individual, comprising the step of administering to said individual at least one anti-factor D antibody. In various embodiments, the alternative pathway (AP)-mediated disease or disorder is at least selected from the group consisting of: macular degeneration (MD), age-related macular degeneration (AMD), ischemia reperfusion injury, arthritis, rheumatoid arthritis, asthma, allergic asthma, paroxysmal nocturnal hemoglobinuria (PNH) syndrome, atypical hemolytic uremic (aHUS) syndrome, epidermolysis bullosa, sepsis, organ transplantation, inflammation (including, but not limited to, inflammation associated with cardiopulmonary bypass surgery and kidney dialysis), C3 glomerulopathy, membranous nephropathy, glomerulonephritis (including, but not limited to, anti-neutrophil cytoplasmic antibody (ANCA)-mediated glomerulonephritis, lupus, and combinations thereof), ANCA-mediated vasculitis, Shiga toxin induced HUS, and antiphospholipid antibody-induced pregnancy loss, and combinations thereof. In some embodiments, the anti-factor D antibody inhibits the alternative pathway, but does not inhibit the activation of the classical pathway and the lectin pathway. In some embodiments, the anti-factor D antibody inhibits the generation of a C3bBb protein. In some embodiments, the anti-factor D antibody inhibits AP contributions to downstream complement signaling. In some embodiments, the AP-mediated disease is C3 glomerulopathy. In some embodiments, the AP-mediated disease is macular degeneration, such as age-related macular degeneration.

In one embodiment, the invention is a method of reducing the activity of an alternative pathway of a complement system of an individual, comprising administering an antibody to the individual via a route of administration including enteral administration, parenteral administration, and a combination thereof, and wherein the antibody comprises six complementarity determining regions having the following amino acid sequences: SEQ ID NO: 3, SEQ ID NO: 4, SEQ ID NO: 5, SEQ ID NO: 8, SEQ ID NO: 9, and SEQ ID NO: 10, or a variant or variants thereof. In another embodiment, the antibody is an antibody fragment selected from the group consisting of a Fab, Fab', F(ab)2, F(ab')2, scFv, and combinations thereof.

In one embodiment, the invention is a method of reducing the activity of an alternative pathway of a complement system of an individual comprising administering an antibody to the individual via a route of administration including enteral administration, parenteral administration, and a combination thereof, and wherein the antibody comprises six complementarity determining regions having the following amino acid sequences: SEQ ID NO: 13, SEQ ID NO: 14, SEQ ID NO: 15, SEQ ID NO: 18, SEQ ID NO: 19, and SEQ ID NO: 20, or a variant or variants thereof. In another embodiment, the antibody is an antibody fragment including a Fab, Fab', F(ab)2, F(ab')2, scFv, and combinations thereof.

In one embodiment, the invention is an isolated antibody that binds to human factor D, the antibody alternatively binds to either one of a first epitope and a second epitope of factor D, both the first epitope and the second epitope have portions that assume a coil conformation in their secondary structure, and wherein a portion of factor D that assumes a beta-strand conformation in its secondary structure is between the first epitope and the second epitope. In another embodiment, the first epitope has an amino acid sequence that comprises SEQ ID NO: 21 and the second epitope has an amino acid sequence that comprises SEQ ID NO: 22. In another embodiment the first epitope has an amino acid sequence that comprises SEQ ID NO: 23 and the second epitope has an amino acid sequence that comprises SEQ ID NO: 24. In another embodiment, the antibody is an antibody fragment selected from the group consisting of a Fab, Fab', F(ab)2, F(ab')2, scFv, and combinations thereof. In another embodiment, the antibody binds to an epitope of factor D, and wherein the epitope has an amino acid sequence that comprises SEQ ID NO: 21. In another embodiment, the antibody is an antibody fragment selected from the group consisting of a Fab, Fab', F(ab)2, F(ab')2, scFv, and combinations thereof.

In one embodiment, the invention is an isolated antibody that binds to human factor D, wherein the antibody binds to an epitope of factor D, and wherein the epitope has an amino acid sequence that comprises SEQ ID NO: 22. In another embodiment, the antibody is an antibody fragment selected from the group consisting of a Fab, Fab', F(ab)2, F(ab')2, scFv, and combinations thereof.

In one embodiment, the invention is an isolated antibody that binds to human factor D, wherein the antibody binds to an epitope of factor D, and wherein the epitope has an amino acid sequence that comprises SEQ ID NO: 23. In another embodiment, the antibody is an antibody fragment selected from the group consisting of a Fab, Fab', F(ab)2, F(ab')2, scFv, and combinations thereof.

In one embodiment, the invention is an isolated antibody that binds to human factor D, wherein the antibody alternatively binds to either one of a first epitope and a second epitope of factor D, wherein the first epitope has an amino acid sequence that comprises SEQ ID NO: 21, and wherein the second epitope has an amino acid sequence that comprises SEQ ID NO: 22. In another embodiment, the antibody consists of a Fab, Fab', F(ab)2, F(ab')2, scFv, and combinations thereof.

In one embodiment, the invention is an isolated polypeptide that binds to human factor D, wherein the polypeptide binds to an epitope of factor D, the epitope has an amino acid sequence that comprises SEQ ID NO: 21, or SEQ ID NO: 22 and the polypeptide includes at least one amino acid sequence selected from the group consisting of SEQ ID NO: 3, SEQ ID NO: 4, SEQ ID NO: 5, SEQ ID NO: 8, SEQ ID NO: 9, and SEQ ID NO: 10, or a variant or variants thereof.

In one embodiment, the invention is an isolated polypeptide that binds to human factor D, wherein the polypeptide binds to an epitope of factor D, the epitope has an amino acid sequence that comprises SEQ ID NO: 24, and the polypeptide comprises at least one amino acid sequence selected from the group consisting of SEQ ID NO: 13, SEQ ID NO: 14, SEQ ID NO: 15, SEQ ID NO: 18, SEQ ID NO: 19, and SEQ ID NO: 20, or a variant or variants thereof.

In one embodiment, the invention is an antibody against human factor D, wherein the antibody has a heavy chain variable (vH) region that has an amino acid sequence that is more than 90% (such as more than any of 91%, 92%, 93%, 94%, 95%, 96%, 97%, 98%, or 99%) identical to SEQ ID NO: 2. In another embodiment, the antibody is an antibody fragment selected from the group consisting of a Fab, Fab', F(ab)2, F(ab')2, scFv, and combinations thereof.

In one embodiment, the invention is an antibody against human factor D, wherein the antibody has a light chain variable (vL) region that has an amino acid sequence that is more than 90% (such as more than any of 91%, 92%, 93%, 94%, 95%, 96%, 97%, 98%, or 99%) identical to SEQ ID NO: 7. In another embodiment, the antibody is an antibody fragment selected from the group consisting of a Fab, Fab', F(ab)2, F(ab')2, scFv, and combinations thereof.

In one embodiment, the invention is an antibody against human factor D, wherein the antibody has a heavy chain variable (vH) region and a light chain variable (vL) region, wherein the vH region has an amino acid sequence that is more than 90% (such as more than any of 91%, 92%, 93%, 94%, 95%, 96%, 97%, 98%, or 99%) identical to SEQ ID NO: 2, and wherein the vL region has an amino acid sequence that is more than 90% (such as more than any of 91%, 92%, 93%, 94%, 95%, 96%, 97%, 98%, or 99%) identical to SEQ ID NO: 7. In another embodiment, the antibody is an antibody fragment selected from the group consisting of a Fab, Fab', F(ab)2, F(ab')2, scFv, and combinations thereof.

In one embodiment, the invention is a cell that produces an antibody, wherein the antibody targets factor D. In one embodiment, the cell is a hybridoma. In another embodiment, the cell is a cell line.

In another embodiment, the invention is a genetically modified non-human animal that expresses human factor D. In some embodiments, the non-human animal is a rodent, such as a rat or a mouse. In one embodiment, the invention is a genetically modified mouse that expresses human factor D. In one embodiment, the invention is a genetically modified mouse that expresses human factor D, but does not express murine factor D. In another embodiment, the invention is a genetically modified mouse that expresses human factor D from the mouse regulatory elements, but does not express murine factor D.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings. In the drawings:

FIG. 3 depicts the nucleotide and amino acid sequence of the variable region sequences of heavy (SEQ ID NO:1; SEQ ID NO:2) and light (SEQ ID NO:6; SEQ ID NO:7) chains of mAb 11-8A1, including the CDRs (VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; VL-CDR3: SEQ ID NO:10) of mAb 11-8A1.

FIG. 4 depicts the nucleotide and amino acid sequence of the variable region sequences of heavy (SEQ ID NO:11; SEQ ID NO:12) and light (SEQ ID NO:16; SEQ ID NO:17) chains of mAb 1F10-5, including the CDRs (VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; VL-CDR3: SEQ ID NO:20) of mAb 1F10-5.

FIG. 5 depicts the results of experiments assessing the relative activities of 11-8A1 and 1F10-5 mAbs in blocking LPS-induced human, monkey, guinea pig and mouse AP complement activation. The ability of mAbs 11A8-1 and 1F10-5 to inhibit alternative pathway activity in sera from different mammalian species was tested using LPS-AP assay. ELISA plates were coated with LPS, 37° C., 1 hour, and 50% normal human, monkey, guinea pig or mouse serum diluted in GVB-Mg++-EGTA was added and incubated at 37 C for 1 hour before detection of C3 deposition using anti-human C3 antibodies or anti-mouse C3 antibodies. For 11-8A1 mAb, concentrations of 5-20 µg/ml were sufficient to inhibit human AP complement activation whereas 11-8A1 mAb was not able to inhibit mouse, guinea pig, monkey (Rhesus and cynomolgus) AP complement activation. For 1F10-5 mAb, concentrations of 5-20 µg/ml were sufficient to inhibit human AP complement activation whereas 1F10-5 mAb was not able to inhibit mouse and guinea pig AP complement activation. 1F10-5 mAb at 10 or 20 µg/ml was effective at inhibiting Cynomolgus monkey AP complement activation. On the other hand, 50 µg/ml of 1F10-5 mAb resulted in a partial inhibition of Rhesus monkey AP complement activation.

FIG. 9, comprising (FIG. 9A) The displayed sequence (228 amino acids) is a mature form of human factor D without propeptide. Amino acids 107-110 (SEQ ID NO: 21), 130-134, 148-151 (SEQ ID NO: 22) and 178-184 are underlined. (FIG. 9B) Schematic diagram of intact and 9 deletion mutants of human factor D for epitope mapping. These proteins were expressed in CHO cells. (FIG. 9C) Confirmation of protein expression. Recombinant intact and deletion mutants of human factor D from either supernatant (Sup) or cell lysate (CL) of CHO cells were immunoblotted with goat anti-human factor D antibodies. + and − indicate positive and negative detection, respectively. (FIG. 9D) Reactivity of mAb 11-8A1 to full and deletion mutant proteins was evaluated by Western-blotting (WB) with goat anti-human factor D polyclonal antibody following immunoprecipitation (IP) with 11-8A1 mAb. + and − indicate positive and negative detection, respectively. NT; not tested.

To map regions or sites in human factor D that are critical for mAb binding, we tested mAb 11-8A1 for reactivity with a series of deletion mutants in full-length (Full) human factor D. Western-blotting using a polyclonal goat anti-human factor D antibody confirmed the expression of most of the deletion mutants at the expected molecular weight. However, several attempts had failed to produce recombinant proteins of deletion-6 and 9. As shown in FIG. 9, mAb 11-8A1 recognized Full, deletion-2 and 4, but did not recognize deletion-1, 3, 5, 7 and 8. These results suggested that deletion of four amino acids of PLPW at 107-110 (SEQ ID NO: 21) or VLDR at 148-151 (SEQ ID NO: 22) disrupted binding by mAb 11-8A1.

FIG. 11, comprising FIGS. 11A through 11D, depicts an outline of the generation of human factor D knock-in mice. (FIG. 11A) Schematic diagrams representing the human factor D targeting construct, the mouse factor D gene locus, the targeted allele, and the neo-deleted allele (from top to bottom). The human factor D cDNA encodes the entire protein of 253-amino acids including signal peptide, propeptide and mature peptide. The dashed lines represent integration sites of the human factor D cDNA in the mouse factor D gene. The position of the probe for ES cells screening is indicated below the diagrams. Abbreviations: restriction sites BamHI (B), HindIII (H), NotI (N) and XhoI (X). FRT, flippase recognition target. LoxP, locus of crossover in P1. (FIG. 11B) The coding sequence of human factor D is flanked by 5' and 3' noncoding sequence of mouse factor D in the targeting construct. Nucleic acid sequence of human factor D is underlined (SEQ ID NO: 25) and restriction enzyme XhoI site is bolded, and nucleic acid sequence of the 5' and 3' untranslated region of mouse factor D is shown in uppercase and lowercase letters, respectively. (FIG. 11C) Southern blotting data showing the positive ES cell clone produced two BamHI restriction fragments (5 kb and 4.5 k b), whereas a representative non-targeted ES cell clone produced only the 5 kb band. (FIG. 11D) PCR genotyping of wild-type (WT), heterozygous (Het) and homozygous (Homo) human factor D knock-in mice using specific to human factor D (target size: 450 bp) 5'-GTC AGG GTG CCA TGC AGG AG-3' (SEQ IN NO:26) and 5'-CCC AGG AGA ACC TGC ACC TTC-3' (SEQ IN NO:27), and specific to mouse factor D (target size: 292 bp) 5'-CCTCCCACCCT-TAGCTATCC-3' (SEQ IN NO:28) and 5'-ACCCA-GACTGTGTCCCTCAC-3' (SEQ IN NO:29).

FIG. 12, comprising (FIG. 12A) By western-blotting using anti-human factor D polyclonal antibodies, a 24 kDa protein band representing human factor D was detected in normal human serum (NHS) as well as in heterozygous and homozygous human factor D knock-in (HDKI) mice, whereas an approximately 40-45 kDa band representing mouse factor D was detected in wild-type (−/−) and heterozygous HDKI mouse sera. (FIG. 12B) Human factor D protein expression could be confirmed by Sandwich ELISA in homozygous HDKI mice. Plate was coated with a polyclonal antibody against human factor D (R&D, AF1824). After incubation with diluted serum (1/2 or 1/5), human factor D was detected by using biotin-conjugated goat-anti-human factor D antibody following HRP-conjugated streptavidin. As expected, human factor D was detected in NHS, recombinant human factor D control wells and in the sera of homozygous human factor D knock-in but not wild-type mice.

FIGS. 17A and 17B, depicts results from experiments assessing the therapeutic efficacy of mAb 11-8A1 in preventing K/B×N mouse IgG-induced arthritis. (FIG. 17A). Susceptibility of homozygous human factor D knock-in (HDKI) mice to K/B×N arthritis. In this model, serum or purified IgG from arthritic K/B×N mice is adoptively transferred to C57BL/6 mice to induce arthritis in a highly reproducible fashion. The disease shows many hall marks of human rheumatoid arthritis including ankle thickening, swelling and progressive joint destruction. As shown in panel A, like wild-type C57BL/6 mice, HDKI mice were also susceptible to K/B×N arthritis as evidenced by an increase in ankle thickness and clinical score after receiving adoptively transferred K/B×N mouse IgG. This data confirmed that human factor D was fully functional in mice in a AP complement-mediated disease setting. (FIG. 17B). Therapeutic efficacy of mAb 11-8A1 for K/B×N arthritis in HDKI mice. Administration of mAb 11-8A1 (1 mg/mouse, every 4 days starting before K/B×N mouse IgG transfer) significantly ameliorated arthritis as indicated by reduced ankle thickness and clinical score compared with mice treated with a control mAb (MOPC). These results demonstrated that it is feasible to ameliorate local complement injury by systemically targeting factor D.

FIG. 19, comprising FIG. 19A through FIG. 19D, depicts epitope mapping for mAb 1F10-5 using deletion constructs. FIG. 19A highlights amino acids 132-135, 155-159 (SEQ ID NO: 23), 173-176 (SEQ ID NO: 24) and 202-208 in mature sequence of human factor D. FIG. 19B depicts a schematic diagram of four deletion mutants of human factor D for epitope mapping. These proteins were produced by mammalian cells. FIG. 19C depicts results confirming protein expression. Supernatant (Sup) and cell lysate (CL) of full and deletion mutants were immunoblotted with goat anti-human factor D antibodies. FIG. 19D depicts reactivity of mAb 1F10-5 to full and deletion mutant proteins was evaluated by ELISA. These results suggested that deletion of amino acids of NRRTH at 155-159 (SEQ ID NO: 23) or SNRR at 173-176 (SEQ ID NO: 24) disrupted binding by mAb 1F10-5.

DETAILED DESCRIPTION OF THE INVENTION

Figure 1:
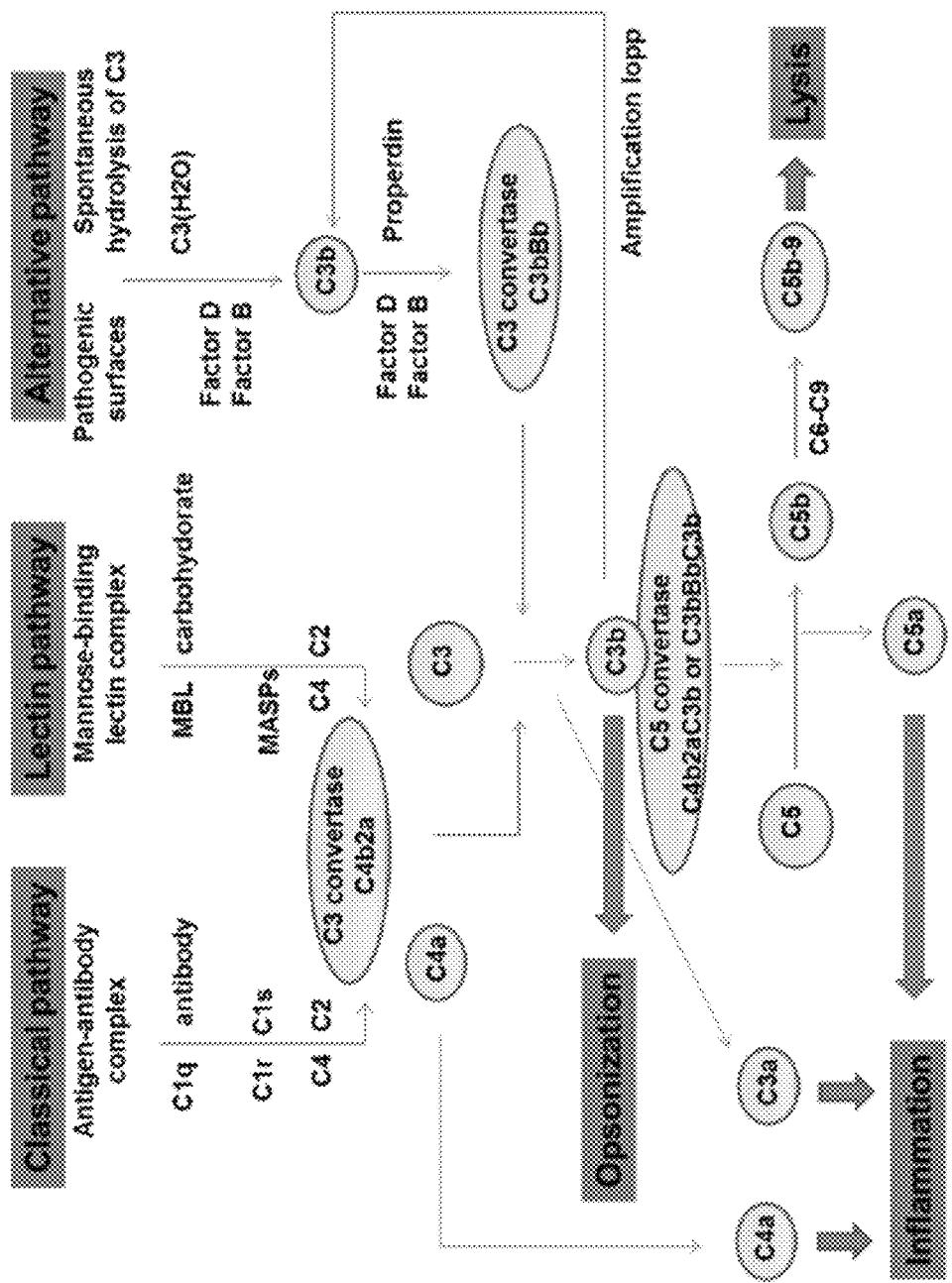
FIG. 1 is a schematic of the complement pathways. The complement system can be activated via three different pathways depending on the initiating stimulus: the classical pathway (CP), lectin pathway (LP) and the alternative pathway (AP) (FIG. 1). The CP is activated primarily by immune complexes composed of antigen and specific antibody. Binding of C1q to antibody attached to antigen, which activates C1r and C1s. Activated C1s cleave C4 and C2. The LP is activated when mannose-binding lectin (MBL) binds to the mannose groups of microbial carbohydrates, activating the MBL-associated serine proteases (MASPs) and again cleaving C4 and C2. C4 and C2 cleavage products form the CP and LP C3 convertase, C4bC2a which cleaves C3 into C3b and C3a. A second molecule of C3b can associate with C4bC2a to form the C5 convertase of the CP and LP. The AP is activated when C3 undergoes spontaneous hydrolysis and forms the initial AP C3 convertase, C3(H2O)Bb, in the presence of Factors B and D, leading to additional C3 cleavage and the eventual formation of the AP C3 convertase (C3bBb) and AP C5 convertase (C3bBbC3b). Properdin facilitates AP activation by stabilizing the AP convertases. All three pathways culminate in the formation of the convertases, which in turn generate the major effectors of the complement system: the anaphylatoxins (C4a/C3a/C5a), the membrane attack complex (MAC), and the opsonins (e.g. C3b). The anaphylatoxins are potent proinflammatory molecules, and are generated through cleavage of C4, C3, and C5, respectively. C5b forms a complex by the consecutive binding of proteins C6-C9, culminating in the formation of the MAC (C5b-9) which can directly lyse targeted surfaces. C3b induces phagocytosis of opsonized targets and also serves to amplify complement activation through the AP.
Figure 2:
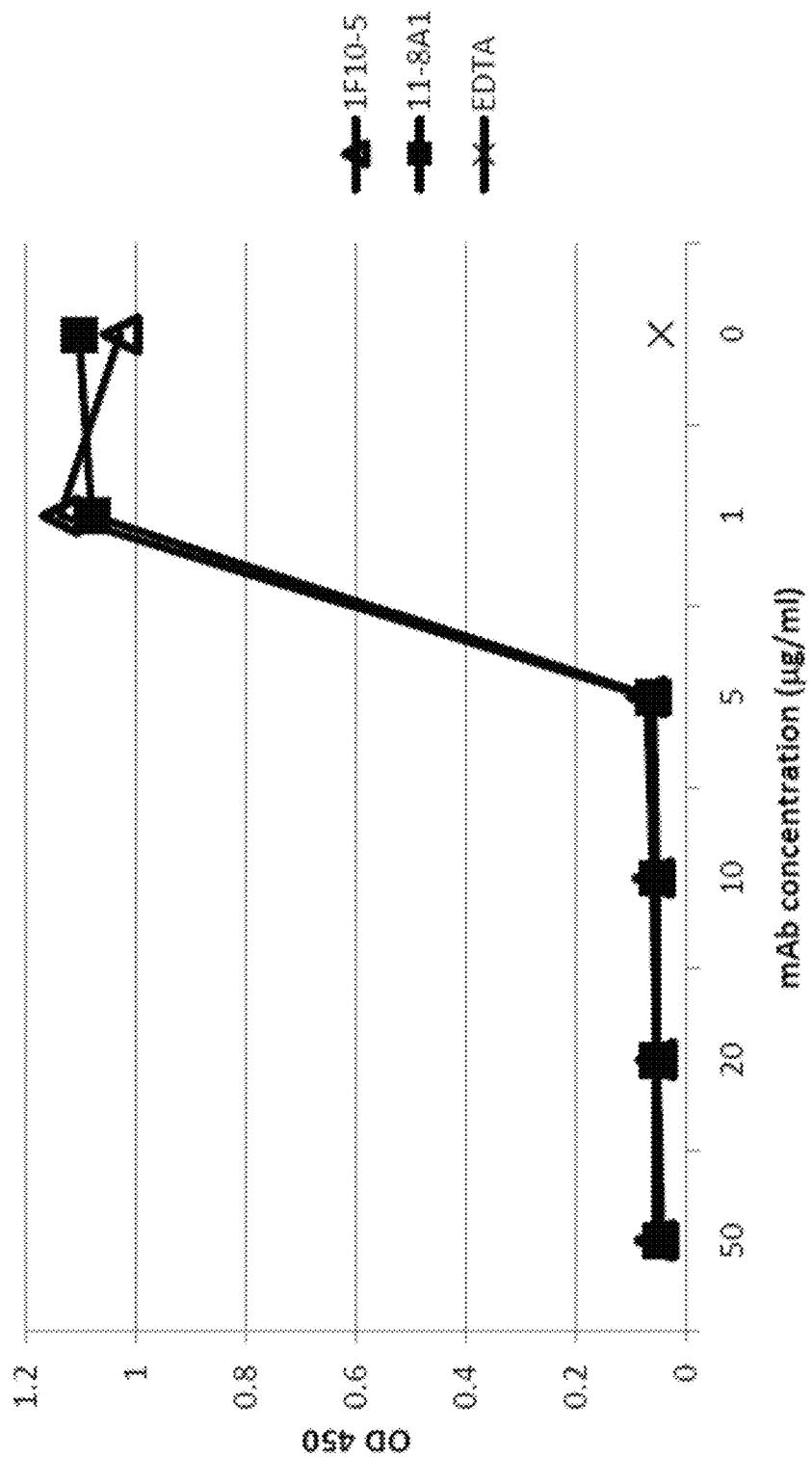
FIG. 2 depicts the results of experiments demonstrating dose-dependent inhibition of LPS-induced AP complement activation by anti-human factor D mAb 11-8A1 and 1F10-5. Both mAbs effectively inhibited AP complement activation when added to 50% normal human serum (NHS) at a final concentration of 5 µg/ml or higher. A sample with EDTA added served as a negative control (EDTA blocks complement activation). A sample with no mAb added (0 Ab) served as the baseline AP complement activation. Experiment was performed in GVB-EGTA-Mg++ buffer. ELISA plates were coated with LPS, 37° C., 1 hour. NHS was preincubated with mAb before addition to plate. AP complement activation was detected by measuring the amount of C3 deposition on the plate (OD450).
Figure 6:
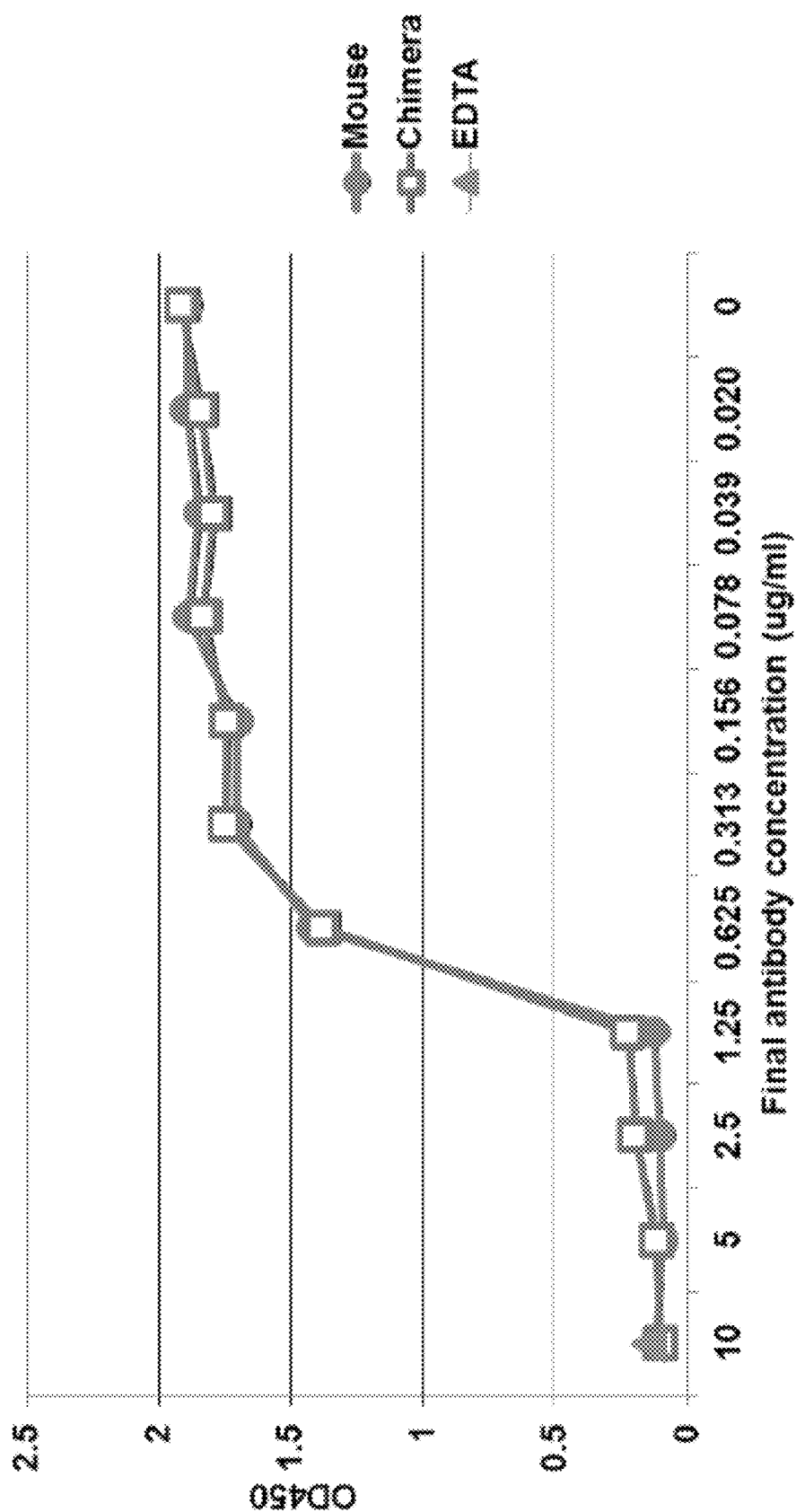
FIG. 6 depicts the results of an experiment comparing the activity of hybridoma-derived murine 11-8A1 and recombinant chimeric 11-8A1 (variable region of 11-8A1+constant region of human IgG4) in blocking LPS-induced human AP complement activation. ELISA plates were coated with LPS, 37° C., 1 hour, and 50% normal human serum (NHS) diluted in GVB-Mg++-EGTA was added and incubated at 37° C. for 1 hour before detection of C3 deposition using anti-human C3 antibodies. NHS with EDTA added was used as a negative control (EDTA). At concentrations of 1.25-10 µg/ml, both forms of 11-8A1 mAb were sufficient to inhibit human AP complement activation and no difference in activity was seen.
Figure 7:
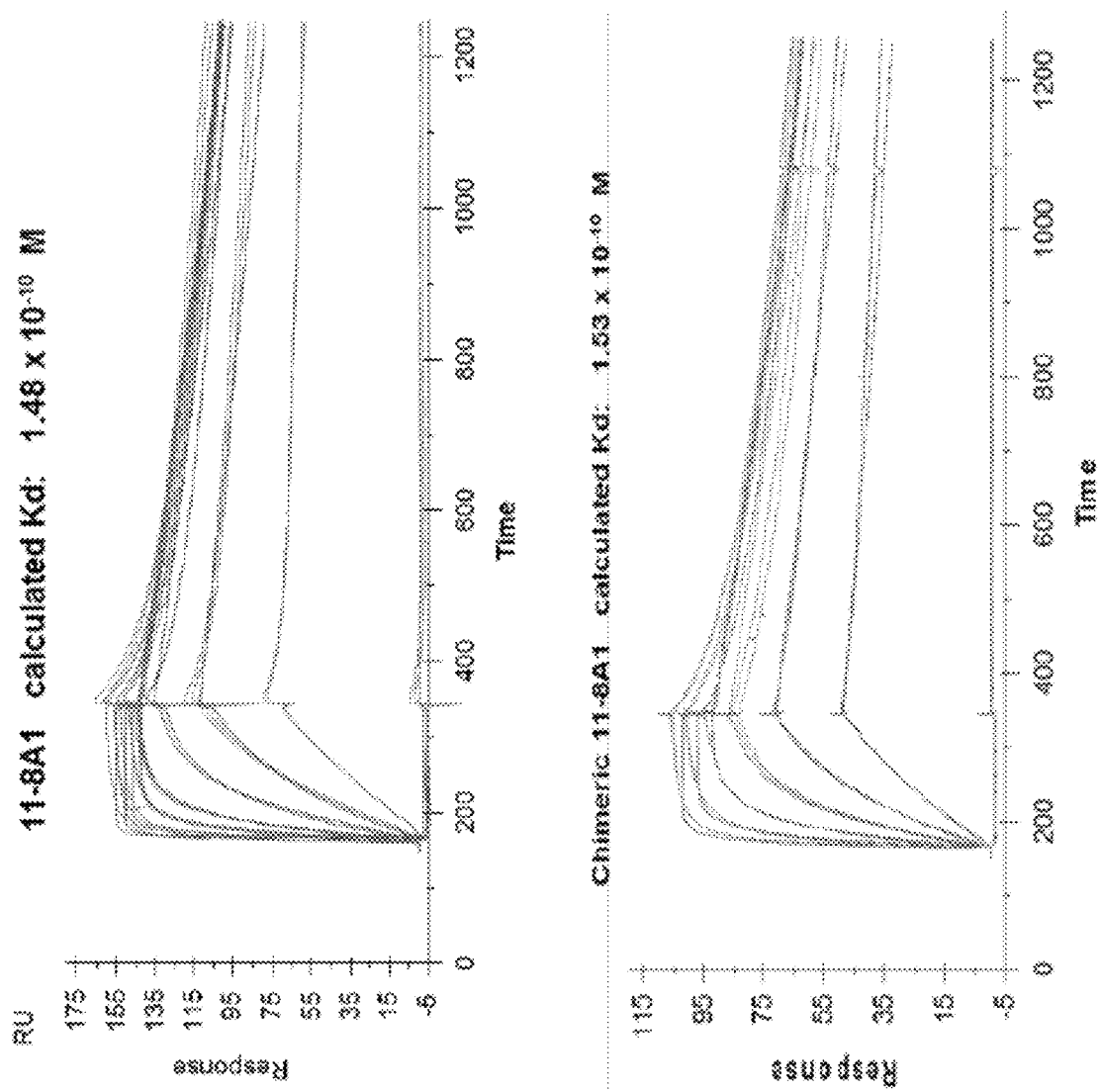
FIG. 7 depicts the results of experiments comparing the antigen binding affinities of hybridoma-derived murine 11-8A1 and recombinant chimeric 11-8A1 mAbs using Biacore. Purified human factor D was coupled onto CM4 chip using the amine coupling method. Biacore analysis was performed on a Biacore-2000 instrument. The chip was regenerated between each binding using 50 mM NaOH. The two forms of 11-8A1 mAbs showed similar affinity.
Figure 8:
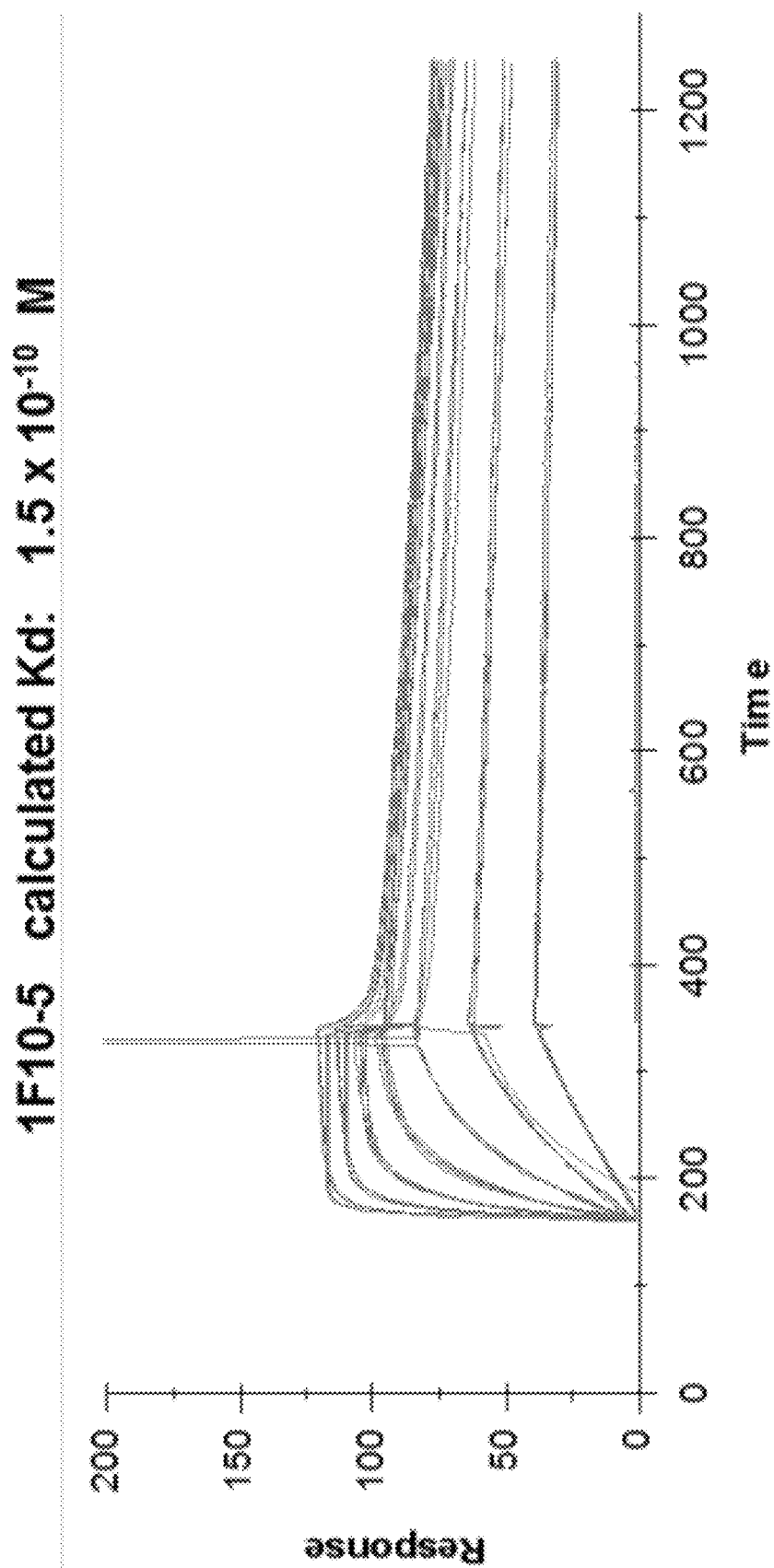
FIG. 8 depicts the results of antigen binding affinity measurements for 1F10-5 mAb using Biacore. Purified human factor D was coupled onto CM4 chip using the amine coupling method. Biacore analysis was performed on a Biacore-2000 instrument. The chip was regenerated between each binding using 50 mM NaOH. The Kd of 1F10-5 was determined to be 1.5 E-10 M.
Figures 9A, 9B:
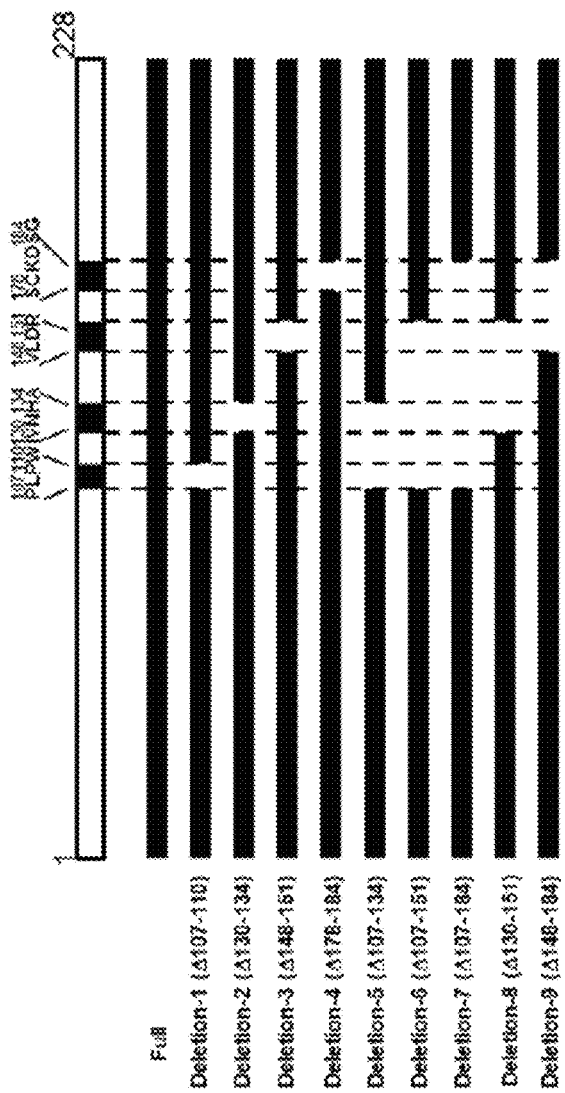
FIGS. 9A through 9D, depicts the results of epitope mapping for mAb 11-8A1 using deletion constructs.
Figures 9C, 9D:
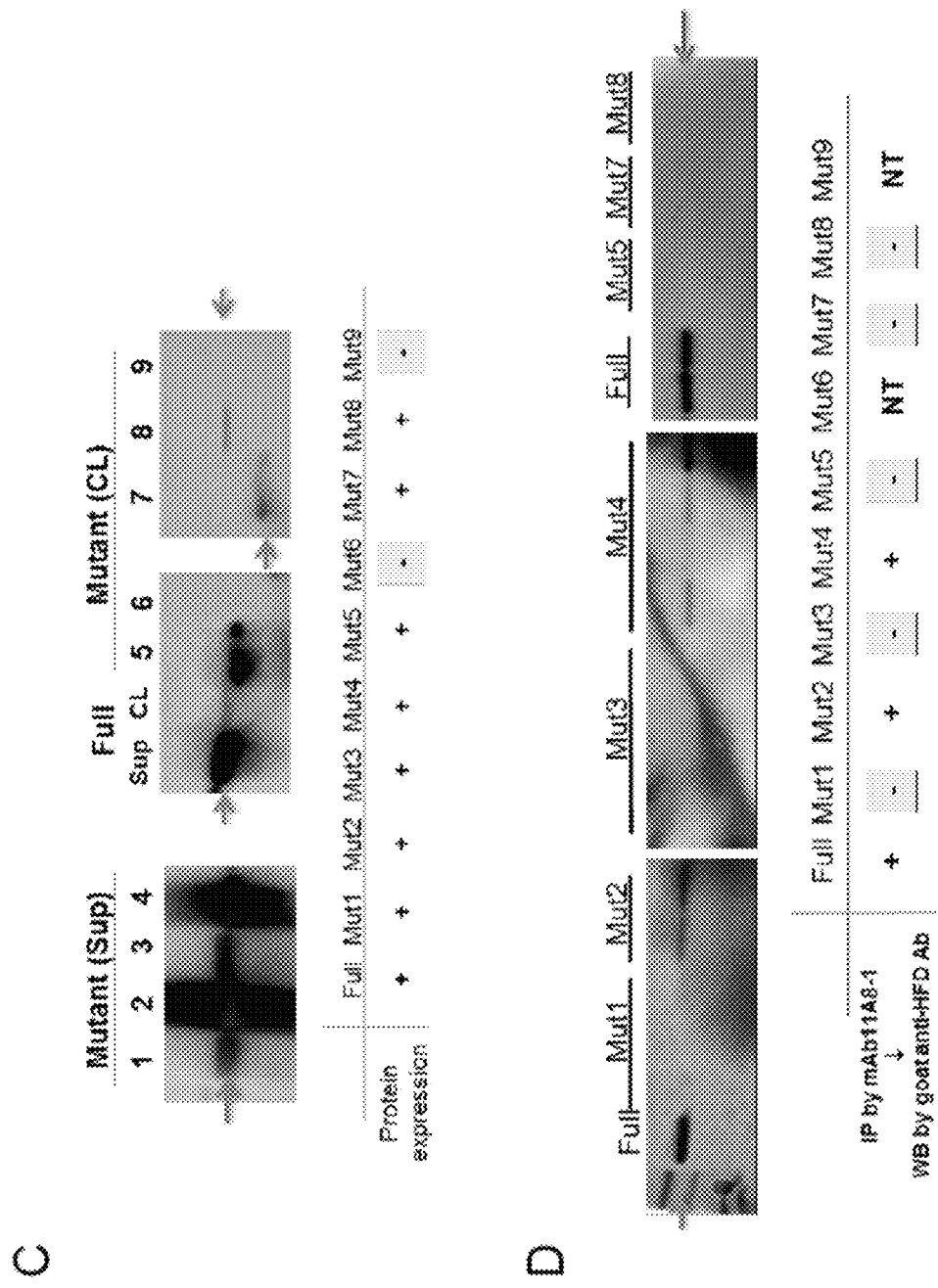
Figure 10:
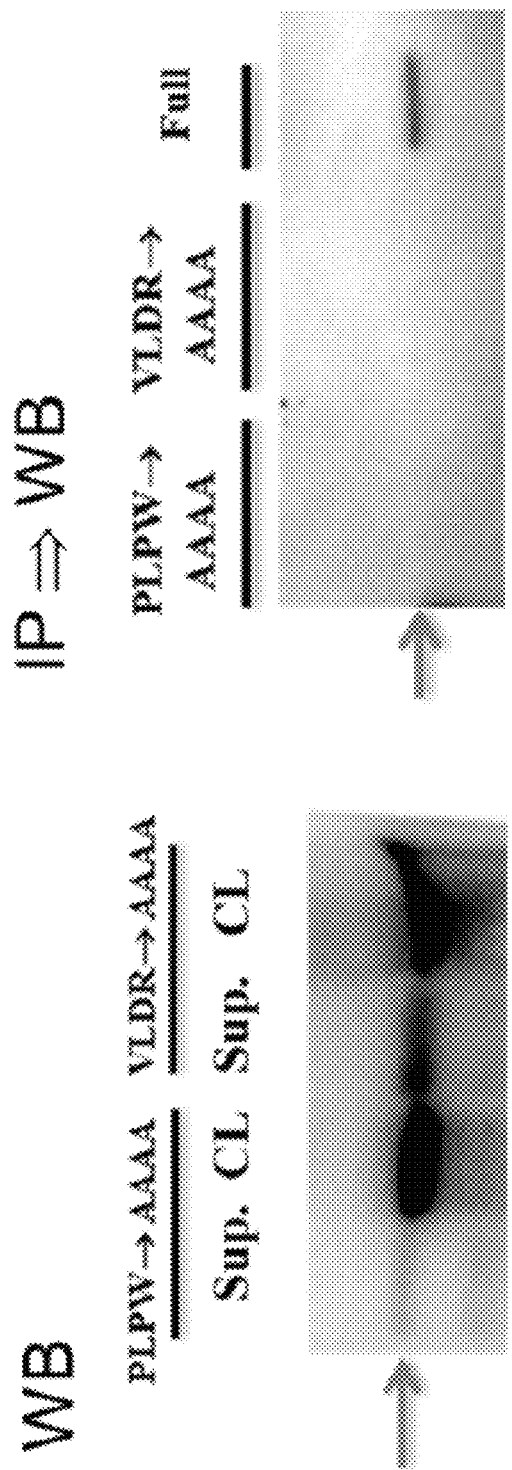
FIG. 10 depicts results of epitope mapping for mAb 11-8A1 by site-directed mutagenesis. Site-directed mutagenesis studies were carried out to confirm two binding sites (107-110 and 148-151) in human factor D that affect mAb 11-8A1 recognition. We introduced replacement of four amino acids PLPW at 107-110 or VLDR at 148-151 with alanine residues (AAAA). CHO cells were transfected with vectors for mutated protein. Mutated protein expression in supernatants and cell lysates (at 48 hours after transfection) was confirmed by Western-blotting using a polyclonal goat anti-human factor D antibody. Both mutations, as expected, impaired the protein recognition by mAb 11-8A1 in IP followed by Western-blotting with goat anti-human factor D antibodies. The results of deletion mutants and mutagenesis studies (PLPW to AAAA, and VLDR to AAAA) indicated that the four amino acid located in PLPW107-110 and VLDR148-151 of human factor D are critical for 11-8A1 binding and functional blocking activity.

This invention relates to the inhibition of the alternative pathway (AP) of complement using an anti-factor D antibody. In various embodiments, the invention is directed to compositions and methods for treating an AP-mediated disease or AP-mediated disorder in an individual by contacting the individual with an anti-factor D antibody. The AP-mediated pathologies and conditions that can be treated with the compositions and methods of the invention include, but are not limited to, macular degeneration (MD), age-related macular degeneration (AMD), ischemia reperfusion injury, arthritis, rheumatoid arthritis, asthma, allergic asthma, paroxysmal nocturnal hemoglobinuria (PNH) syndrome, atypical hemolytic uremic (aHUS) syndrome, epidermolysis bullosa, sepsis, organ transplantation, inflammation (including, but not limited to, inflammation associated with cardiopulmonary bypass surgery and kidney dialysis), C3 glomerulopathy membranous nephropathy, glomerulonephritis (including, but not limited to, anti-neutrophil cytoplasmic antibody (ANCA)-mediated glomerulonephritis, lupus, and combinations thereof), ANCA-mediated vasculitis, Shiga toxin induced HUS, and antiphospholipid antibody-induced pregnancy loss, or any combinations thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "inhibit" and "inhibition," as used herein, means to reduce, suppress, diminish or block an activity or function by at least about 10% relative to a control value. In some embodiments, the activity is suppressed or blocked by 50% compared to a control value, or by 75%, or by 95%.

The terms "effective amount" and "pharmaceutically effective amount" refer to a sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The terms "patient," "subject," "individual," and the like are used interchangeably herein, and refer to any animal, in some embodiments a mammal, and in some embodiments a human, having a complement system, including a human in need of therapy for, or susceptible to, a condition or its sequelae. The individual may include, for example, dogs, cats, pigs, cows, sheep, goats, horses, rats, monkeys, mice and humans.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Operably linked" or "operatively linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "therapeutic treatment" is a treatment administered to a subject who exhibits signs of disease or disorder, for the purpose of diminishing or eliminating those signs.

As used herein, "treating a disease or disorder" means reducing the frequency and/or severity of a sign and/or symptom of the disease or disorder is experienced by a patient.

The phrase "biological sample", "sample" or "specimen" as used herein, is intended to include any sample comprising a cell, a tissue, or a bodily fluid in which expression of a nucleic acid or polypeptide can be detected. The biological sample may contain any biological material suitable for detecting the desired biomarkers, and may comprise cellular and/or non-cellular material obtained from the individual. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "antibody," as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from a subject with heavy chain disease, or prepared by the cloning and expression of VH (variable heavy chain immunoglobulin) genes from a subject.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein, an "immunoassay" refers to any binding assay that uses an antibody capable of binding specifically to a target molecule to detect and quantify the target molecule.br By the term "specifically binds," as used herein with respect to an antibody, is meant an antibody which recognizes and binds to a specific target molecule, but does not substantially recognize or bind other molecules in a sample. In some instances, the terms "specific binding" or "specifically binding," is used to mean that the recognition and binding is dependent upon the presence of a particular structure (e.g., an antigenic determinant or epitope) on the target molecule. If, for example, an antibody specifically binds to epitope "A," the presence of an unlabelled molecule containing epitope A (or free, unlabeled A) in a reaction containing labeled "A" and the antibody, will reduce the amount of labeled A bound to the antibody.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III subtypes. Wild-type type II CRISPR/Cas systems utilize the RNA-mediated nuclease, Cas9 in complex with guide and activating RNA to recognize and cleave foreign nucleic acid. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chloroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39): 15644-9; Sampson et al., Nature. 2013 May 9; 497(7448):254-7; and Jinek, et al., Science. 2012 Aug. 17; 337(6096):816-21.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, or at least about 75%, or at least about 90%, or at least about 95% of the nucleotide residues of the first portion are capable of base pairing with nucleotide residues in the second portion. In some embodiments, all nucleotide residues of the first portion are capable of base pairing with nucleotide residues in the second portion.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Isolated" means altered or removed from the natural state. For example, a nucleic acid or a peptide naturally present in its normal context in a living subject is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "progeny" as used herein refers to a descendent or offspring and includes the offspring of a mammal, and also included the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. In various embodiments, the variant sequence is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to the reference sequence.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "scanning window,", as used herein, refers to a segment of a number of contiguous positions in which a sequence may be evaluated independently of any flanking sequence. A scanning window generally is shifted incrementally along the length of a sequence to be evaluated with each new segment being independently evaluated. An incremental shift may be of 1 or more than one position.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

The term "breeding" is used herein to refer to the propagation of a species with the result being at least one offspring.

The term "natural breeding" is used herein to refer to the propagation of a species by sexual union.

The term "inbred animal" is used herein to refer to an animal that has been interbred with other similar animals of the same species in order to preserve and fix certain characteristics, or to prevent other characteristics from being introduced into the breeding population.

The term "outbred animal" is used herein to refer to an animal that breeds with any other animal or subjects of the same species without regard to the preservation of certain characteristics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This invention relates to the inhibition of the alternative pathway (AP) of complement using an anti-human factor D antibody. In one embodiment, the invention is directed to methods of treating and preventing inflammation and autoimmune diseases mediated by unwanted, uncontrolled, excessive AP complement activation. In one embodiment the invention is directed towards the treatment of AP-mediated disease or AP-mediated disorder in an individual by contacting the individual with an anti-factor D antibody.

In one embodiment, the invention is a method of treating an AP-mediated disease or disorder in an individual, comprising the step of administering to said individual an anti-factor D antibody, thereby inhibiting the generation of a C3bBb protein complex. Examples of complement-mediated pathologies that can be treated using the methods of the invention include, but are not limited macular degeneration (MD), age-related macular degeneration (AMD), ischemia reperfusion injury, arthritis, rheumatoid arthritis, asthma, allergic asthma, paroxysmal nocturnal hemoglobinuria (PNH) syndrome, atypical hemolytic uremic (aHUS) syndrome, epidermolysis bullosa, sepsis, organ transplantation, inflammation (including, but not limited to, inflammation associated with cardiopulmonary bypass surgery and kidney dialysis), C3 glomerulopathy, membranous nephropathy, glomerulonephritis (including, but not limited to, anti-neutrophil cytoplasmic antibody (ANCA)-mediated glomerulonephritis, lupus, and combinations thereof), ANCA-mediated vasculitis, Shiga toxin induced HUS, and antiphospholipid antibody-induced pregnancy loss, or combinations thereof.

The ability of the immune system to discriminate between "self" and "non-self" antigens is vital to the functioning of the immune system as a specific defense against invading microorganisms. "Non-self" antigens are those antigens on substances entering or present in the body which are detectably different or foreign from the subject's own constituents, whereas "self" antigens are those which, in the healthy subject, are not detectably different or foreign from its own constituents. In various embodiments of the methods, the AP activation that is inhibited is that which was triggered by at least one of the group consisting of a microbial antigen, a non-biological foreign surface, altered self-tissue, or combinations thereof. One example of a non-biological foreign surface is blood tubing such as that used in cardio-pulmonary bypass surgery or kidney dialysis. Examples of altered self-tissues include apoptotic, necrotic and ischemia-stressed tissues and cells, or combinations thereof.

In some embodiments, the anti-factor D antibodies of the invention inhibit the AP, but do not inhibit the activation of classical pathway (CP) or the lectin pathway (LP). Generally, the CP is initiated by antigen-antibody complexes, the LP is activated by binding of lectins to sugar molecules on microbial surfaces, while the AP is constitutively active at a low level but can be quickly amplified on bacterial, viral, and parasitic cell surfaces due to the lack of regulatory proteins. Host cells are usually protected from AP complement activation by regulatory proteins. But in some situations, such as when the regulatory proteins are defective or missing, the AP can also be activated uncontrollably on host cells, leading to complement-mediated disease or disorder. The CP consists of components C1, C2, C4 and converges with the AP at the C3 activation step. The LP consists of mannose-binding lectins (MBLs) and MBL-associated serine proteases (Masps) and shares with the CP the components C4 and C2. The AP consists of components C3 and several factors, such as factor B, factor D and the fluid phase regulator factor H. Complement activation consists of three stages: (a) recognition, (b) enzymatic activation, and (c) membrane attack leading to cell death. The first phase of CP complement activation begins with C1. C1 is made up of three distinct proteins: a recognition subunit, C1q, and the serine protease subcomponents, C1r and C1s, which are bound together in a calcium-dependent tetrameric complex, C1r2 s2. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, C4b2a, which in turn cleaves C3 to form C3a and C3b. Activation of the LP is initiated by MBL binding to certain sugars on the target surface and this triggers the activation of Masps which then cleaves C4 and C2 in a manner analogous to the activity of C1s of the CP, resulting in the generation of the C3 convertase, C4b2a. Thus, the CP and LP are activated by different mechanisms but they share the same components C4 and C2 and both pathways lead to the generation of the same C3 convertase, C4b2a. The cleavage of C3 by C4b2a into C3b and C3a is a central event of the complement pathway for two reasons. It initiates the AP amplification loop because surface deposited C3b is a central intermediate of the AP. Both C3a and C3b are biologically important. C3a is proinflammatory and together with C5a are referred to as anaphylatoxins. C3b and its further cleavage products also bind to complement receptors present on neutrophils, eosinophils, monocytes and macrophages, thereby facilitating phagocytosis and clearance of C3b-opsonized particles. Finally, C3b can associate with C4b2a to form the C5 convertase of the CP and LP to activate the terminal complement sequence, leading to the production of C5a, a potent proinflammatory mediator, and the assembly of the lytic membrane attack complex (MAC), C5-C9.

The AP is thought to be constitutively active at a low level due to spontaneous hydrolysis of C3 to form C3(H2O). C3(H2O) behaves like C3b in that it can associate with fB, which make fB susceptible to fD cleavage and activation. The resultant C3(H2O)Bb then cleaves C3 to produce C3b and C3a to initiate the AP cascade by forming the C3 convertase of the AP, C3bBb. As the initial C3 convertase generates increasing amounts of C3b, an amplification loop is established. It should be noted that because the CP and LP also generate C3b, wherein C3b can bind factor B and engages the AP, the AP amplification loop also participates in the CP and LP once these pathways are activated. Thus, the AP consists of two functional entities: an independent complement activation pathway that is unrelated to CP or LP and an amplification process that does participate and contribute to the full manifestation of CP and LP. Thus, in some embodiments, the anti-factor D antibodies of the invention inhibit the amplification process or amplification loop.

In one embodiment, the activity of the AP that is inhibited using a method of the invention is AP activation induced by at least one of the group selected from a lipopolysacchride (LPS), lipooligosaccharide (LOS), pathogen-associated molecular patterns (PAMPs) and danger-associated molecular patterns (DAMPs). In another embodiment, the activity of the AP that is inhibited using a method of invention is the generation of C3bBb protein complex. In another embodiment, the activity of the AP that is inhibited using a method of invention is factor D dependent.

In some embodiments, the methods of the present invention preserve the ability of the individual to combat an infection through the CP and LP. In one embodiment, the invention is a method of inhibiting AP activation induced by bacterial lipooligosaccharide (LOS) in an individual, comprising the step of administering to said individual an anti-factor D antibody, and thereby inhibiting an AP activation induced by bacterial LOS in an individual. In another embodiment, provided herein is a method of inhibiting AP activation induced by a bacterial LPS. In certain embodiments, the AP activation is induced by S. typhosa LPS, and the inhibitors used in the methods provided herein do not inhibit AP activity induced by S. minnesota LPS or E. coli LPS. In various embodiments, the anti-factor D antibodies of the invention inhibit the AP, but do not inhibit CP-triggered complement activation, LP-triggered complement activation, zymosan-induced activation, or cobra venom factor-induced activation.

In one embodiment, provided herein is a method of inhibiting a pathogen-associated molecular pattern-mediated AP activation in an individual, comprising the step of administering to said individual an anti-factor D antibody, thereby inhibiting a PAMP-mediated AP activation in an individual. Examples of PAMPs whose activation of AP can be inhibited by the methods of the invention, include, but are not limited to, a muramyl dipeptide (MDP), a CpG motif from bacterial DNA, double-stranded viral RNAs, a peptidoglycan, a lipoteichoic acid, an outer surface protein A from Borrelia burgdorferi, a synthetic mycoplasmal macrophage-activating lipoprotein-2, tripalmitoyl-cysteinyl-seryl-(lysyl)3-lysine (P3CSK4), a dipalmitoyl-CSK4 (P2-CSK4), a monopalmitoyl-CSK4 (PCSK4), amphotericin B, a triacylated or diacylated bacterial polypeptide, and combinations thereof.

In one embodiment, the invention is a method of inhibiting initiation of AP activation in an individual, comprising the step of administering to said individual an anti-factor D antibody, thereby inhibiting initiation of AP activation in an individual. In another embodiment, provided herein is a method of inhibiting amplification of AP activation in an individual, comprising the step of administering to said individual an inhibitor of the AP, thereby inhibiting amplification of AP activation in an individual. Examples of these embodiments are PNH patients who suffer from AP complement-mediated hemolysis and individuals suffering from AP complement-mediated aHUS, asthma, ischemic/reperfusion injury, rheumatoid arthritis and ANCA-mediated kidney diseases. In various embodiments of the invention, diseases and disorders that can be treated using the compositions and methods of the invention include, but are not limited to, AP complement-mediated hemolysis, AP complement-mediated aHUS, asthma, ischemic/reperfusion injury, rheumatoid arthritis and ANCA-mediated kidney diseases or disorders.

In various embodiments, provided herein are methods of identifying a potential antibody having inhibitory effects on the AP, comprising the steps of: a) administering the anti-factor D antibody to an individual; b) measuring the resulting phenotype of the individual; and c) comparing the resulting phenotype of the individual to the phenotype of a factor $D^{-/-}$ knockout animal. In another embodiment, the anti-factor D antibody used in the methods provided herein is identified by the method of selecting a potential therapeutic compound using the factor $D^{-/-}$ knockout animal.

In various other embodiments, provided herein are methods of identifying a potential anti-factor D antibody having inhibitory effects on the AP. One such method includes the steps of: a) coating a plate with lipopolysaccharide (LPS); b) washing the plate to remove unbound LPS; c) adding bovine serum albumin (BSA) in phosphate buffered saline (PBS); d) washing the plate to remove unbound BSA; e) adding a mixture of a candidate anti-factor D antibody compound that has been pre-incubated with serum and is mixed into normal human serum; 0 washing the plate; g) adding an HRP-conjugated anti-human C3 antibody; h) washing the plate to remove unbound antibody; i) adding HRP Substrate Reagent; j) adding sulphuric acid to stop the reaction; k) measuring the optical density at 450 nm; 1) comparing the optical density of the plate containing the candidate anti-factor D antibody compound to the optical density of a positive comparator control and a negative comparator control; wherein when the optical density is diminished as compared with the positive comparator control, the anti-factor D antibody is identified.

Anti-Factor D Antibodies

In some embodiments, the invention includes compositions comprising an antibody that specifically binds to factor D. In one embodiment, the anti-factor D antibody is a polyclonal antibody. In another embodiment, the anti-factor D antibody is a monoclonal antibody. In some embodiments, the anti-factor D antibody is a chimeric antibody. In further embodiments, the anti-factor D antibody is a humanized antibody. In some embodiments, the antibody is an antibody fragment. In some embodiments, the factor D is human factor D.

In some embodiments, binding of the antibody or the fragment of the antibody to human-factor D is associated with a reduction in the generation of C3bBb in the complement activation pathway in an intact organism. In some embodiments, the invention is a protein or a polypeptide capable of binding to human factor D. In some embodiments, the antibody or antibody fragment; the protein or the polypeptide binds to a relevant portion or fraction or epitope of the human-factor D; and the binding of the antibody, or the antibody fragment thereof, or the protein or the polypeptide to the relevant portion of the human-factor D is associated with a reduction in the generation of C3bBb in an intact organism.

In some embodiments, the anti-factor D binding antibody or a factor D binding antibody fragment thereof, is conjugated to a protein, a peptide or other compound. In some embodiments, the protein, peptide or other compound to which the anti-factor D antibody or antibody fragment thereof is conjugated is a targeting moiety (i.e., the targeting moiety specifically binds to a molecule other than factor D). In some embodiments, the protein, peptide, or other compound to which the anti-factor D antibody or antibody fragment thereof is conjugated to is an effector molecule (e.g., a cytotoxic molecule).

In one embodiment, the anti-factor D antibody or an antigen-binding fragment thereof comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, the anti-factor D antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In some embodiments, the anti-factor D antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-factor D antibody or an antigen-binding fragment thereof comprises: VH-CDR1 comprising the amino acid sequence of SEQ ID NO:3; and VL-CDR1: SEQ ID NO:8.

In some embodiments, the anti-factor D antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-factor D antibody or an antigen-binding fragment thereof comprises: VH-CDR2 comprising the amino acid sequence of SEQ ID NO:4; and VL-CDR2: SEQ ID NO:9.

In some embodiments, the anti-factor D antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-factor D antibody or an antigen-binding fragment thereof comprises: VH-CDR3 comprising the amino acid sequence of SEQ ID NO:5; and VL-CDR3: SEQ ID NO:10.

In some embodiments, the anti-factor D antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO: 8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-factor D antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-factor D antibody or antigen-binding fragment thereof comprises: VH-CDR1 comprising the amino acid sequence of SEQ ID NO:3; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-comprising the amino acid sequence of SEQ ID NO:10.

In some embodiments, the anti-factor D antibody or an antigen binding fragment thereof comprises a heavy chain comprising the amino acid sequence of SEQ ID NO:2, or a variant thereof. In other embodiments, the anti-factor D antibody comprises a light chain comprising the amino acid sequence of SEQ ID NO:7, or a variant thereof. In another embodiment, the anti-factor D antibody is a monoclonal antibody designated mAb 11-8A1. The monoclonal anti-factor D antibody designated mAb 11-8A1 comprises a heavy chain comprising the amino acid sequence of SEQ ID NO:2, or a variant thereof, and a light chain comprising the amino acid sequence of SEQ ID NO:7, or a variant thereof. In some embodiments, the monoclonal anti-factor D antibody is humanized. In some embodiments, the monoclonal anti-factor D antibody designated mAb 11-8A1 is a chimeric antibody.

In one embodiment, the anti-factor D antibody or an antigen binding fragment thereof comprises at least one of the CDRs selected from the group consisting of: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20, or a variant or variants thereof. In another embodiment, the anti-factor D antibody comprises all of the CDRs of the group consisting of: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20, or a variant or variants thereof.

In some embodiments, the anti-factor D antibody or antigen-binding fragment thereof comprises: VH-CDR1 comprising the amino acid sequence of SEQ ID NO:13 or a variant thereof comprising up to about 3 (such as about any of 1, 2, or 3) amino acid substitutions; and VL-CDR1: SEQ ID NO:18, or a variant thereof comprising up to about 3 (such as about any of 1, 2, or 3) amino acid substitutions. In some embodiments, the anti-factor D antibody or an antigen-binding fragment thereof comprises: VH-CDR1 comprising the amino acid sequence of SEQ ID NO:13; and VL-CDR1: SEQ ID NO:18.

In some embodiments, the anti-factor D antibody or antigen-binding fragment thereof comprises: VH-CDR2 comprising the amino acid sequence of SEQ ID NO:14, or a variant thereof comprising up to about 3 (such as about any of 1, 2, or 3) amino acid substitutions; and VL-CDR2: SEQ ID NO:19, or a variant thereof comprising up to about 3 (such as about any of 1, 2, or 3) amino acid substitutions. In some embodiments, the anti-factor D antibody or an antigen-binding fragment thereof comprises: VH-CDR2 comprising the amino acid sequence of SEQ ID NO:14; and VL-CDR2: SEQ ID NO:19.

In some embodiments, the anti-factor D antibody or antigen-binding fragment thereof comprises: VH-CDR3 comprising the amino acid sequence of SEQ ID NO:15, or a variant thereof comprising up to about 3 (such as about any of 1, 2, or 3) amino acid substitutions; and VL-CDR3: SEQ ID NO:20, or a variant thereof comprising up to about 3 (such as about any of 1, 2, or 3) amino acid substitutions. In some embodiments, the anti-factor D antibody or an antigen-binding fragment thereof comprises: VH-CDR3 comprising the amino acid sequence of SEQ ID NO:15; and VL-CDR3: SEQ ID NO:20.

In some embodiments, the anti-factor D antibody or antigen-binding fragment thereof comprises: VH-CDR1 comprising the amino acid sequence of SEQ ID NO:13, or a variant thereof comprising up to about 3 (such as about any of 1, 2, or 3) amino acid substitutions; VH-CDR2 comprising the amino acid sequence of SEQ ID NO:14, or a variant thereof comprising up to about 3 (such as about any of 1, 2, or 3) amino acid substitutions; VH-CDR3 comprising the amino acid sequence of SEQ ID NO:15, or a variant thereof comprising up to about 3 (such as about any of 1, 2, or 3) amino acid substitutions; VL-CDR1 comprising the amino acid sequence of SEQ ID NO:18, or a variant thereof comprising up to about 3 (such as about any of 1, 2, or 3) amino acid substitutions; VL-CDR2 comprising the amino acid sequence of SEQ ID NO:19, or a variant thereof comprising up to about 3 (such as about any of 1, 2, or 3) amino acid substitutions; and VL-CDR3 comprising the amino acid sequence of SEQ ID NO:20, or a variant thereof comprising up to about 3 (such as about any of 1, 2, or 3) amino acid substitutions.

In some embodiments, the anti-factor D antibody or antigen-binding fragment thereof comprises: VH-CDR1 comprising the amino acid sequence of SEQ ID NO:13, or a variant thereof comprising up to about 3 (such as about any of 1, 2, or 3) amino acid substitutions; VH-CDR2 comprising the amino acid sequence of SEQ ID NO:14, or a variant thereof comprising up to about 3 (such as about any of 1, 2, or 3) amino acid substitutions; VH-CDR3 comprising the amino acid sequence of SEQ ID NO:15; VL-CDR1 comprising the amino acid sequence of SEQ ID NO:18, or a variant thereof comprising up to about 3 (such as about any of 1, 2, or 3) amino acid substitutions; VL-CDR2 comprising the amino acid sequence of SEQ ID NO:19, or a variant thereof comprising up to about 3 (such as about any of 1, 2, or 3) amino acid substitutions; and VL-CDR3 comprising the amino acid sequence of SEQ ID NO:20.

In some embodiments, the anti-factor D antibody or antigen-binding fragment thereof comprises: VH-CDR1 comprising the amino acid sequence of SEQ ID NO:13; VH-CDR2 comprising the amino acid sequence of SEQ ID NO:14; VH-CDR3 comprising the amino acid sequence of SEQ ID NO:15; VL-CDR1 comprising the amino acid sequence of SEQ ID NO:18; VL-CDR2 comprising the amino acid sequence of SEQ ID NO:19; and VL-CDR3 comprising the amino acid sequence of SEQ ID NO:20.

In some embodiments, the anti-factor D antibody comprises a heavy chain comprising the amino acid sequence of SEQ ID NO:12, or a variant thereof. In other embodiments, the anti-factor D antibody comprises a light chain comprising the amino acid sequence of SEQ ID NO:17, or a variant thereof. In another embodiment, the anti-factor D antibody is a monoclonal antibody designated mAb 1F10-5. The monoclonal anti-factor D antibody designated mAb 1F10-5 comprises a heavy chain comprising the amino acid sequence of SEQ ID NO:12, or a variant thereof, and a light chain comprising the amino acid sequence of SEQ ID NO:17, or a variant thereof. In some embodiments, the monoclonal anti-factor D antibody is humanized. In some embodiments the monoclonal anti-factor D antibody is a chimeric antibody.

In some embodiments, the isolated antibody binds to human factor D, wherein the antibody alternatively binds to either one of a first epitope and a second epitope of factor D, wherein both the first epitope and the second epitope have portions that assume a coil conformation in their secondary structure, and wherein a portion of factor D that assumes a beta-strand conformation in its secondary structure is between the first epitope and the second epitope.

In some embodiments, the anti-factor D antibody of the invention is one that binds to a specific epitope of factor D. In one embodiment, at least one (such as at least 1, 2, 3, or 4) of the amino acids of SEQ ID NO:21 is in the epitope of the anti-factor D antibody. The amino acids of SEQ ID NO:21 correspond to the amino acids 107-110 of the factor D amino acid sequence. In one embodiment, at least one (such as at least 1, 2, 3, or 4) of the amino acids of SEQ ID NO:22 is in the epitope of the anti-factor D antibody. The amino acids of SEQ ID NO:22 correspond to the amino acids 148-151 of the factor D amino acid sequence. In one embodiment, at least one (such as at least 1, 2, 3, 4, or 5) of the amino acids of SEQ ID NO:23 is in the epitope of the anti-factor D antibody. The amino acids of SEQ ID NO:23 correspond to the amino acids 155-159 of the factor D amino acid sequence. In one embodiment, at least one (such as at least 1, 2, 3, or 4) of the amino acids of SEQ ID NO:24 is in the epitope of the anti-factor D antibody. The amino acids of SEQ ID NO:24 correspond to the amino acids 173-176 of the factor D amino acid sequence.

In one embodiment, the anti-factor D antibody is an antibody that binds to at least one (such as at least 1, 2, 3, or 4) amino acid of SEQ ID NO: 21. In one embodiment, the anti-factor D antibody is an antibody that binds to at least one (such as at least 1, 2, 3, or 4) amino acid of SEQ ID NO: 22. In one embodiment, the anti-factor D antibody is an antibody that binds to at least one (such as at least 1, 2, 3, 4, or 5) amino acid of SEQ ID NO: 23. In one embodiment, the anti-factor D antibody is an antibody that binds to at least one (such as at least 1, 2, 3, or 4) amino acid of SEQ ID NO: 24.

In another embodiment, the anti-factor D antibody is an antibody that competes for binding with an antibody that binds to at least one (such as at least 1, 2, 3, or 4) amino acid of SEQ ID NO: 21. In another embodiment, the anti-factor D antibody is an antibody that competes for binding with an antibody that binds to at least one (such as at least 1, 2, 3, or 4) amino acid of SEQ ID NO: 22. In another embodiment, the anti-factor D antibody is an antibody that competes for binding with an antibody that binds to at least one (such as at least 1, 2, 3, 4, or 5) amino acid of SEQ ID NO: 23. In another embodiment, the anti-factor D antibody is an antibody that competes for binding with an antibody that binds to at least one (such as at least 1, 2, 3, or 4) amino acid of SEQ ID NO: 24.

In some embodiments, binding of the anti-human factor D antibody, or an antigen-binding fragment thereof, to at least any one (such as at least 1, 2, 3, 4, or 5) of the amino acid sequences selected from SEQ ID NOs. 21, 22, 23 and 24 of human factor D within a living organism is associated with a reduction in the C3bBb generation of the organism. In some embodiments the organism is human. In some embodiments the anti-factor D antibody is either mAb 11-8A1 or mAb IF10-5. In some embodiments, administration of a therapeutically effective amount of mAb 11-8A1 or mAb IF10-5 systemically to an organism, reduces the generation of C3bBb in the complement activation pathway in the organism. In some embodiments the organism is human. In some embodiments, the invention relates to a protein, an antibody, an antibody fragment, or a peptide, that can bind to at least one (such as at least 1, 2, 3, 4, or 5) amino acid sequence selected from SEQ ID NOs. 21, 22, 23 and 24 of human factor D, and which when administered at a therapeutically effective dose to an organism is capable of reducing the generation of C3bBb in the alternative complement activation pathway of the organism. In some embodiments the organism is human. In some embodiments, the invention relates to a protein, an antibody, an antibody fragment, or a peptide, that can bind to at least one (such as at least 1, 2, 3, 4, or 5) amino acid sequence selected from SEQ ID NOs. 21, 22, 23 and 24 of human factor D, which prevents the catalytic cleavage of AP factor B to Ba and Bb. In some embodiments, the present application encompasses an antibody or a fragment thereof, a protein or a peptide which can bind to four amino acids having a sequence of PLPW located at positions 107-110, of human factor D or four amino acids having a sequence of VLDR located at positions 148-151 of human factor D and exhibit human factor D blocking activity.

In some embodiments the antibodies are chimeric antibodies. In some embodiments the anti-human factor D antibody may comprise human light chain and human heavy chain constant regions in combination with the variable region CDR sequences, or a variant thereof, described elsewhere in the specification. One of skill in the art would be able to prepare and obtain a chimeric antibody using known techniques of swapping relevant domains of specific antibodies of interest. Such an antibody is easily prepared by grafting heterogeneous antibody domains, incorporating one or more CDR sequences described in this application. Using known recombinant technology, it is possible to obtain and prepare a recombinant antibody comprising heavy and light chain constant regions encoded by nucleic acid sequences of human heavy and light chain constant regions; and the heavy and light chain variable regions comprising CDRs encoded by nucleic acid sequences corresponding to the CDR sequences set forth in the disclosure. One of skill in the art can prepare an anti-human factor D antibody comprises one or more CDR sequences described in this disclosure, wherein portions of the light chain alone or portions of the heavy chain alone are replaced with regions from an antibody belonging to another species, such as a human. An human anti-human-factor D antibody comprising variable regions having one or more CDR sequences selected from SEQ ID NOs. 3-5, 8-10, 13-15 and 18-20, or a variant or variants thereof, in combination with murine or non-murine antibody structural elements outside the CDR regions can be prepared by routine methods known in the art. In some embodiments, the antibodies or antibody fragments are further humanized using known techniques in the art.

In some embodiments the anti-factor D antibody comprises an antibody having at least about 85% (such as at least about any of 85%, 86%, 87%, 88%, 89%, 90%, 91%, 92%, 93%, 94%, 95%, 96%, 97%, 98%, 99%, or 100%) amino acid identity with one or more of the CDR sequences described herein, listed in SEQ ID NOs 3-5, 8-10, 13-15 and 18-20.

In one embodiment, the current disclosure encompasses an anti-factor D antibody having CDR sequences of about 85%, identity to the CDR sequences described herein. The current disclosure encompasses an anti-factor D antibody, or antigen binding fragment thereof, having CDR sequences that are at least about 85%, 86%, 87%, 88%, 89%, 90%, 91%, 92%, 93%, 94%, 95%, 96%, 97% and 99% identical to the CDR sequences described herein. In one embodiment, the antibody against human factor D has a heavy chain variable (vH) region and a light chain variable (vL) region, wherein the vH region has an amino acid sequence that is at least about 85% identical to SEQ ID NO: 2, and wherein the vL region has an amino acid sequence that is at least about 85% identical to SEQ ID NO: 7.

In some embodiments the antibody or the antibody fragment is modified. In some embodiments the modifications include fusion of the antibody or the antigen-binding fragment thereof with portions of another protein, or a protein fragment. In some embodiments the antibody or the antibody fragment thereof of the invention is modified to increase the circulating half-life of the same in vivo. For example, the antibody of the fragment may be fused with an FcRn molecule, which is also known as neonatal Fc receptor to stabilize the antibody in vivo. (Nature Reviews Immunology 7:715-725). In some embodiments, the antibody or antigen-binding fragment thereof is conjugated (e.g., fused) to an effector molecule and/or another targeting moiety (such as an antibody or antibody fragment recognizing a different molecule, different antigen or a different epitope).

One of skill in the art would be able to prepare human-factor D binding single chain variable fragment (scFv), comprising at least one specific CDR sequence selected from SEQ ID NOs 3-5, 8-9, 13-15, and 18-20, or a variant or variants thereof. An scFv may comprise heavy chain variable region sequences designated in SEQ ID NOs 3-5, or a variant or variants thereof, and light chain variable regions designated in SEQ ID NOs 8-10, or a variant or variants thereof. An scFv may comprise heavy chain variable region sequences designated in SEQ ID NOs 13-15, or a variant or variants thereof, and light chain variable regions designated SEQ ID NOs 18-20, or a variant or variants thereof. CDR sequences incorporated within the scFv having amino acid sequence identity of at least about 85% 86%, 87%, 88%, 89%, 90%, 91%, 92%, 93%, 94%, 95%, 96%, 97%, 98%, and 99% to the CDR sequences described in the present disclosure are encompassed within the scope of the present disclosure. The scFv binds to a human factor D, such as to an epitope within at least one of the amino acid sequences listed in the group consisting of SEQ ID NO. 21, SEQ ID NO. 22, SEQ ID NO. 23, and SEQ ID NO. 24.

Screening Assays

The present invention has application in various screening assays, including, determining whether a candidate anti-factor D antibody can inhibit the AP.

In some embodiments, the level of AP activity in the presence of the candidate anti-factor D antibody is compared with AP activity detected in a positive comparator control. The positive comparator control comprises AP activation in the absence of added test compound. In some embodiments, the candidate anti-factor D antibody is identified as an inhibitor of the AP when the AP activity in the presence of the candidate anti-factor D antibody is less than about 70% of the AP activity detected in a positive comparator control; this corresponds to greater than about 30% inhibition of AP activity in the presence of the test compound. In other embodiments, the candidate anti-factor D antibody is identified as an inhibitor of the AP when the AP activity in the presence of the candidate anti-factor D antibody is less than about 80% of the AP activity detected in a positive comparator control; this corresponds to greater than about 20% inhibition of AP activity in the presence of the test compound. In still other embodiments, the candidate anti-factor D antibody is identified as an inhibitor of the AP when the AP activity in the presence of the candidate anti-factor D antibody is less than about 90% of the AP activity detected in a positive comparator control; this corresponds to greater than about 10% inhibition of AP activity in the presence of the test compound. In some embodiments, the level of AP inhibition by the candidate anti-factor D antibody is compared with the level of inhibition detected in a negative comparator control.

A variety of immunoassay formats, including competitive and non-competitive immunoassay formats, antigen capture assays, two-antibody sandwich assays, and three-antibody sandwich assays are useful methods of the invention (Self et al., 1996, Curr. Opin. Biotechnol. 7:60-65). The invention should not be construed to be limited to any one type of known or heretofor unknown assay, provided that the assay is able to detect the inhibition of the AP.

Extravascular hemolytic assays are included in the methods of the invention. In various embodiments, red blood cells (RBCs) are obtained from normal (healthy) individuals or from individuals displaying signs or symptoms of a disease or disorder, such as, for example, PNH. In various embodiments, the disease or disorder is induced in an animal model such as a Crry/DAF/C3 triple knockout (TKO) mouse. In some embodiments, the recipients of the transfused RBCs are treated 24 hours before RBC transfer with at least one anti-factor D antibody or a control solution such as PBS. Donor RBCs are washed and labeled with CFSE using a method such as that described by Miwa et at, 2002, Blood 99; 3707-3716. In some embodiments, donor RBCs are harvested from normal donors, washed and labeled with DDAO-SE using a technique described by the manufacturer or that one skilled in the art would find appropriate. In some embodiments, a 1:1 mixture of normal RBCs to TKO RBCs in injected into a recipient via an intravenous mode deemed most appropriate by the artisan including but not limited to tail vein in the case of a mouse recipient. In one embodiment, blood samples are collected at various time points after injection of donor RBCs. In one embodiment, blood samples are collected 5 minutes, 6, 24, 48, 72, 96 and 120 hours following transfusion. Collected blood is analyzed to determine the percentage of CFSE- or DDAO-SE-labeled (i.e. transfused) RBCs remaining in the circulation. The number of CFSE-labeled TKO RBCs in each recipient is normalized to DDAO-SE labeled normal RBC at each time point.

Treatment of KRN arthritis is a useful method of the invention. Arthritis is induced in homozygous human factor D knock-in mice by passive transfer of purified total IgGs from K/B×N mice. In one embodiment, ankle thickening is measured by a caliper and clinical scored are recorded using criteria such as that previously published by Kimura et. al. (Kimura et al., 2010, JCI; 3545-3554). Subjects are treated with a dose of an anti-human factor D antibody. In some embodiments, the subject is treated at day 1, day 3, day 7, and 11, and day 15 following induction of arthritis.

Enzyme-linked immunosorbent assays (ELISAs) are useful in the methods of the invention. An enzyme such as, but not limited to, horseradish peroxidase (HRP), alkaline phosphatase, beta-galactosidase or urease can be linked, for example, to an anti-C3 antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Chemiluminescent detection is also useful for detecting the inhibition of the AP. Chemiluminescent secondary antibodies may be obtained from any number of commercial sources.

Fluorescent detection is also useful for detecting the inhibition of the AP. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antibodies.

Radioimmunoassays (RIAs) are also useful in the methods of the invention. Such assays are well known in the art, and are described for example in Brophy et al. (1990, Biochem. Biophys. Res. Comm. 167:898-903) and Guechot et al. (1996, Clin. Chem. 42:558-563). Radioimmunoassays are performed, for example, using Iodine-125-labeled primary or secondary antibody (Harlow et al., supra, 1999).

A signal emitted from a detectable antibody is analyzed, for example, using a spectrophotometer to detect color from a chromogenic substrate; a radiation counter to detect radiation, such as a gamma counter for detection of Iodine-125;

or a fluorometer to detect fluorescence in the presence of light of a certain wavelength. Where an enzyme-linked assay is used, quantitative analysis is performed using a spectrophotometer. It is understood that the assays of the invention can be performed manually or, if desired, can be automated and that the signal emitted from multiple samples can be detected simultaneously in many systems available commercially.

The methods of the invention also encompass the use of capillary electrophoresis based immunoassays (CEIA), which can be automated, if desired. Immunoassays also may be used in conjunction with laser-induced fluorescence as described, for example, in Schmalzing et al. (1997, Electrophoresis 18:2184-2193) and Bao (1997, J. Chromatogr. B. Biomed. Sci. 699:463-480). Liposome immunoassays, such as flow-injection liposome immunoassays and liposome immunosensors, may also be used according to the methods of the invention (Rongen et al., 1997, J. Immunol. Methods 204:105-133).

Quantitative western blotting may also be used to determine the level of AP inhibition in the methods of the invention. Western blots are quantified using well known methods such as scanning densitometry (Parra et al., 1998, J. Vasc. Surg. 28:669-675).

Methods of Administration

The methods of the invention comprise administering a therapeutically effective amount of at least one anti-factor D antibody, or binding fragment thereof (such as any of the antibodies or fragments thereof described elsewhere herein), to an individual identified as having an AP-mediated disease or disorder. In one embodiment the individual is a mammal having an AP system. In one embodiment the individual is a human. In various embodiments, the at least one anti-factor D antibody, or binding fragment thereof, is administered locally, regionally, or systemically. In some embodiments, the AP-mediated disease or disorder is C3 glomerulopathy. In some embodiments, the AP-mediated disease or disorder is macular degeneration (such as AMD).

The methods of the invention can comprise the administration of at least one anti-factor D antibody, or binding fragment thereof, but the present invention should in no way be construed to be limited to the anti-factor D antibodies described herein, but rather should be construed to encompass any anti-factor D antibody, both known and unknown, that diminish and reduce AP activation.

The method of the invention comprises administering a therapeutically effective amount of at least one anti-factor D antibody, or binding fragment thereof, to an individual wherein a composition of the present invention comprising at least one anti-factor D antibody, or binding fragment thereof, either alone or in combination with at least one other therapeutic agent. The invention can be used in combination with other treatment modalities, such as, for example antiinflammatory therapies, and the like. Examples of antiinflammatory therapies that can be used in combination with the methods of the invention include, for example, therapies that employ steroidal drugs, as well as therapies that employ non-steroidal drugs.

The method of the invention comprises administering a therapeutically effective amount of an anti-factor D antibody, or an antigen-binding fragment thereof, to a subject, the antibody capable of binding within any one of the sequences selected from SEQ. ID NOs 21, 22, 23, 24. In some embodiments, the invention encompasses a method of treatment of factor D related diseases involving dysregulation of the AP complement pathway by administering a therapeutically effective amount of an antibody of the invention, or a therapeutically effective amount of an antibody fragment thereof such that a reduction of C3bBb is effected in the subject. In some embodiments the invention encompasses a method of treatment of factor D related diseases involving dysregulation of the AP complement pathway by administering a therapeutically effective amount of an antibody or an antibody fragment, capable of binding to certain specific epitope or epitopes within human factor D, such as an epitope comprised within the amino acids sequences selected from SEQ ID NOs 21-24. In some embodiments the invention encompasses a method of treatment of factor D related diseases involving dysregulation of the AP complement pathway by administering to a subject an effective amount of an antibody, an antibody fragment, a polypeptide, a peptide, a conjugated peptide, capable of binding to certain specific epitopes within human factor D, wherein the epitope is comprised within the amino acid sequences selected from SEQ ID NOs 21-24, such that the AP complement activation pathway activation is reduced in the subject. In some embodiments, the method of treatment encompasses administering to a subject a systemically effective dose of an antibody or an antibody fragment, capable of binding within the amino acids selected from the sequences listed in SEQ ID NOs 21-24 whereby systemic reduction of C3bBb is effected in the subject.

Pharmaceutical Compositions and Therapies

Administration of an anti-factor D antibody, or binding fragment thereof, in a method of treatment of the invention can be achieved in a number of different ways, using methods known in the art. The therapeutic and prophylactic methods of the invention thus encompass the use of pharmaceutical compositions comprising an anti-factor D antibody.

The pharmaceutical compositions useful for practicing the invention may be administered to deliver a dose of at least about 1 ng/kg, at least about 5 ng/kg, at least about 10 ng/kg, at least about 25 ng/kg, at least about 50 ng/kg, at least about 100 ng/kg, at least about 500 ng/kg, at least about 1 µg/kg, at least about 5 µg/kg, at least about 10 µg/kg, at least about 25 µg/kg, at least about 50 µg/kg, at least about 100 µg/kg, at least about 500 µg/kg, at least about 1 mg/kg, at least about 5 mg/kg, at least about 10 mg/kg, at least about 25 mg/kg, at least about 50 mg/kg, at least about 100 mg/kg, at least about 200 mg/kg, at least about 300 mg/kg, at least about 400 mg/kg, and at least about 500 mg/kg of body weight of the subject. In one embodiment, the invention administers a dose which results in a concentration of the anti-factor D antibody of the present invention of at least about 1 pM, at least about 10 pM, at least about 100 pM, at least about 1 nM, at least about 10 nM, at least about 100 nM, at least about 1 µM, at least about 2 µM, at least about 3 µM, at least about 4 µM, at least about 5 µM, at least about 6 µM, at least about 7 µM, at least about 8 µM, at least about 9 µM and at least about 10 µM in an individual. In another embodiment, the invention envisions administration of a dose which results in a concentration of the anti-factor D antibody of the present invention between at least about 1 pM, at least about 10 pM, at least about 100 pM, at least about 1 nM, at least about 10 nM, at least about 100 nM, at least about 1 µM, at least about 2 µM, at least about 3 µM, at least about 4 µM, at least about 5 µM, at least about 6 µM, at least about 7 µM, at least about 8 µM, at least about 9 µM and at least about 10 µM in the plasma of an individual.

In some embodiments, the pharmaceutical compositions useful for practicing the invention may be administered to deliver a dose of no more than about 1 ng/kg, no more than about 5 ng/kg, no more than about 10 ng/kg, no more than about 25 ng/kg, no more than about 50 ng/kg, no more than about 100 ng/kg, no more than about 500 ng/kg, no more than about 1 µg/kg, no more than about 5 µg/kg, no more than about 10 µg/kg, no more than about 25 µg/kg, no more than about 50 µg/kg, no more than about 100 µg/kg, no more than about 500 µg/kg, no more than about 1 mg/kg, no more than about 5 mg/kg, no more than about 10 mg/kg, no more than about 25 mg/kg, no more than about 50 mg/kg, no more than about 100 mg/kg, no more than about 200 mg/kg, no more than about 300 mg/kg, no more than about 400 mg/kg, and no more than about 500 mg/kg of body weight of the subject. In one embodiment, the invention administers a dose which results in a concentration of the anti-factor D antibody of the present invention of no more than about 1 pM, no more than about 10 pM, no more than about 100 pM, no more than about 1 nM, no more than about 10 nM, no more than about 100 nM, no more than about 1 µM, no more than about 2 µM, no more than about 3 µM, no more than about 4 µM, no more than about 5 µM, no more than about 6 µM, no more than about 7 µM, no more than about 8 µM, no more than about 9 µM and no more than about 10 µM in an individual. In another embodiment, the invention envisions administration of a dose which results in a concentration of the anti-factor D antibody of the present invention between no more than about 1 pM, no more than about 10 pM, no more than about 100 pM, no more than about 1 nM, no more than about 10 nM, no more than about 100 nM, no more than about 1 µM, no more than about 2 µM, no more than about 3 µM, no more than about 4 µM, no more than about 5 µM, no more than about 6 µM, no more than about 7 µM, no more than about 8 µM, no more than about 9 µM and no more than about 10 µM in the plasma of an individual. Also contemplated are dosage ranges between any of the doses disclosed herein.

Typically, dosages which may be administered in a method of the invention to a subject, in some embodiments a human, range in amount from 0.5 µg to about 50 mg per kilogram of body weight of the subject. While the precise dosage administered will vary depending upon any number of factors, including but not limited to, the type of subject and type of disease state being treated, the age of the subject and the route of administration. In some embodiments, the dosage of the compound will vary from about 1 µg to about 10 mg per kilogram of body weight of the subject. In other embodiments, the dosage will vary from about 3 µg to about 1 mg per kilogram of body weight of the subject.

The compound may be administered to a subject as frequently as several times daily, or it may be administered less frequently, such as once a day, twice a day, thrice a day, once a week, twice a week, thrice a week, once every two weeks, twice every two weeks, thrice every two weeks, once a month, twice a month, thrice a month, or even less frequently, such as once every several months or even once or a few times a year or less. The frequency of the dose will be readily apparent to the skilled artisan and will depend upon any number of factors, such as, but not limited to, the type and severity of the disease being treated, the type and age of the subject, etc. The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various subjects is well understood, and the ordinarily skilled veterinary pharmacologist can design and perform such modification with merely ordinary, if any, experimentation. Individuals to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intraocular, intravitreal, intramuscular, intradermal and intravenous routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to an individual or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the individual treated and further depending upon the route by which the composition is to be administered. By way of example, the composition may comprise between 0.1% and 100% (w/w) active ingredient. In various embodiments, the composition comprises at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% (w/w) active ingredient In addition to the active ingredient, a pharmaceutical composition of the invention may further comprise one or more additional pharmaceutically active agents.

Controlled- or sustained-release formulations of a pharmaceutical composition of the invention may be made using conventional technology.

Parenteral administration of a pharmaceutical composition includes any route of administration characterized by physical breaching of a tissue of an individual and administration of the pharmaceutical composition through the breach in the tissue. Parental administration can be local, regional or systemic. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraocular, intravitreal, subcutaneous, intraperitoneal, intramuscular, intradermal, intrasternal injection, and intratumoral.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and in some embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. In some embodiments, dry powder compositions include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. In some embodiments, the droplets provided by this route of administration have an average diameter in the range from about 0.1 to about 200 nanometers.

The formulations are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more additional ingredients.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more additional ingredients. Alternately, formulations suitable for buccal administration may comprise a powder or an aerosolized or atomized solution or suspension comprising the active ingredient. In some embodiments, such powdered, aerosolized, or aerosolized formulations, when dispersed, have an average particle or droplet size in the range from about 0.1 to about 200 nanometers, and may further comprise one or more additional ingredients.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Cells Producing Antibodies and Antigen Binding Fragments Thereof

In some embodiments, the invention is a cell or cell line (such as host cells) that produces at least one of the anti-factor D antibodies, or antigen binding fragments, described herein. In one embodiment, the cell or cell line is a genetically modified cell that produces at least one of the anti-factor D antibodies, or antigen binding fragments, described herein. In one embodiment, the cell or cell line is a hybridoma that produces at least one of the anti-factor D antibodies, or antigen binding fragments, described herein.

Hybrid cells (hybridomas) are generally produced from mass fusions between murine splenocytes, which are highly enriched for B-lymphocytes, and myeloma "fusion partner cells" (Alberts et al., Molecular Biology of the Cell (Garland Publishing, Inc. 1994); Harlow et al., Antibodies. A Laboratory Manual (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are referred to as monoclonal antibodies.

Also provided are nucleic acids encoding any of the antibodies, or antibody fragments, disclosed herein, as well as vectors comprising the nucleic acids. Thus, the antibodies and fragments of the invention can be generated by expressing the nucleic acid in a cell or a cell line, such as the cell lines typically used for expression of recombinant or humanized immunoglobulins. Thus, the antibodies and fragments of the invention can also be generated by cloning the nucleic acids into one or more expression vectors, and transforming the vector into a cell line such as the cell lines typically used for expression of recombinant or humanized immunoglobulins.

The genes encoding the heavy and light chains of immunoglobulins, or fragments thereof, can be engineered according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al., 1992, J. Immunol. 148:1149). For example, genes encoding heavy and light chains, or fragments thereof, can be cloned from an antibody secreting cell's genomic DNA, or cDNA is produced by reverse transcription of the cell's RNA. Cloning is accomplished by conventional techniques including the use of PCR primers that hybridize to the sequences flanking or overlapping the genes, or segments of genes, to be cloned.

Nucleic acids encoding the antibody of the invention, or the heavy chain or light chain or fragments thereof, can be obtained and used in accordance with recombinant nucleic acid techniques for the production of the specific immunoglobulin, immunoglobulin chain, or a fragment or variant thereof, in a variety of host cells or in an in vitro translation system. For example, the antibody-encoding nucleic acids, or fragments thereof, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

In some embodiments, the heavy and light chains, or fragments thereof, can be assembled in two different expression vectors that can be used to co-transfect a recipient cell. In some embodiments, each vector can contain two or more selectable genes, one for selection in a bacterial system and one for selection in a eukaryotic system. These vectors allow for the production and amplification of the genes in a bacterial system, and subsequent co-transfection of eukaryotic cells and selection of the co-transfected cells. The selection procedure can be used to select for the expression of antibody nucleic acids introduced on two different DNA vectors into a eukaryotic cell.

Alternatively, the nucleic acids encoding the heavy and light chains, or fragments thereof, may be expressed from one vector. Although the light and heavy chains are coded for by separate genes, they can be joined, using recombinant methods. For example, the two polypeptides can be joined by a synthetic linker that enables them to be made as a single protein chain in which the $V_L$ and $V_H$ regions pair to form monovalent molecules (known as single chain Fv (scFv); see e.g., Bird et al., 1988, Science 242: 423-426; and Huston et al., 1988, Proc. Natl. Acad. Sci. USA 85:5879-5883).

The invention provides for an isolated nucleic acid molecule comprising a nucleic acid sequence encoding a heavy chain and/or a light chain, as well as fragments thereof. A nucleic acid molecule comprising sequences encoding both the light and heavy chain, or fragments thereof, can be engineered to contain a synthetic signal sequence for secretion of the antibody, or fragment, when produced in a cell. Furthermore, the nucleic acid molecule can contain specific DNA links which allow for the insertion of other antibody sequences and maintain the translational reading frame so to not alter the amino acids normally found in antibody sequences.

In accordance with the present invention, antibody-encoding nucleic acid sequences can be inserted into an appropriate expression vector. In various embodiments, the expression vector comprises the necessary elements for transcription and translation of the inserted antibody-encoding nucleic acid so as to generate recombinant DNA molecules that direct the expression of antibody sequences for the formation of an antibody, or a fragment thereof.

The antibody-encoding nucleic acids, or fragments thereof, can be subjected to various recombinant nucleic acid techniques known to those skilled in the art such as site-directed mutagenesis.

A variety of methods can be used to express nucleic acids in a cell. Nucleic acids can be cloned into a number of types of vectors. However, the present invention should not be construed to be limited to any particular vector. Instead, the present invention should be construed to encompass a wide variety of vectors which are readily available and/or known in the art. For example, the nucleic acid of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Viral vector technology is well known in the art and is described, for example, in Sambrook et al. (2012), and in Ausubel et al. (1999), and in other virology and molecular biology manuals. Viruses, which are useful as vectors include, but are not limited to, retroviruses, adenoviruses, adeno-associated viruses, herpes viruses, and lentiviruses. In some embodiments, a murine stem cell virus (MSCV) vector is used to express a desired nucleic acid. MSCV vectors have been demonstrated to efficiently express desired nucleic acids in cells. However, the invention should not be limited to only using a MSCV vector, rather any retroviral expression method is included in the invention. Other examples of viral vectors are those based upon Moloney Murine Leukemia Virus (MoMuLV) and HIV. In some embodiments, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

Additional regulatory elements, e.g., enhancers, can be used modulate the frequency of transcriptional initiation. A promoter may be one naturally associated with a gene or nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high-level expression of the introduced DNA segment, such as is advantageous in the large-scale production of recombinant proteins and fragments thereof.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter or cell-type specific promoter, which is a promoter that is active only in a desired tissue or cell. Tissue-specific promoters are well known in the art and include, but are not limited to, the HER-2 promoter and the PSA associated promoter sequences.

In order to assess the expression of the nucleic acids, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate nucleic acid and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing nucleic acids into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, laserporation and the like. Methods for producing cells comprising vectors and/or exogenous nucleic acids are well-known in the art. See, for example, Sambrook et al. (2012) and Ausubel et al. (1999).

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The preparation and use of such systems is well known in the art.

Regardless of the method used to introduce exogenous nucleic acids into a host cell or otherwise expose a cell to the nucleic acid of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Human Factor D Expressing Non-Human Animals

The invention also includes a genetically modified non-human animal that expresses human factor D. In some embodiments, the genetically modified non-human animal that expresses human factor D does not express non-human animal factor D. In one embodiment, the invention is a genetically modified non-human animal that expresses human factor D from the non-human animal's endogenous regulatory elements, but does not express non-human animal factor D. In some embodiments, the non-human animal is a mammal. In some embodiments, the non-human animal is a rodent. In some embodiments, the non-human animal is a rat or a mouse.

To create a genetically modified non-human animal, a nucleic acid encoding the human factor D protein can be incorporated into a recombinant expression vector in a form suitable for expression of the human factor D protein in a host cell. The term "in a form suitable for expression of the fusion protein in a host cell" is intended to mean that the recombinant expression vector includes one or more regulatory sequences operatively linked to the nucleic acid encoding the human factor D protein in a manner which allows for transcription of the nucleic acid into mRNA and translation of the mRNA into the human factor D protein. The term "regulatory sequence" is art-recognized and intended to include promoters, enhancers and other expression control elements (e.g., polyadenylation signals). Such regulatory sequences are known to those skilled in the art and are described in 1990, Goeddel, Gene Expression Technology: Methods in Enzymology 185, Academic Press, San Diego, Calif. It should be understood that the design of the expression vector may depend on such factors as the choice of the host cell to be transfected and/or the amount of human factor D protein to be expressed.

A genetically modified non-human animal can be created, for example, by introducing a nucleic acid encoding the human factor D protein (typically linked to appropriate regulatory elements, such as a constitutive or tissue-specific enhancer) into oocyte, e.g., by microinjection, and allowing the oocyte to develop in a female founder mouse. Intronic sequences and polyadenylation signals can also be included in the transgene to increase the efficiency of expression of the transgene. Methods for generating genetically modified animals, such as mice, have become conventional in the art and are described, for example, in U.S. Pat. Nos. 4,736,866 and 4,870,009 and 1986, Hogan et al., A Laboratory Manual, Cold Spring Harbor, N.Y., Cold Spring Harbor Laboratory. A genetically modified founder animal can be used to breed additional subjects carrying the transgene. Genetically modified animals carrying a transgene encoding the factor D protein of the invention can further be bred to other genetically modified animals carrying other transgenes, or to other knockout animals, e.g., a knockout mouse that does not express the murine factor D gene. It will be understood that in addition to genetically modified animals, the system can be used to generate other human factor D expressing subjects.

In one embodiment, a genetically modified non-human animal that expresses human factor D from the non-human animal's regulatory elements, but does not express the non-human animal's factor D, is generated using a system that replaces the non-human animal's factor D exon sequences (or exon and intron sequences) with human factor D exon sequences (or exon and intron sequences), but leaves one, more, or all of the native non-human animal's regulatory elements (e.g., promoter, enhancers, flanking regions, introns, etc.) sequences unchanged. Although any suitable system can be used, one exemplary system capable of producing a genetically modified non-human animal in this way is the CRISPr/Cas9 system. The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III subtypes. Wild-type type II CRISPR/Cas systems utilize the RNA-mediated nuclease, Cas9 in complex with guide and activating RNA to recognize and cleave foreign nucleic acid. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39): 15644-9; Sampson et al., Nature. 2013 May 9; 497(7448):254-7; and Jinek, et al., Science. 2012 Aug. 17; 337(6096):816-21

In one embodiment, the genetically modified non-human animal of the invention expresses human factor D from a chicken (3-actin promoter with CVM-IE enhancer, but the skilled artisan will understand that the genetically modified non-human animal of the invention encompasses the expression of human factor D from other promoters and enhancers. Examples of promoters useful in the invention include, but are not limited to, the native mouse promoter, DNA pol II promoter, PGK promoter, ubiquitin promoter, albumin promoter, globin promoter, ovalbumin promoter, SV40 early promoter, the Rous sarcoma virus (RSV) promoter, retroviral LTR, and lentiviral LTR. Promoter and enhancer expression systems useful in the invention also include inducible and/or tissue-specific expression systems.

The genetically modified non-human animals described herein can be useful for various research and clinical uses. In some embodiments, the present application provides methods of screening an anti-factor D compound (such as an antibody). In some embodiments, the present application provides methods of validating an anti-factor D compound (such as an antibody). In some embodiments, the present application provides methods of assessing the therapeutic efficacy of anti-factor D compound (such as an antibody) in a variety of complement-mediated diseases and disorders, including diseases and disorders that can be induced in the humanized non-human animal or diseases or disorders that can develop spontaneously in double mutant non-human animals that can be produced by cross-breeding the human factor D non-human animal with another mutant non-human animal having another muations and that can develop a complement-associated disease or disorder (see for example Lesher, 2013, J. Am. Soc. Nephrol. 24:53-65; Ueda et al., 2017, Blood March 2; 129:1184-1196).

Kits

The invention also includes a kit comprising an anti-factor D antibody, or combinations thereof, of the invention and an instructional material which describes, for instance, administering the anti-factor D antibody, or combinations thereof, to an individual as a therapeutic treatment or a non-treatment use as described elsewhere herein. In an embodiment, this kit further comprises a pharmaceutically acceptable carrier suitable for dissolving or suspending the therapeutic composition, comprising an anti-factor D antibody, or combinations thereof, of the invention, for instance, prior to administering the antibody to an individual. Optionally, the kit comprises an applicator for administering the antibody.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore and are not to be construed as limiting in any way the remainder of the disclosure.

Example 1

Anti-human factor D monoclonal antibodies were generated using the hybridoma method first described by Kohler et al. (1975, Nature, 256:495) with some modifications. Balb/c female (Jackson laboratory) mice were immunized with 100 µg of purified human factor D (from human plasma) emulsified with adjuvant. At day 21 and day 35, the mice were again immunized with 100 µg of purified human factor D emulsified with adjuvant. Mice were boosted with 25 µg of purified human factor D two times before fusion. Then, mice were sacrificed by cervical dislocation and spleen was isolated for preparation of single cell suspension by mechanical disruption. The spleen cell suspension was washed once with HYB-SFM (Invitrogen)+10% FBS medium and cells were counted, and mixed with X63-Ag8.653 myeloma cells (ATCC) in a 2:1 ratio. Cell mixture was again washed with HYB-SFM medium, and the cell pellet was prepared by centrifugation (1000 rpm×5 min). The cell pellet was gently disturbed and loosened and then cell fusion was induced by slowly adding poly ethylene glycol (PEG 1500) (1.5 ml PEG for 3× i 08 cells). The cells were left for 1 min at 37° C. and then 20 ml HYB-SFM medium were added to the cells in 3 min (1 ml for the first minute, 3 ml for the second minute and 16 ml for the third minute). The mixture was centrifuged at 1000 rpm for 5 min and the cells were plated in 24 well plates in HAT medium (10 ml HAT [Sigma H0262], 5 ml Pen/Strep, 500 µl Gentamicin and 10% FBS in 500 ml HYB-SFM medium). After 2 weeks, supernatants from wells with visible colonies were withdrawn for screening of reactivity with purified human factor D by ELISA, Positive clones were picked up and plated in 96 well plates by limiting dilution method to obtain single clones after second round screening by ELISA. Positive clones were expanded in HT-medium (10 ml HT, 5 ml Pen/Strep 500 µl Gentamicin and 10% FBS in 500 ml HYB-SFM medium). Before antibody collection, the hybridoma cells were switched to serum-free medium (HYB-SFM) for 2-3 days. Cell culture medium was collected for mAb purification by protein G affinity chromatography.

Example 2

Micro titer plates were coated with Lipopolysaccharide (LPS) (2 µg/well) in PBS (phosphate buffered saline) at 37° C. for 1 hour. After washing the Plates with PBST (phosphate buffered saline and 0.05% tween) for 3 times plates were blocked with 1% BSA in PBS for 1 hour at RT. Either 10% normal human serum (NHS), normal cynomolgiis serum, normal rhesus monkey serum, normal guinea pig serum, normal mouse serum was pre incubated with different concentration of 11A8-1 mAb or 1F10-5 mAb or chimeric 11A8-1 at 4° C. for 1 hour. 10% Serum in Mg++-EGTA GVB++ buffer served as a positive control and 10% Serum in GVB++ EDTA buffer served as a negative control. Plates were incubated with NHS at 37° C. for 1 hour, and then stopped with Cold 10 mM EDTA in PBS and washed for 3 times. Plates were incubated with HRP conjugated goat anti human C3 polyclonal or anti mouse C3 polyclonal C3 antibody 1:4000 diluted in blocking buffer at room temperature for 1 hour. Plated were washed 3 times and developed with HRP substrate for 6-10 min. The reaction was stopped with 2N H2SO4 and plate was read at 450 nm in a micro plate reader.

Example 3

Polystyrene microtiter plates were coated with purified human factor D (50 ng/well) in PBS at 37° C. for 1 hour. After aspirating the factor D solution, wells were blocked with PBS containing 1% BSA in PBS at room temperature for 1 hour. Wells without fD coating served as background controls. Different concentration of 11A8-1 mAb or 1F10-5 mAb or chimeric 11A8-1, 50 μl/well in blocking solution, were added to the wells. Following 1-hour incubation at room temperature, the wells were extensively washed with PBST. Human factor D-bound mAb was detected by the addition of anti-mouse IgG HRP at a 1:4000 dilution in blocking solution, which was allowed to incubate for 1 h at RT. After washing with PBST, the plate was developed with HRP substrate for 6-10 min. The reaction was stopped with 2N H2SO4 and plate was read at 450 nm in a micro plate reader.

Example 4

Surface Plasmon resonance analysis was used to measure the association and dissociation rate constant for binding of human factor D to immobilized 11A8-1 mAb, 1F10-5 mAb and chimeric 11A8-1 using BIAcore 3000 instrument (Biacore AB, Uppsala, Sweden) and all Biacore experiments were performed at 25° C. The carboxylated dextran matrix of a CM5 sensor chip was used to couple the purified antibody, 11A8-1 mAb, 1F10-5 mAb and chimeric 11A8-1 by amine coupling chemistry to obtain 400-500 RU surface density. The human fD was diluted to 100, 50, 25, 12.5, 6.25, 3.12, 1.56 and 0 nM in HBSET (HEPES buffer saline EDTA with Tween 20) buffer and the samples were injected on the 11A8-1 mAb, 1F10-5 mAb and chimeric 11A8-1 surface at 30 μl/min (60 μl injection) for 120 s and dissociation of bound analyte was allowed to proceed for 900 s. The data were analyzed by the BIA evaluation software 3.2 assuming bivalent binding model. Regeneration of the surface was achieved with a 50 μl injection (50 μl/min) of 50 mM NaOH.

Example 5

To clone the cDNAs of 11A8-1 and 1F10-5, total RNAs were isolated from the hybridoma cells by TRizol reagent (Sigma). First-strand cDNAs were synthesized by reverse transcription using Oligo(dT) primer, to amplify the heavy chain cDNAs (for IgG1, IgG2a/b), the following primers were used in PCR reactions: 5'-GAG GTG A AGCTG GTG G AG(T/A) C (T/A) GG-3' (SEQ ID NO:68) and 5'-GGGGCCAGTGGATAGAC-3' (SEQ ID NO:69). To amplify the k light chain, the following primers were used: mixture of 4 upstream primers: 5 CCAGTTCCGAGCTCCAGATGACCCAGACTCCA-3' (SEQ ID NO:70); 5'-CCAGTTCCGAGCTCGTGCT-CACCCAGTCTCCA-3' (SEQ ID NO:71); 5'-CCAGTTCCGAGCTCCAGATGACCCAGTCTCCA-3' (SEQ ID NO:72); 5'-CC AGTTC CG A G CTC GTG ATG AC AC AGTCTCC A-3' (SEQ 1D NO:73); downstream primer: 5'-GTTGGTGCAGCATCAGC-3, (SEQ ID NO:74). The PCR amplicons were cloned into pCR TOPO TA 2.1 vector (Invitrogen) and sequenced. To obtain the signal peptide (leader) sequence of the mAbs, the 5'-RACE method was used with a kit (GeneRacer) from Invitrogen. The complete variable region cDNAs were amplified using specific primers determined from the 5'-RACE and the initial sequencing data.

Example 6

Figure 11A:
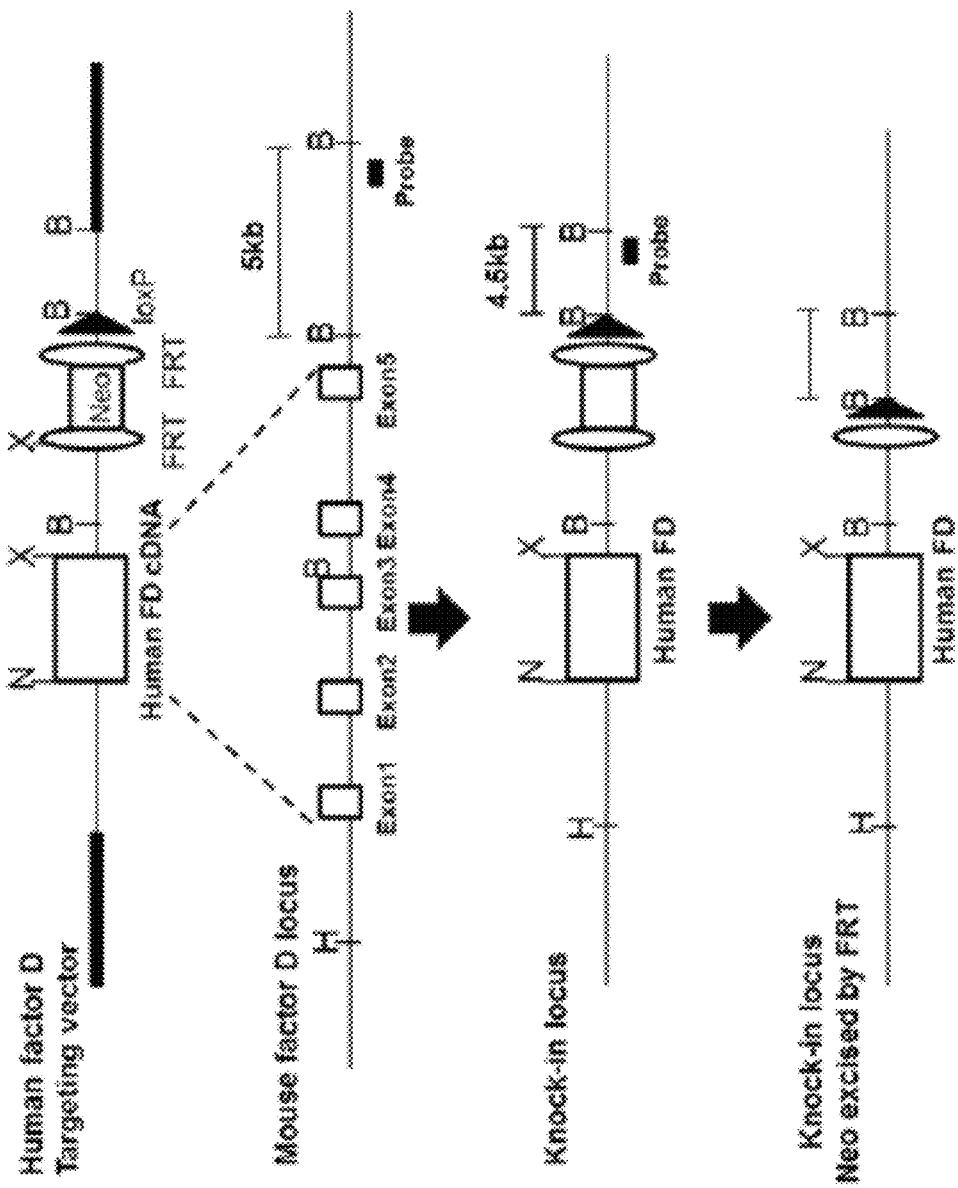
Figure 11B:
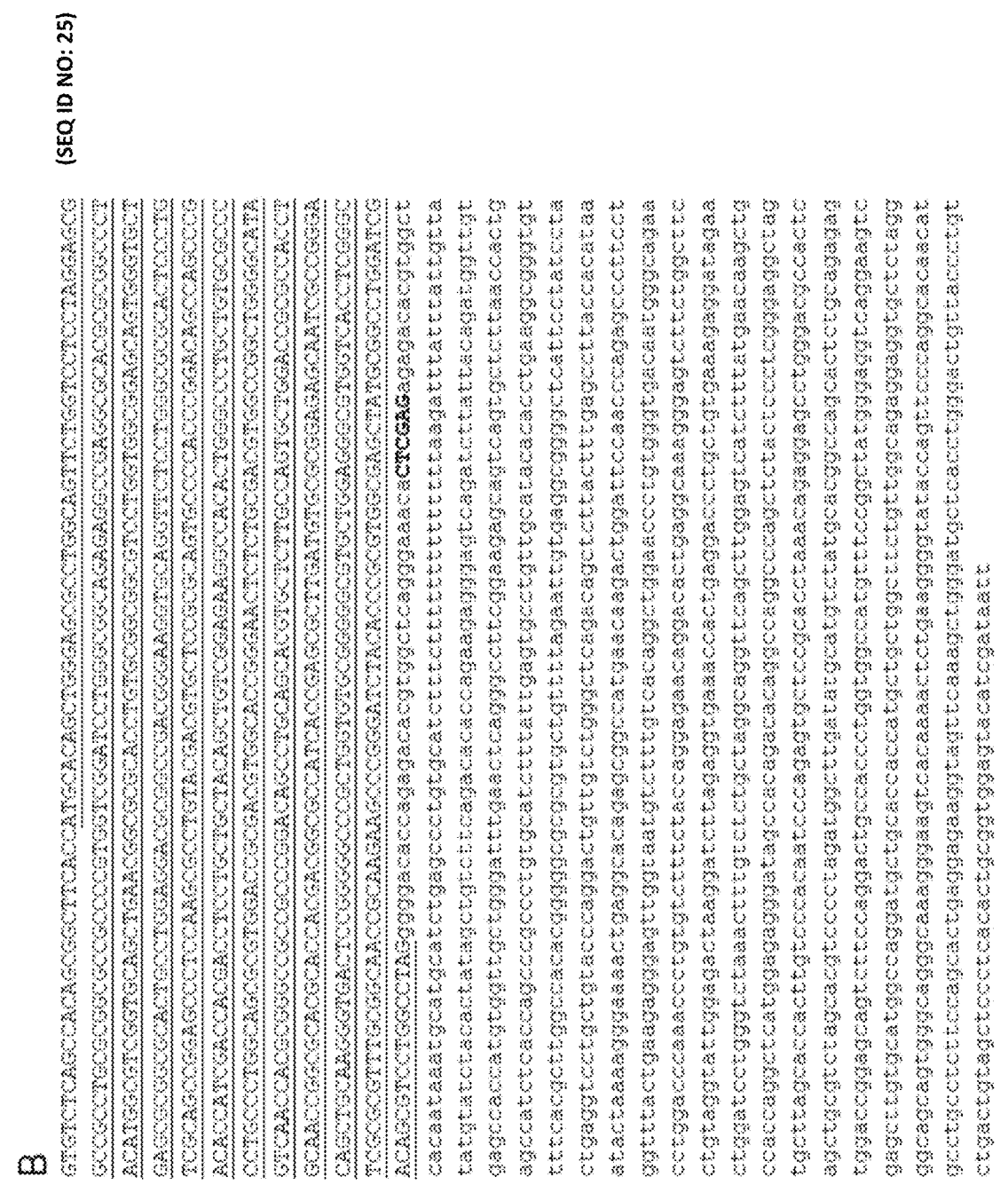
Figure 11C:
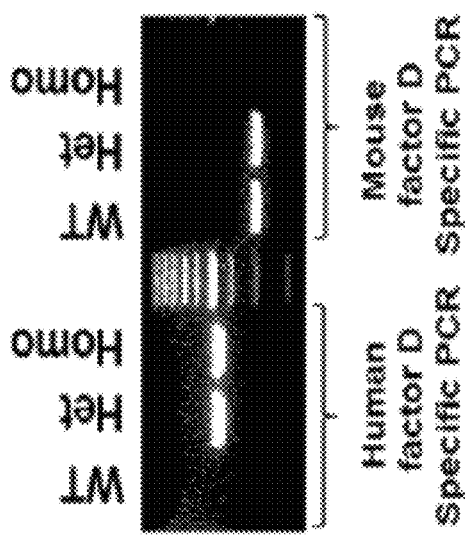
Figure 11D:
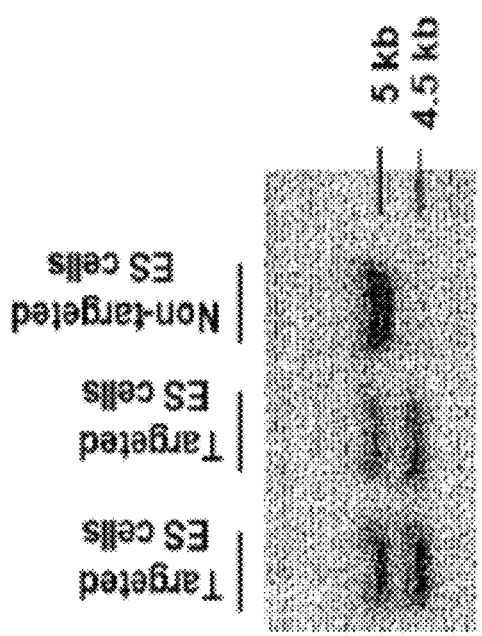
Figures 12A, 12B:
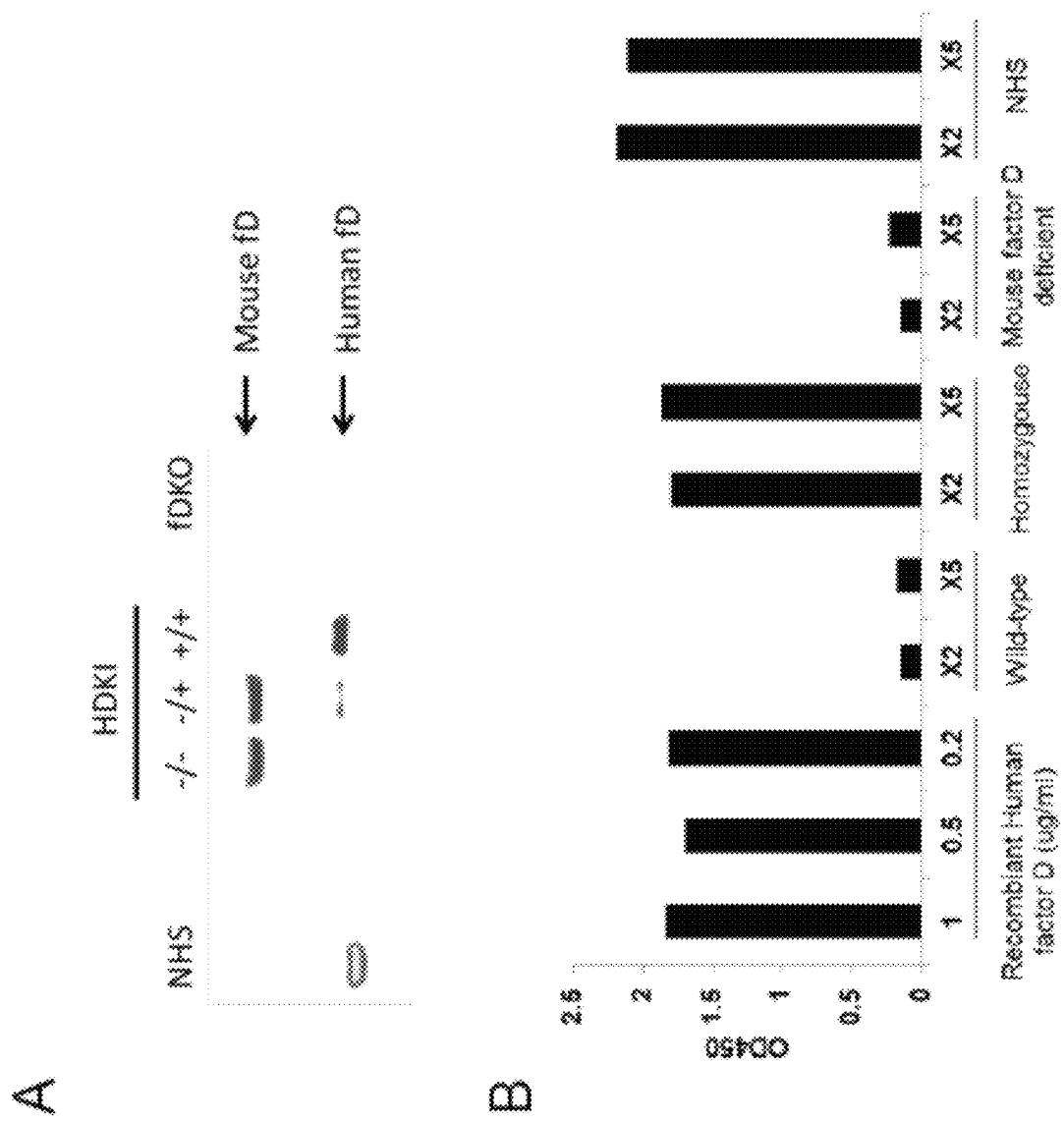
FIGS. 12A and 12B, depicts results of experiments evaluating human factor D expression in sera of human factor D knock-in mice. Western-blotting and ELISA were performed to confirm the presence of human factor D protein in sera of the human factor D knock-in mice. Serum samples were prepared from mice with 3 different genotypes, wild-type, heterozygous and homozygous. NHS and serum of mouse factor D knockout mice (fDKO) were used for assay controls.
Figure 13:
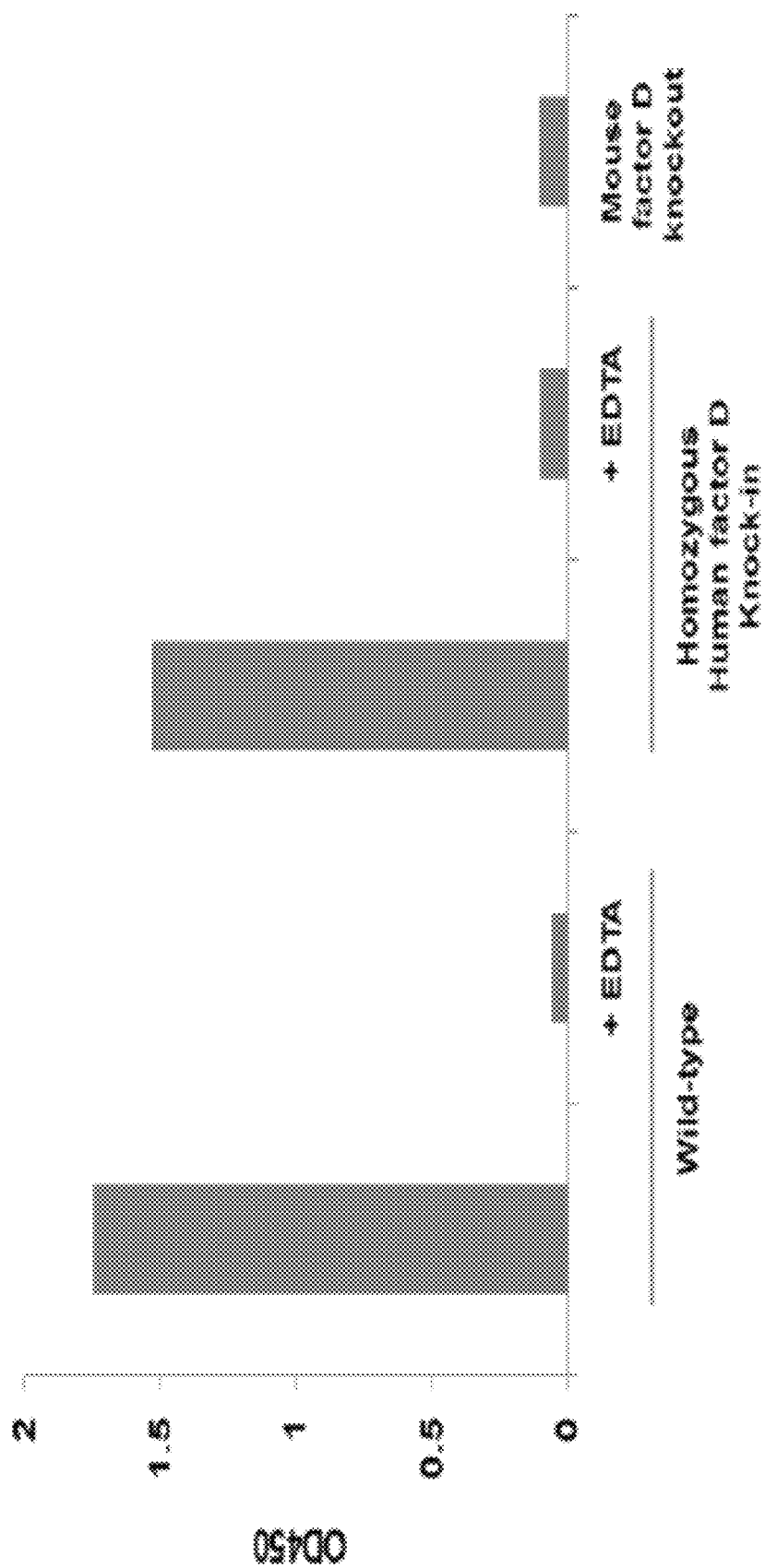
FIG. 13 depicts the results of experiments evaluating LPS-induced AP complement activity in sera of human factor D knock-in mice. Even in the absence of moue factor D, AP complement activity in homozygous human factor D knock-in mice was detected, suggesting human factor D expressed in these mice was functional in vivo. As shown, LPS-induced AP complement activation assay indicated that homozygous human factor D knock-in mice as well as wild-type mice had serum AP complement activity. On the other hand, in this assay, no AP complement activity was detected in serum of mouse factor D knockout mice, nor in WT or homozygous knock-in mouse serum treated with EDTA. These observations demonstrated that expression of human factor D was able to restore mouse AP complement activity and that knock-in mice can be used as an experimental animal model for investigating factor D targeted therapy in AP complement-mediated diseases and disorders.
Figure 14:
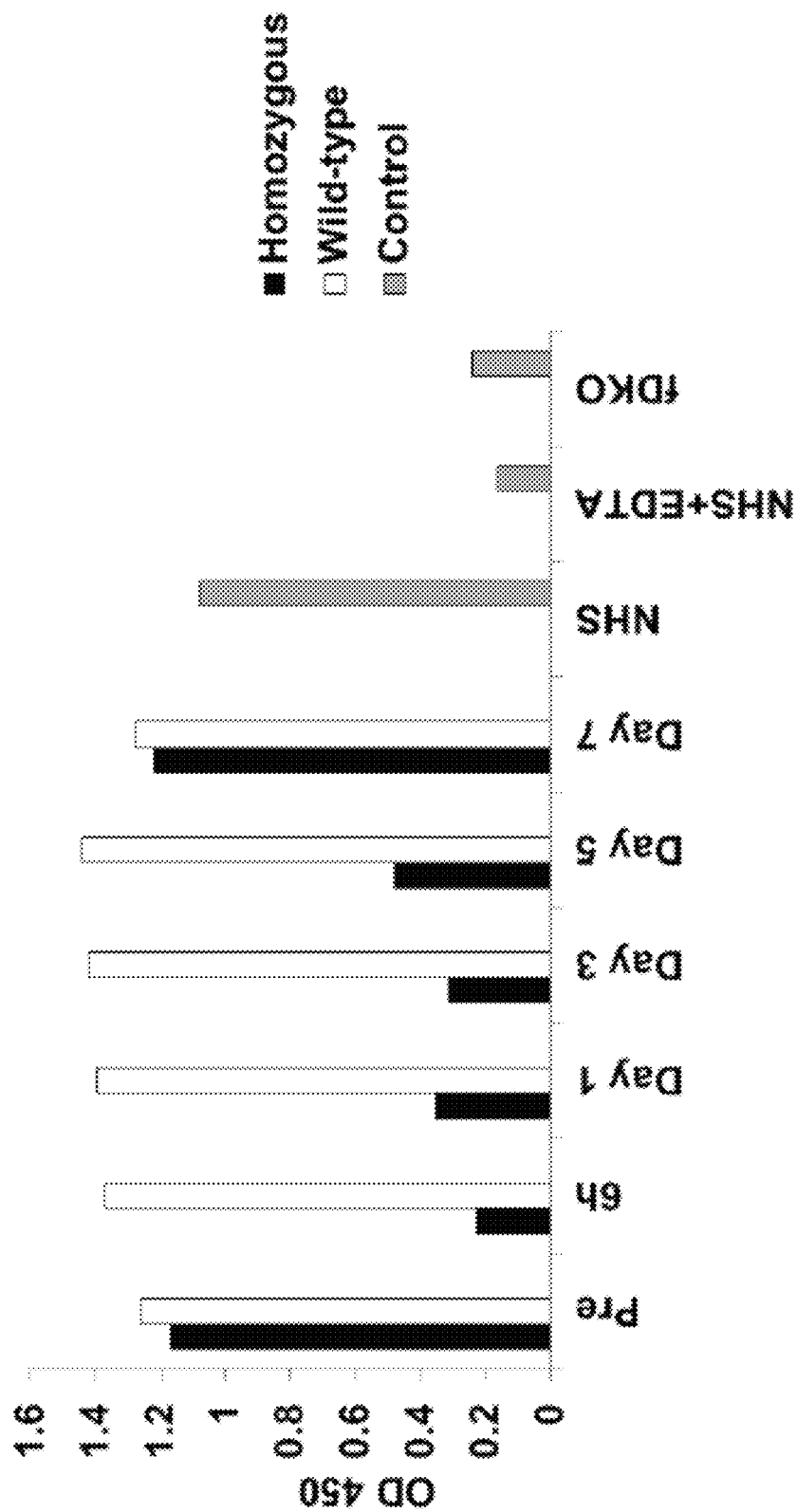
FIG. 14 depicts results of experiments evaluating in vivo activity and kinetics of mAb 11-81A in human factor D knock-in mice. A homozygous human factor D knock-in mouse was injected with 1 mg (i.p.) of mAb 11-8A1. Serum samples were collected before injection (0 hour) and then at various time points after injection and tested for LPS-induced AP complement activation. As shown, no AP complement activity was present in factor D knockout mouse serum or in NHS treated with EDTA. In contrast, AP complement activity was detected in NHS and in the serum of homozygous human factor D knock-in mouse at time 0 hour (before mAb treatment). AP complement activity in the homozygous human factor D knock-in mouse was inhibited at 6 hours and day 1-5 after mAb 11-8A1 treatment. AP complement activity returned to normal at day 7. These results suggested that at a dosage of 1 mg/mouse, mAb 11-8A1 was able to inhibit AP complement activity in vivo up to 3-5 days.
Figure 15:
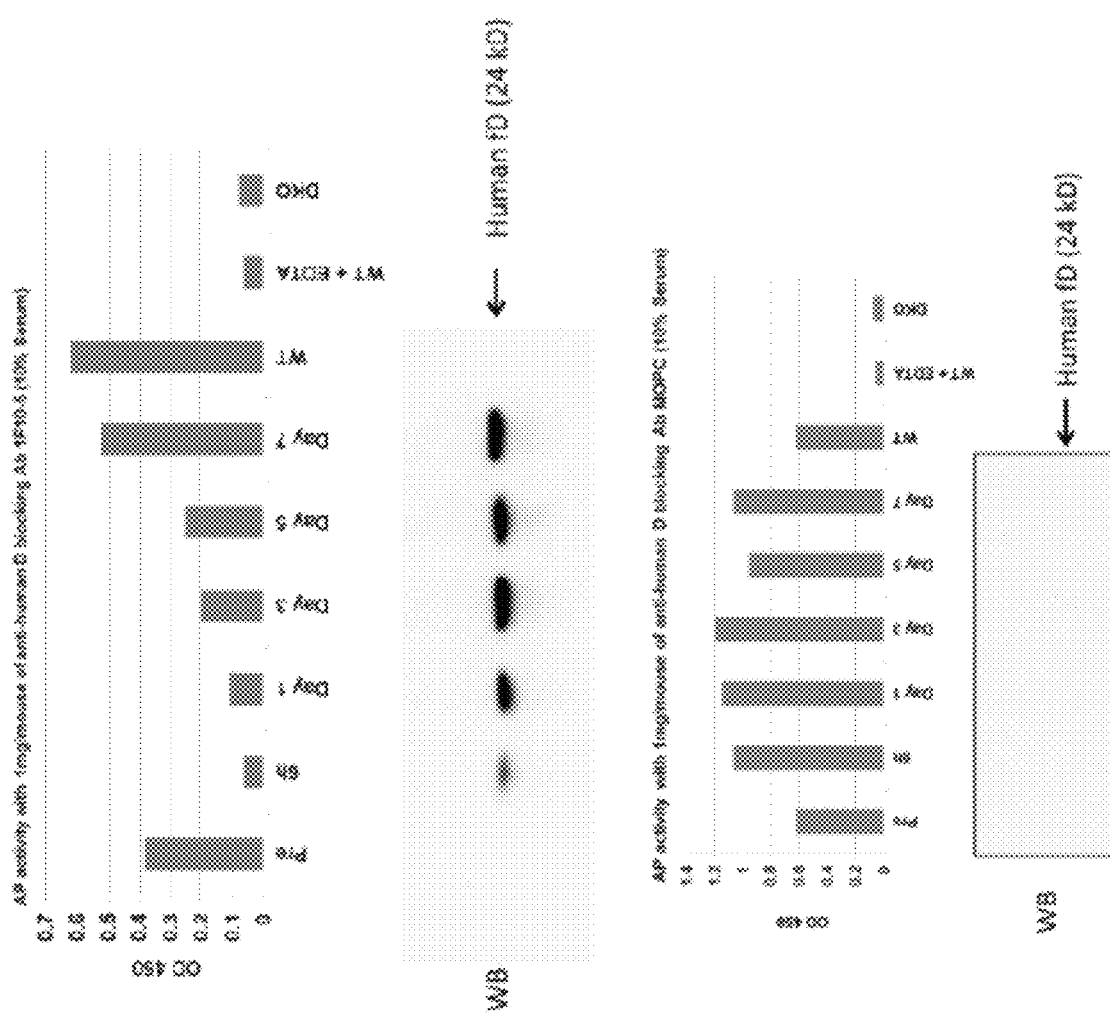
FIG. 15 depicts results from experiments evaluating in vivo activity and kinetics of mAb 1F10-5 and an irrelevant control mAb (MOPC) in human factor D knock-in mice. A homozygous human factor D knock-in (HDKI) mouse was injected with 1 mg (i.p.) of mAb 1F10-5 or an isotype-control mAb (MOPC, mouse IgG1). Serum samples were collected before injection (0 hour) and then at various time points after injection and tested for LPS-induced AP complement activation. Changes in levels of circulating human factor D in pre- and post-treatment serum samples were assessed by Western-blotting using a goat anti-human factor D polyclonal antibody. As shown, no AP complement activity was present in factor D knockout mouse (DKO) serum or in WT serum treated with EDTA. In contrast, AP complement activity was detected in WT serum and in the serum of homozygous HDKI mouse at time 0 hour (before mAb treatment). Following 1F10-5 mAb treatment, AP complement activity in the homozygous HDKI mouse was inhibited to various degrees between 6 hours and day 5. It returned to normal at day 7. These results suggested that mAb 1F10-5 was able to cause sustained inhibition of AP complement activity when given systemically. Western-blotting data showed accumulation of human factor D in blood due to formation of factor D/anti-factor D complexes. Free human factor D was excreted from the kidney and present in the urine of HDKI mice. The increase in blood levels of human factor D in HDKI mice suggested that factor D/anti-factor D complexes were prevented from excretion through the kidney. The isotype control mAb, MOPC, did not inhibit AP complement activity in a homozygous HDKI mouse, nor did it cause human factor D accumulation in blood.
Figure 16:
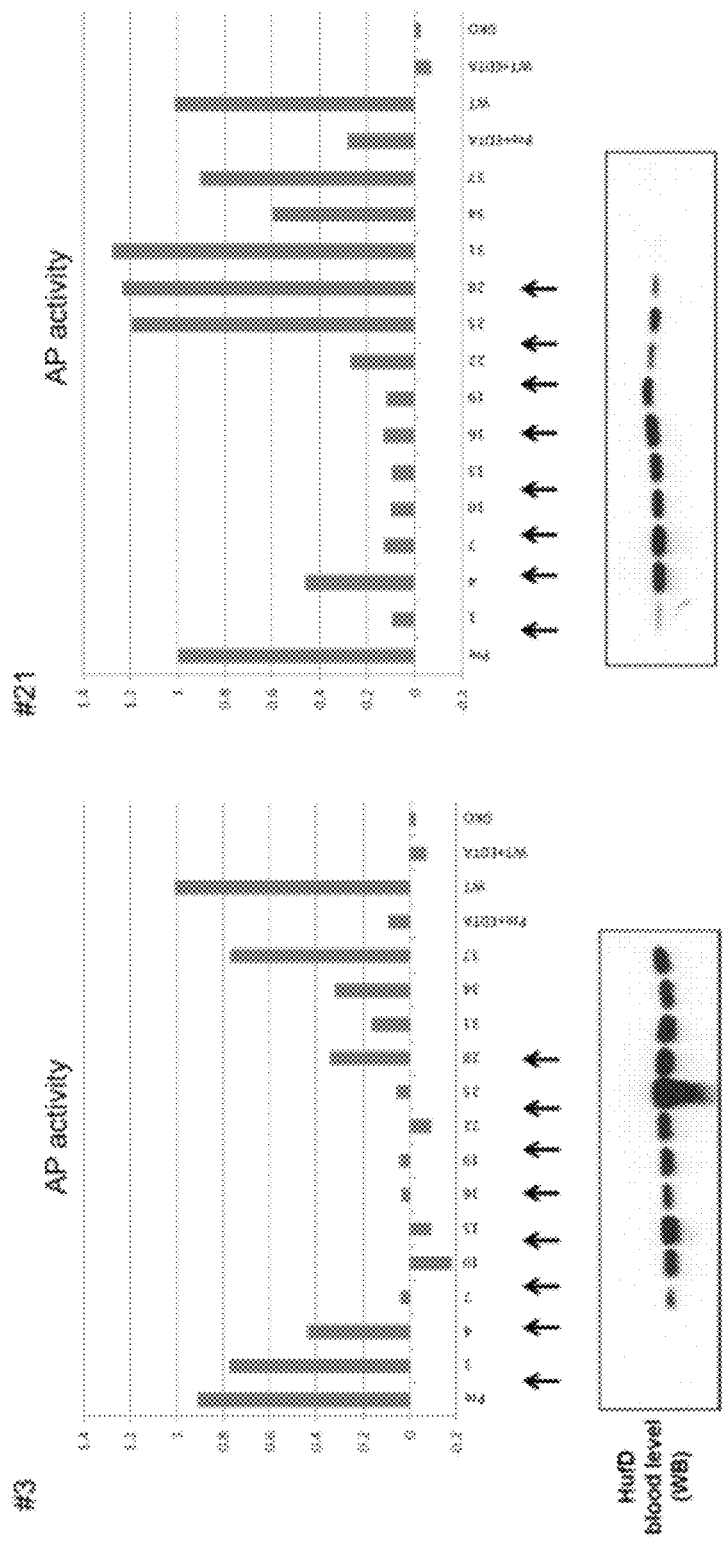
FIG. 16 depicts results from experiments evaluating in vivo activity and kinetics of mAb 11-8A1 in human factor D knock-in mice during long-term treatment. Continuous administration of 11A8-1 mAb to two homozygous human factor D knock-in (HDKI) mice (mouse ID #3 and #21, mAb was given every 4 days at 1 mg/mouse) caused sustained inhibition of AP complement activity over a 4-week period. As in previous single-dose experiment, mAb 118A-1 caused accumulation of human factor D in blood but factor D eventually reached a stead state level in both treated mice as determined by Western blot analysis. Together, these data showed that by administering an anti-factor D mAb to a subject at appropriate doses and frequencies, it is feasible to cause sustained inhibition of systemic AP complement activity.
Figure 17:
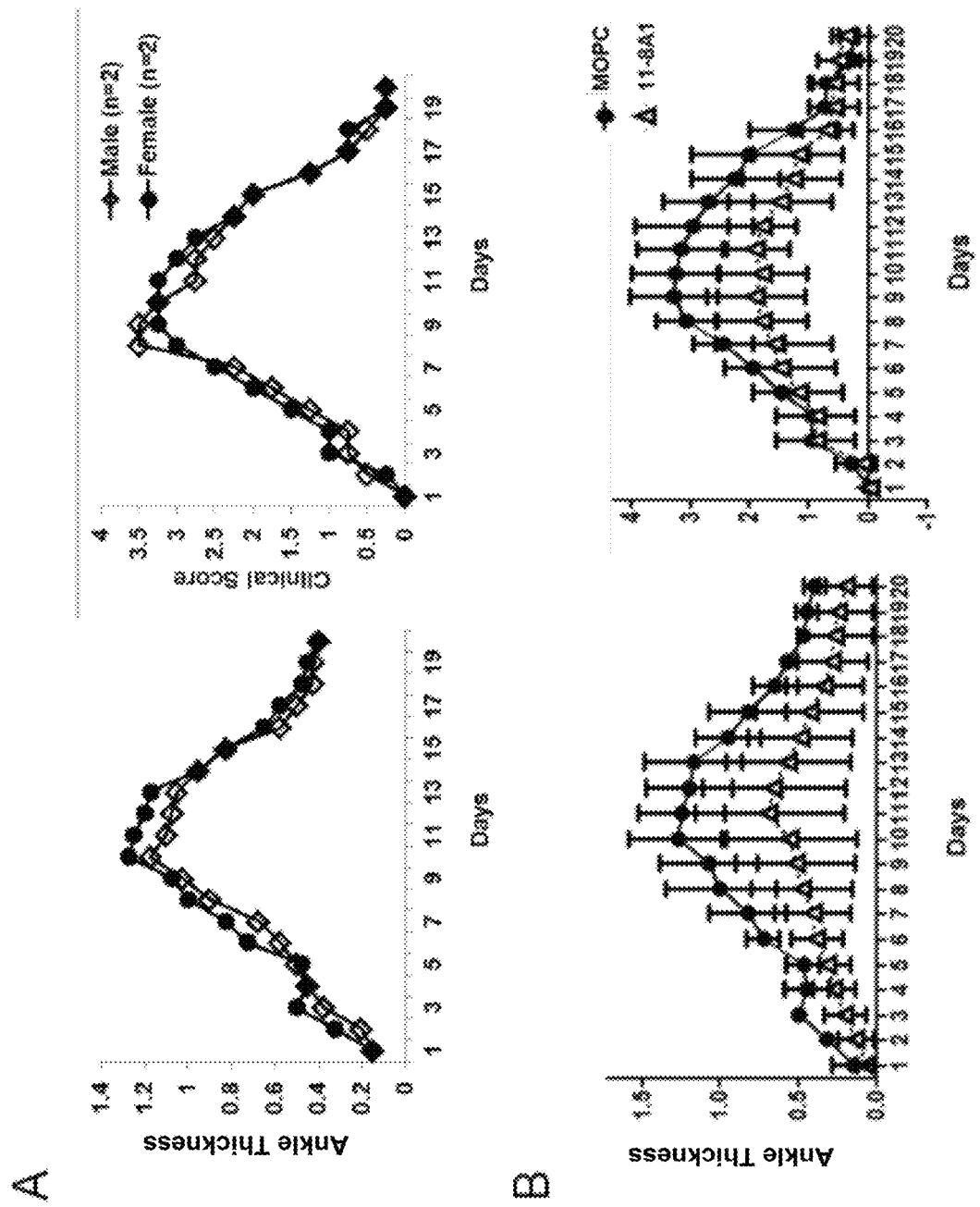
FIG. 17, comprising
Figure 18:
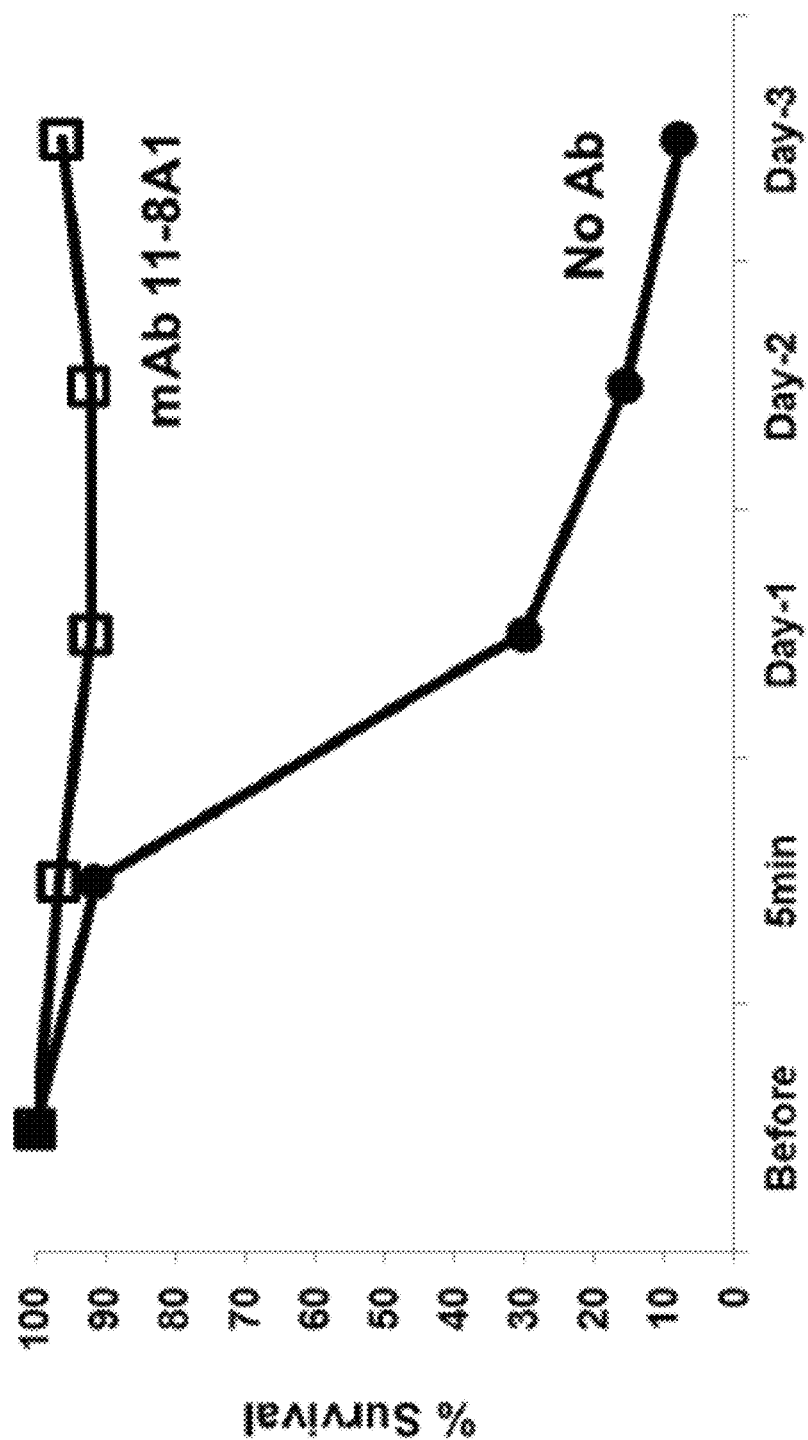
FIG. 18 depicts results from experiments assessing the therapeutic efficacy of mAb 11-8A1 in preventing extravascular hemolysis (EVH) using the human factor D knock-in mouse as a model. Homozygous human factor D knock-in (HDKI) mice were transfused with red blood cells (RBC) from wild-type and Crry/DAF/C3 triple knockout (TKO) mice. Recipient HDKI mice were treated 24 hours before RBC transfer with mAb 118A-1 (2 mg/mouse, i.p.) or PBS. A 1:1 mixture of DDAO-SE labeled WT and CFSE-labeled TKO red blood cells (RBCs) was injected into recipient mice through tail vein. At 5 minutes and day 1, 2 and 3 after RBC transfusion, recipient mice were bled and RBCs were analyzed to determine the percentage of the transfused RBCs remaining in the circulation. Number of CFSE-labeled TKO RBCs in each recipient was normalized (as %) to DDAO-SE-labeled WT RBCs at each time points. In recipient HDKI mice with no mAb treatment, TKO RBCs were rapidly eliminated through EVH, consistent with previous findings (Miwa et al., 2002, Blood 99: 3707-3716). However, in recipient HDKI mice treated with anti-human factor D mAb 11-8A1, no EVH occurred and the transfused TKO RBCs persisted. These results demonstrated that anti-human factor D mAb was effective in preventing EVH.

We used the pND1 plasmid to assemble the final targeting vector. For the short-arm homologous sequence, we amplified a 4.2-kb smaI-smaI fragment containing the 3'region of mouse factor D gene with the use of 5'-CCCGGGCTGGGTTTTGGTTTTTGC-3' (forward; SmaI site is underlined) and 5'-CCCGGGTCCTTGACAT-GAACACTTTGC-3' (reverse; SmaI site is underlined) as primers (SmaI sites are underlined). This fragment was cloned into the pND1 vector at KpnI sites treated with the Blunting reagent. For the long-arm homologous sequence, we amplified a 5.7-kb fragment containing the 5' region of the mouse factor D gene with the use of 5'-ATCGA-TACTCAGAAATCTGCCTGCCTC-3' (forward; ClaI site is underlined) and 5'-GCGGCCGCTCCTAG-GAGGACCAGAACTGCCAGGCGCTCCCAGCTGTG-CATTCTG ACAGCA-3' (reverse; NotI site underlined) as primers. We also amplified a 1.2-kb fragment containing the 3'region of mouse factor D gene with the use of 5'-CTCGAGAGAGACACGTGGCTCACAATA-3' (forward; XhoI site is underlined) and 5'-CTCGAGAAT-TATCGAAGTACTCCACCG-3' (reverse; XhoI site is underlined) as primers (SmaI sites are underlined). A 826 bp fragment containing the coding sequence of human factor D through Genscript Corp was synthesized, and isolated the 0.75 kb NotI-XhoI fragment by digesting with NotI and XhoI. These three fragments, the 5.7 kb ClaI-NotI fragment, the 0.75 kb NotI-XhoI fragment and the 1.2 kb XhoI-XhoI fragment were subcloned into the above pND1 vector at ClaI-XhoI sites. The targeting construct was linearized and electroporated into C57BL/6 ES cells and selected for neomycin resistance. Targeted ES clones were identified by Southern blotting using the 3' probe recognized a 5 kb wild-type fragment and a 4.5 kb fragment in the appropriately modified genomic region following BamHI digestion (FIG. 11 c). Correctly targeted ES clones were injected into blastocysts to generate chimeric mice. The resulting male chimeras were crossed with female C57BL/6 mice to determine germ line transmission of the targeted allele. Heterozygous human factor D knock-in mice were crossed with FLPe genetically modified mice (C57BL/6 background, Jackson laboratory) to remove the neo cassette from the human factor D knock-in allele. Heterozygous human factor D knock-in mice lacking the neo cassette were intercrossed to generate homozygous human factor D knock-in mice. We identified wild-type (WT), heterozygous (Het) and homozygous (Homo) human factor D knock-in mice by tail DNA PCR genotyping using specific to human factor D (target size: 450 bp) 5'-GTC AGG GTG CCA TGC AGG AG-3' (SEQ ID NO:26) and 5'-CCC AGG AGA ACC TGC ACC TTC-3' (SEQ ID NO:27), and specific to mouse factor D (target size: 292 bp) 5'-CCT CCC ACC CTT AGC TAT CC-3' (SEQ ID NO:28) and 5'-ACC CAG ACT GTG TCC CTC AC-3'(SEQ ID NO:29) (FIG. 11d).

Example 7

Experiments were conducted to examine the in vivo activity and kinetics of 11A8-1 and 1F10-5 mAbs in homozygous human factor D knock-in mice. The mice were injected with 1 mg (i.p.) of 11A8-1 mAb or 1F10-5 mAb. Blood samples (50-75 µl) were collected before injection (24 hour) and then at various time points after injection by retro-orbital bleeding and sera prepared. Serum samples were tested for LPS-induced AP complement activation. For this assay, ELISA plates (96-well, Nunc) were coated with 50 µl LPS solution (2 ug/well in PBS, 37° C., 1 hour). The plates were washed 3× with PBS containing 0.05% Tween-20 (PBS-T) and 50 µl serially diluted (starting from 1:10) mouse serum was added to each well. The mouse serum was diluted with GVB-EGTA-Mg++ (containing 10 mM EGTA and 2.5 mM Mg++ final concentration). The plate was left to incubate at 37° C. for 1 hour, washed 3× with PBS-T and then 50 µl HRP-conjugated goat anti-mouse C3 antibody (1:4000, Cappel) was added and the plate was left for 1 hour room temperature. The plate was washed for three times with PBS-T and then developed using BD Pharmingen A+B reagent. The reaction was stopped after 6-10 min with 2 N H2SO4. AP complement activation was detected by measuring the amount of C3 deposition on the plate (OD450).

Example 8

For generating deletion mutants, primers (Table 1) were designed such that the contact sites were deleted with forward and reverse primer. Substitution mutants are created by incorporating the desired nucleotide in forward primer. 20 ng of pCMV-XL4-hfD plasmid was amplified with respective forward and reverse primers using Q5® Hot Start High-Fidelity master mix. The amplified products were run on agarose gel electrophoresis to confirm purity. The corresponding amplified products were excised from the agarose gel and DNA was extracted using Bioneer gel purification kit. The purified DNA was ligated with DNA ligase (Takara DNA ligase mix) and transformed into JM109 competent cells and 100 µl was spread on LB agar ampicillin (50 µg/ml) plate. Colonies were picked up and inoculated in LB medium containing 75 ug/ml ampicillin. Plasmids were isolated and insert release was confirmed by digesting with NotI restriction enzyme. The restriction positive plasmids were sequenced for deletion and substitution mutants. The deletion and substitution positive mutant plasmids were used for expression of the deletion protein by transfection.

TABLE 1

| SEQ ID NO | | Deletion | Primer (5'-3') | | Position in mRNA | Length |
|---|---|---|---|---|---|---|
| SEQ ID NO: 30/31 | Deletions | Δ1 (P107-W110) | For | CAGCGCGTGGACCGCGACGT | 431-450 | 20 |
| | | | Rev | GCGCACAGCAGGGCCCAGTG | 399-418 | 20 |
| SEQ ID NO: 32/33 | | Δ2 (I130-A134) | For | GGCCGCCGCCCGGACAGCCT | 503-522 | 20 |
| | | | Rev | GCCCCAGCCGGCCACGTCGCA | 467-487 | 21 |
| SEQ ID NO: 34/35 | | Δ3 (V148-R151) | For | GCCACCTGCAACCGGCGCACG | 554-574 | 21 |
| | | | Rev | TGGCAAGAGCACGTGCTGCAGGC | 519-541 | 23 |
| SEQ ID NO: 36/37 | | Δ4 (S178-G184) | For | GGCCCGCTGGTGTGCGGG | 653-670 | 18 |
| | | | Rev | GTCCCGGCGATTGCTCTCCGC | 611-631 | 21 |
| SEQ ID NO: 38/39 | | Δ12 (P107-A134) | For | GGCCGCCGCCCGGACAGCCT | 503-522 | 20 |
| | | | Rev | GCGCACAGCAGGGCCCAGTG | 399-418 | 20 |
| SEQ ID NO: 40/41 | | Δ13 (P107-R151) | For | GCCACCTGCAACCGGCGCACG | 554-574 | 21 |
| | | | Rev | GCGCACAGCAGGGCCCAGTG | 399-418 | 20 |
| SEQ ID NO: 42/43 | | Δ14 (P107-G184) | For | GGCCCGCTGGTGTGCGGG | 653-670 | 18 |
| | | | Rev | GCGCACAGCAGGGCCCAGTG | 399-418 | 20 |
| SEQ ID NO: 44/45 | | Δ23 (I130-R151) | For | GCCACCTGCAACCGGCGCACG | 554-574 | 21 |
| | | | Rev | GCCCCAGCCGGCCACGTCGCA | 467-487 | 21 |
| SEQ ID NO: 46/47 | | Δ34 (V148-G184) | For | GGCCCGCTGGTGTGCGGG | 653-670 | 18 |
| | | | Rev | GTCCCGGCGATTGCTCTCCGC | 611-631 | 21 |
| SEQ ID NO: 48/49 | Mutations | P107A | For | TGCTGTGCGCgccCTGCCCTGGC | 409-431 | 23 |
| | | | Rev | GGGCCCAGTGTGGCCTTCTCCG | 387-408 | 22 |
| SEQ ID NO: 50/51 | | L108A | For | TGTGCGCCCCgccCCCTGGCAGCG | 412-435 | 24 |
| | | | Rev | GCAGGGCCCAGTGTGGCC | 394-411 | 18 |
| SEQ ID NO: 52/53 | | P109A | For | GCGCCCCCTGgccTGGCAGCGCG | 415-437 | 23 |
| | | | Rev | ACAGCAGGGCCCAGTGTGGCCTTCTCC | 388-414 | 27 |
| SEQ ID NO: 54/55 | | W110A | For | CCCCCTGCCCgccCAGCGCGTGG | 418-440 | 23 |
| | | | Rev | CGCACAGCAGGGCCCAGT | 400-417 | 18 |
| SEQ ID NO: 56/57 | | V148A | For | GCTCTTGCCAgccCTGGACCGCG | 532-554 | 23 |
| | | | Rev | ACGTGCTGCAGGCTGTCC | 514-531 | 18 |

TABLE 1-continued

| SEQ ID NO | Deletion | | Primer (5'-3') | Position in mRNA | Length |
|---|---|---|---|---|---|
| SEQ ID NO: 58/59 | L149A | For | CTTGCCAGTGgccGACCGCGCCACC | 535-559 | 25 |
| | | Rev | AGCACGTGCTGCAGGCTG | 517-534 | 18 |
| SEQ ID NO: 60/61 | D150A | For | GCCAGTGCTGgccCGCGCCACCT | 538-560 | 23 |
| | | Rev | AAGAGCACGTGCTGCAGGCTGTC | 515-537 | 23 |
| SEQ ID NO: 62/63 | R151A | For | AGTGCTGGACgccGCCACCTGCAAC | 541-565 | 25 |
| | | Rev | GGCAAGAGCACGTGCTGC | 523-540 | 18 |
| SEQ ID NO: 64/65 | P107A-W110A | For | gccgccCAGCGCGTGGACCGCGAC | 425-448 | 24 |
| | | Rev | ggcggcGCGCACAGCAGGGCCCAG | 401-424 | 24 |
| SEQ ID NO: 66/67 | V148A-R151A | For | gccgccGCCACCTGCAACCGGCGC | 548-571 | 24 |
| | | Rev | ggcggcTGGCAAGAGCACGTGCTGC | 523-547 | 25 |
| SEQ ID NO: 68/69 | R156L-H158Y | For | CCTGCGCAGCTACCACGACGGCG | 565-587 | 23 |
| | | Rev | TTGCAGGTGGCGCGGTCCAGC | 544-564 | 21 |
| SEQ ID NO: 70/71 | L168M | For | CACCGAGCGCatgATGTGCGCGG | 592-614 | 23 |
| | | Rev | ATGGCGCCGTCGTGGTAC | 574-591 | 18 |

Example 9

Endotoxin free plasmids were used for transfection. Chinese hamster ovary (CHO) cells were allowed to grow in 6 well plates up to 85-90% confluence. Positive control and deletion mutant plasmids were transfected with lipofectamine (Invitrogen) with 1:2 ratio in Opti-MEM (Thermo Fisher Scientific). After 48 hours of transfection, supernatant was collected and stored at −200 C until use. Cells were washed with ice cold PBS (Invitrogen) and Non-denaturing RIPA (Radioimmunoprecipitation assay) buffer (20 mM Tris HCl pH 8, 137 mM NaCl, 1% NP-40, 2 mM EDTA) was added and kept on ice for 30 min with occasional shaking. Cell lysate was collected after centrifugation and supernatant was stored at −200 C. CHO cell supernatant and cell lysate was used as negative control.

Example 10

Epitope mapping of 11A8-1 was done by Immuno-precipitation and western blotting method. 300 mg of CNBr-activated sepharose beads 4B (Cat #17-0430-1 GE healthcare) were allowed to swell in 1 mM HCl for 15 min. The beads were then transferred to sintered glass funnel and washed with 200 ml of 1 mM HCl. The gel (beads) were washed with coupling buffer pH 9.0 (0.1 M NaHCO3-pH 9.0, 0.5 M NaCl) and immediately transferred to a tube containing 1 mg of 11-8A1 antibody in coupling buffer within 5 min. The tube was kept on rotating platform for overnight at 40 C. Coupling of antibody to CNBr beads was checked by measuring the absorbance of antibody solution before and after coupling. Excess ligand was washed away by washing with coupling buffer for 3 times and remaining active sites were blocked with blocking buffer (1 M Tris-base, pH 9.0) for 2 hours at room temperature. To remove excess of uncoupled ligand after coupling, beads were washed alternatively with low pH (0.1 M acetic acid, 0.5 M NaCl) and high pH (coupling buffer) wash buffer for 2 times. 200 μl of coupled beads was incubated with transfection supernatants and cell lysate for 2 hours at room temperature on rotating platform. Beads were washed with 0.5 M NaCl in PBS for 5 times. Proteins were eluted with antibody elution buffer (0.1 M glycine, pH 2.0) and neutralized with 1.5 M Tris, pH 9.0. 50 μl of eluted samples was used for immunoblotting.

Example 11

Epitope mapping of 1F10-5 was done by ELISA method. Microtiter plates were coated with 1F10-5 (2 μg/ml) in PBS at 37° C. for 1 hour. After aspirating the antibody solution, wells were blocked with PBS containing 1% BSA in PBS at room temperature for 1 hour. Cell culture supernatants from transient CHO transfectants of full or four deletion mutants (mutant-9, 10, 11 or 12) of human factor D were added to the wells. Blank is cell culture medium from non-transfected cells. Following 1 hour incubation at room temperature, the wells were extensively washed. 1F10-5 bound human factor D was detected by using biotin-conjugated goat-anti-human factor D antibody following HRP-conjugated streptavidin. After washing, the plate was developed with HRP substrate for 6-10 minutes. The reaction was stopped with 2N H2SO4 and plate was read at 450 nm in a micro plate reader.

For epitope mapping, mAb 1F10-5 was tested for reactivity with full and four deletion mutants of human factor D. Western-blotting confirmed protein expression for four deletion mutants. In ELISA, mAb 1F10-5 bound Full, mutant-9 and -12, but its binding to mutant-10 and -11 was greatly reduced. These results, shown in FIG. 19, suggest that deletion of five amino acids of NRRTH at 155-159 (SEQ ID NO: 23) or four amino acids SNRR at 173-176 (SEQ ID NO: 24) disrupted binding by mAb 1F10-5, and that the epitope of mAb 1F-10 includes amino acids SNRR.

Example 12

Homozygous human factor D knock-in mice were transfused with red blood cells (RBC) from wild-type and Crry/DAF/C3 triple knockout (TKO) mice. Recipient mice (homozygous human factor D knock-in mice) were treated 24 hours before RBC transfer with mAb 118A-1 (2 mg/mouse, i.p.) or PBS. Donor RBCs were harvested from TKO mice, washed in PBS and labeled with CFSE according to previously published procedure (Miwa et al., 2002, Blood 99; 3707-3716). Similarly, donor RBCs were also harvested from wild-type (C57BL/6J) mice, washed in PBS and labeled with DDAO-SE (Thermo Fisher Scientific) according to manufacturer's instructions. A 1:1 mixture of WT and TKO RBCs equivalent to 200 μl of blood was injected into recipient mice through tail vein. At 5 minutes and 6, 24, 48, 72, 96, 120 hours after RBC transfusion, recipient mice were bled and RBCs were analyzed to determine the percentage of CFSE- or DDAO-SE-labeled (i.e. transfused) RBCs remaining in the circulation. Number of CFSE-labeled TKO RBCs in each recipient was normalized (as %) to DDAO-SE-labeled WT RBCs at each time points.

Example 13

Arthritis was induced in homozygous human factor D knock-in mice by passive transfer of purified total IgGs from K/BxN mice (2 mg/mouse, i.p. at days 0 and 2). Ankle thickening was measured by a caliper (Mitutoyo), and clinical scores were recorded using previously published criteria (Kimura et al., 2010, JCI; 3545-3554). The mice were treated with 1 mg of 11A8-1 at day −1, day 3, 7, 11 and 15.

Example 14

Figure 20:
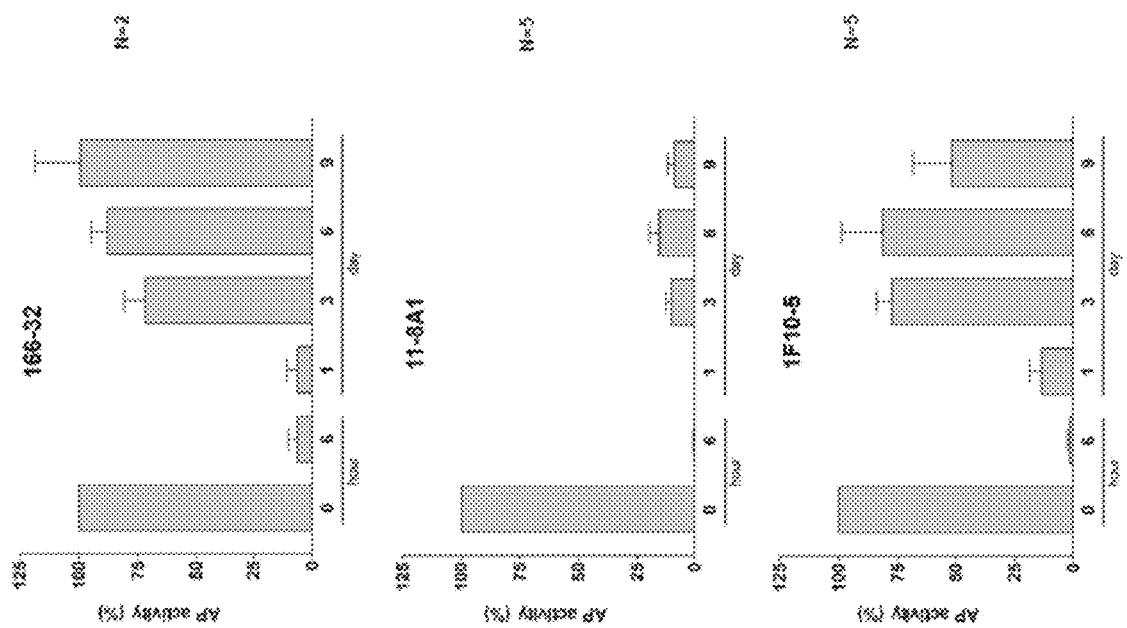
FIG. 20 depicts the results of exemplary experiments assessing the in vivo activity of mAb 11-8A1, 1F10-5 and 166-32 in human factor D knock-in mice. To evaluate the efficacy of 166-32 (see Tanox U.S. Pat. No. 8,124,090), 11-8A1, and 1F10-5 mAb in blocking alternative pathway (AP) complement activity in vivo, factor D humanized mice were treated by repeated dosing (1 mg/mouse, every 3 days, s.c. administration). Plasma samples were collected before mAb treatment (time 0) and 6 hr, 1, 3, 6 and 9 days after mAb treatment and tested for LPS-induced AP complement activity. AP complement activity at various time points was normalized to 100% of the values obtained at time 0. The data showed that mAb 11-8A1 and 1F10-5 had superior pharmacodynamics activity in vivo as compared with mAb 166-32. Specifically, mAb 11-8A1 consistently inhibited 80-90% AP complement activity at all time times after mAb administration, whereas mAb 166-32 achieved comparable inhibition only at 6 hr and day 1 after mAb administration. mAb 1F10-5 showed 50% inhibition of AP complement at day 9 whereas almost inhibition of AP complement activity by mAb 166-32 was observed at day 9.

In vivo activity of mAb 11-8A1, 1F10-5 and 166-32 was assessed in human factor D knock-in mice. To evaluate the efficacy of 166-32 (see Tanox U.S. Pat. No. 8,124,090), 11-8A1, and 1F10-5 mAb in blocking alternative pathway (AP) complement activity in vivo, factor D humanized mice were treated by repeated dosing (1 mg/mouse, every 3 days, s.c. administration). Plasma samples were collected before mAb treatment (time 0) and 6 hr, 1, 3, 6 and 9 days after mAb treatment and tested for LPS-induced AP complement activity. AP complement activity at various time points was normalized to 100% of the values obtained at time 0. The data showed that mAb 11-8A1 and 1F10-5 had superior pharmacodynamics activity in vivo as compared with mAb 166-32 (FIG. 20). Specifically, mAb 11-8A1 consistently inhibited 80-90% AP complement activity at all time times after mAb administration, whereas mAb 166-32 achieved comparable inhibition only at 6 hr and day 1 after mAb administration. mAb 1F10-5 showed 50% inhibition of AP complement at day 9 whereas almost inhibition of AP complement activity by mAb 166-32 was observed at day 9 (FIG. 20).

Figure 21:
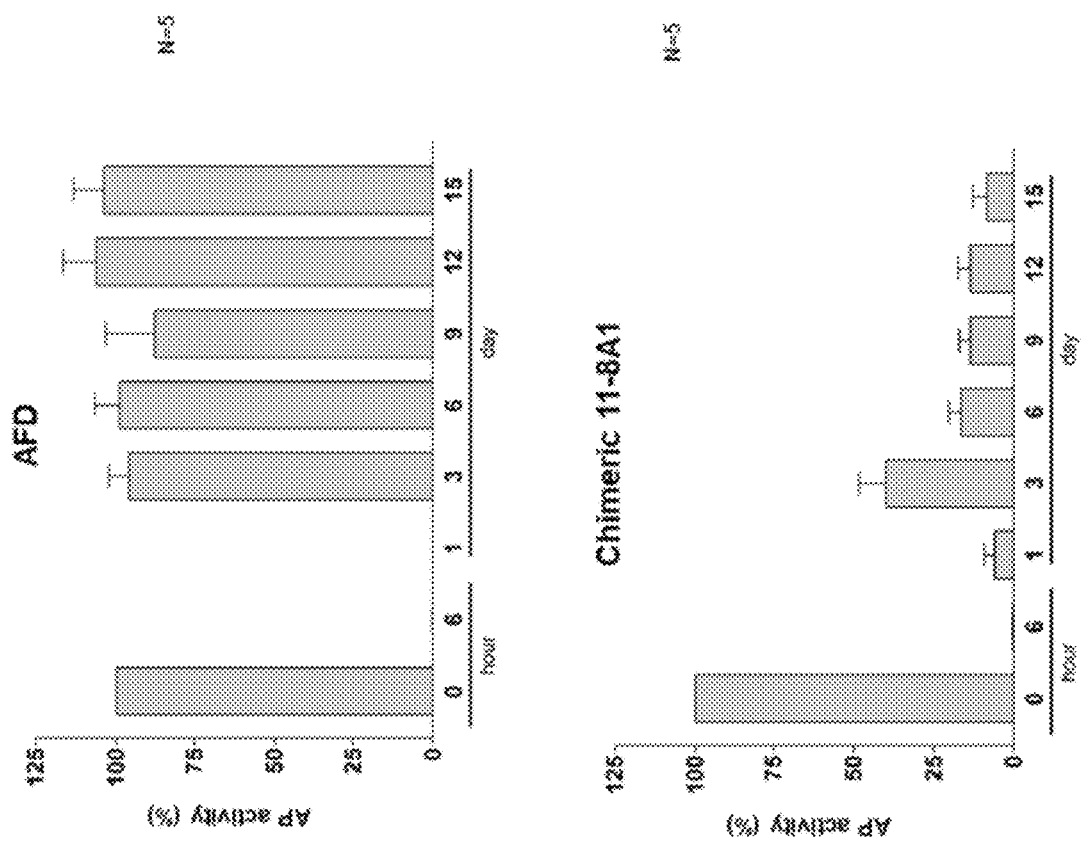
FIG. 21 depicts the results of exemplary experiments assessing the in vivo activity of chimeric 11-8A1 mAb and chimeric AFD in human factor D knock-in mice. To evaluate the efficacy of a 11-8A1/human IgG4 chimeric mAb and AFD/human IgG4 chimeric mAb in blocking alternative pathway (AP) complement activity in vivo, factor D humanized mice were treated by repeated dosing (1 mg/mouse, every 3 days, s.c. administration). Plasma samples were collected before mAb treatment (time 0) and 6 hr, 1, 3, 6, 9, 12 and 15 days after mAb treatment and tested for LPS-induced AP complement activity. AP complement activity at various time points was normalized to 100% of the values obtained at time 0. AFD is a humanized version of mAb 166-32 (see Katschke et al., J Biol Chem. 2012 Apr. 13; 287:12886-12892, WO/2008/055206, U.S. Pat. Nos. 8,372,403, 8,273,352, U.S. Pat. App. No. 2014/0212433). The data showed that 11-8A1/human IgG4 chimeric mAb was far more potent and displayed a far better pharmacodynamics profile than AFD/human IgG4 chimeric mAb. Specifically, while both mAbs caused 90-100% inhibition at 6 hr and day 1 after mAb administration, 11-8A1/human IgG4 chimera mAb, but not AFD/human IgG4 chimeric mAb, caused greater than 75% inhibition of AP complement activity on day 6-15.

In vivo activity of chimeric 11-8A1 mAb and chimeric AFD was assessed in human factor D knock-in mice. To evaluate the efficacy of a 11-8A1/human IgG4 chimeric mAb and AFD/human IgG4 chimeric mAb in blocking alternative pathway (AP) complement activity in vivo, factor D humanized mice were treated by repeated dosing (1 mg/mouse, every 3 days, s.c. administration). Plasma samples were collected before mAb treatment (time 0) and 6 hr, 1, 3, 6, 9, 12 and 15 days after mAb treatment and tested for LPS-induced AP complement activity. AP complement activity at various time points was normalized to 100% of the values obtained at time 0. AFD is a humanized version of mAb 166-32 (see Katschke et al., J Biol Chem. 2012 Apr. 13; 287:12886-12892, WO/2008/055206, U.S. Pat. Nos. 8,372,403, 8,273,352, U.S. Pat. App. No. 2014/0212433). The data showed that 11-8A1/human IgG4 chimeric mAb was far more potent and displayed a far better pharmacodynamics profile than AFD/human IgG4 chimeric mAb (FIG. 21). Specifically, while both mAbs caused 90-100% inhibition at 6 hr and day 1 after mAb administration, 11-8A1/human IgG4 chimera mAb, but not AFD/human IgG4 chimeric mAb, caused greater than 75% inhibition of AP complement activity on day 6-15 (FIG. 21).

The materials and methods used in this example are now described.

Purification of 166-32 mAb

To prepare purified 166-32 mAb, the murine hybridoma cells (HB124-76) that secretes the monoclonal antibody 166-322 that binds to human factor D was obtained from ATCC (see Tanox U.S. Pat. No. 8,124,090), and cultured. Cell culture medium was collected for mAb purification by protein G affinity chromatography.

Preparation of 11-8A1/Human IgG4 Chimeric mAb

To clone the cDNAs of mAb 11-8A1, total RNA was isolated from the hybridoma cells by TRizol reagent (Sigma). First-strand cDNAs were synthesized by reverse transcription using Oligo(dT) primer, To amplify the heavy chain cDNAs (for IgG1, IgG2a/b), the following primers were used in PCR reactions: 5'-GAGGTGAAGCTGGTG-GAG(T/A)C(T/A) GG-3' SEQ ID NO:72 and 5'-GGGGCCAGTGGATAGAC-3' SEQ ID NO:73. To amplify the kappa light chain, the following primers were used: mixture of 4 upstream primers: 5'-CCAGTTCCGAGCTCCAGATGACCCAGACTCCA-3' SEQ ID NO:74; 5'-CCAGTTCCGAGCTCGTGCT-CACCCAGTCTCCA-3' SEQ ID NO:75; 5'-CCAGTTCCGAGCTCCAGATGACCCAGTCTCCA-3' SEQ ID NO:76; 5'-CCAGTTCCGAGCTCGT-GATGACACAGTCTCCA-3' SEQ ID NO:77; downstream primer: 5'-GTTGGTGCAGCATCAGC-3' SEQ ID NO:78. The PCR amplicons were cloned into pCR TOPO TA 2.1 vector (Invitrogen) and sequenced. To obtain the signal peptide (leader) sequence of the mAbs, the 5'-RACE method was used with a kit (GeneRacer) from Invitrogen. The complete variable region cDNAs were amplified using specific primers determined from the 5'-RACE and the initial sequencing data. cDNAs encoding the heavy-chain and light-chain variable domains of mAb 11-8A1 were subcloned into the pFUSE-CHIg-hG4 and pFUSE2-CLIg-hk vectors (InVivoGen, San Diego, Calif.), respectively. In order to prevent exchange of IgG4 molecules, a S228P mutation was introduced into the Fc domain of 11-8A1/human IgG4 chimeric mAb. Recombinant 11-8A1/human IgG4 chimera was expressed in ExpiCHO Expression System (Thermo Fisher Scientific). Cell culture medium was collected for chimeric mAb purification by protein G affinity chromatography.

Preparation of Humanized 166-32 (AFD) Ab cDNAs encoding the heavy-chain and light-chain variable domains of AFD (see Katschke et al., J Biol Chem. 2012 Apr. 13; 287:12886-12892, WO/2008/055206, U.S. Pat. Nos. 8,372,403, 8,273,352, U.S. Pat. App. No. 2014/0212433) were synthesized and cloned into the pFUSE-CHIg-hG4 and pFUSE2-CLIg-hk vectors (InVivoGen, San Diego, Calif.), respectively. To prevent exchange of IgG4 molecules, a S228P mutation was introduced into the Fc domain of AFD/human IgG4 chimeric mAb. Recombinant AFD/human IgG4 mAb was expressed in ExpiCHO Expression System (Thermo Fisher Scientific). Cell culture medium was collected for chimeric mAb purification by protein G affinity chromatography.

Assessment of mAb Pharmacodynamics in Homozygous Human Factor D Knock-in Mice

Experiments were conducted to examine and compare the in vivo activity of murine 11-8A1, 1F10-5, 166-32 and 11-8A1/human IgG 4 chimera and AFD/human IgG4 chimera mAbs in homozygous human factor D knock-in mice.

Mice (10-12 weeks old) were injected with 1 mg/mouse (s.c. in PBS) of mAb every 3 days. Lepirudin anti-coagulated plasma samples (50-75 μl) were collected before injection (time 0) and then at various time points after injection by retro-orbital bleeding and plasma prepared. The plasma samples were frozen in −80° C. and stored until being tested in an ELISA-based LPS-induced AP complement activation assay. AP complement activation was evaluated by measuring the amount of activated C3 fragments deposition on the plate (OD450) as described (see Kimura et al., 2008, Blood 111:732-40.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antibody that specifically binds to human factor D, wherein the antibody is selected from the group consisting of:
   a) an antibody comprising a heavy chain variable (VH) region and a light chain variable (VL) region, wherein the VH region comprises:
      i) a VH-CDR1 comprising the amino acid sequence of SEQ ID NO:3;
      ii) a VH-CDR2 comprising the amino acid sequence of SEQ ID NO:4; and
      iii) a VH-CDR3 comprising the amino acid sequence of SEQ ID NO:5; and
   wherein the VL region comprises:
      i) a VL-CDR1 comprising the amino acid sequence of SEQ ID NO: 8;
      ii) a VL-CDR2 comprising the amino acid sequence of SEQ ID NO: 9; and
      iii) a VL-CDR3 comprising the amino acid sequence of SEQ ID NO: 10; and
   b) an antibody comprising a heavy chain variable (VH) region and a light chain variable (VL) region, wherein the VH region comprises:
      i) a VH-CDR1 comprising the amino acid sequence of SEQ ID NO:13;
      ii) a VH-CDR2 comprising the amino acid sequence of SEQ ID NO:14; and
      iii) a VH-CDR3 comprising the amino acid sequence of SEQ ID NO:15; and
   wherein the VL region comprises:
      i) a VL-CDR1 comprising the amino acid sequence of SEQ ID NO: 18;
      ii) a VL-CDR2 comprising the amino acid sequence of SEQ ID NO: 19; and
      iii) a VL-CDR3 comprising the amino acid sequence of SEQ ID NO: 20.

2. The antibody of claim 1, wherein the antibody comprises the CDRs: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10.

3. The antibody of claim 1, wherein the antibody comprises the CDRs: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20.

4. The antibody of claim 1, wherein the antibody comprises a heavy chain comprising an amino acid sequence having at least 95% identity to SEQ ID NO:2.

5. The antibody of claim 1, wherein the antibody comprises a light chain comprising an amino acid sequence having at least 95% identity to SEQ ID NO:7.

6. The antibody of claim 1, wherein the antibody comprises a heavy chain comprising an amino acid sequence having at least 95% identity to SEQ ID NO:2, and a light chain comprising an amino acid sequence having at least 95% identity to SEQ ID NO:7.

7. The antibody of claim 1, wherein the antibody comprises a heavy chain comprising an amino acid sequence having at least 95% identity to SEQ ID NO:12.

8. The antibody of claim 1, wherein the antibody comprises a light chain comprising an amino acid sequence having at least 95% identity to SEQ ID NO:17.

9. The antibody of claim 1, wherein the antibody comprises a heavy chain comprising an amino acid sequence having at least 95% identity to SEQ ID NO:12, and a light chain comprising an amino acid sequence having at least 95% identity to SEQ ID NO:17.

10. The antibody of claim 1, wherein the antibody binds to an epitope comprising at least one amino acid within at least one amino acid sequence of factor D selected from the group consisting an amino acid sequence having at least 95% identity to SEQ ID NO:21, amino acid sequence having at least 95% identity to SEQ ID NO:22, amino acid sequence having at least 95% identity to SEQ ID NO:23, and amino acid sequence having at least 95% identity to SEQ ID NO:24.

11. The antibody of claim 1, wherein the antibody binds to an epitope of human factor D having an amino acid sequence comprising at least one selected from the group consisting of SEQ ID NO: 21, SEQ ID NO: 22, SEQ ID NO: 23, and SEQ ID NO: 24.

12. A cell comprising the antibody of claim 1.

13. A cell comprising a nucleic acid encoding the antibody of claim 1.

14. A method of reducing the activity of an alternative pathway of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences:
  a) SEQ ID NO: 3, SEQ ID NO: 4, SEQ ID NO: 5, SEQ ID NO: 8, SEQ ID NO: 9, and SEQ ID NO: 10, or
  b) SEQ ID NO: 13, SEQ ID NO: 14, SEQ ID NO: 15, SEQ ID NO: 18, SEQ ID NO: 19, and SEQ ID NO: 20.

15. A method of treating an alternative pathway (AP)-mediated disease or disorder in an individual, comprising the step of administering to said individual the anti-factor D antibody of claim 1.

16. The method of claim 15, wherein the disease or disorder is at least selected from the group consisting of: macular degeneration (MD), age-related macular degeneration (AMD), ischemia reperfusion injury, arthritis, rheumatoid arthritis, asthma, allergic asthma, paroxysmal nocturnal hemoglobinuria (PNH) syndrome, atypical hemolytic uremic (aHUS) syndrome, epidermolysis bullosa, sepsis, organ transplantation, inflammation, inflammation associated with cardiopulmonary bypass surgery and kidney dialysis, C3 glomerulopathy, membranous nephropathy, glomerulonephritis, anti-neutrophil cytoplasmic antibody (ANCA)-mediated glomerulonephritis, lupus, ANCA-mediated vasculitis, Shiga toxin induced HUS, and antiphospholipid antibody-induced pregnancy loss, and combinations thereof.

\* \* \* \* \*

SEQUENCE LISTING

<160> NUMBER OF SEQ ID NOS: 78

<210> SEQ ID NO 1
<211> LENGTH: 449
<212> TYPE: DNA
<213> ORGANISM: Homo sapiens

<400> SEQUENCE: 1

```
ctcaaggtcc ttacaatgaa atgcagctgg gttatcgtct tcctgatggc agtggttaca      60
ggggtcaatt cagaggttca gctgcagcag tctggggcag accttgtgag gccagggcc     120 tcagtcaagt tgtcctgcac aacttctggc ttcaacatta agacaccta tgtgcactgg     180 gtgaaacaga ggcctgaaca gggcctggaa tggattggaa ggattgatcc tgcgaatggt     240
cttactacat tgatccgag gttccaggcc aaggccacta taacagcaga cacatcctcc     300
aataccgcct acctgcagct cagcagcctg acatctgagg acactgccgt ctattactgt     360
acatatgcta tggaatattg gggtcaagga acctcagtca ccgtctcctc agccaaaacg     420 acaccccat ctgtctatcc actggcccc                                       449
```

<210> SEQ ID NO 2
<211> LENGTH: 149
<212> TYPE: PRT
<213> ORGANISM: Homo sapiens

<400> SEQUENCE: 2

```
Leu Lys Val Leu Thr Met Lys Cys Ser Trp Val Ile Val Phe Leu Met
1               5                   10                  15

Ala Val Val Thr Gly Val Asn Ser Glu Val Gln Leu Gln Gln Ser Gly
                20                  25                  30

Ala Asp Leu Val Arg Pro Gly Ala Ser Val Lys Leu Ser Cys Thr Thr
            35                  40                  45

Ser Gly Phe Asn Ile Lys Asp Thr Tyr Val His Trp Val Lys Gln Arg
        50                  55                  60

Pro Glu Gln Gly Leu Glu Trp Ile Gly Arg Ile Asp Pro Ala Asn Gly
65                  70                  75                  80

Leu Thr Thr Phe Asp Pro Arg Phe Gln Ala Lys Ala Thr Ile Thr Ala
                85                  90                  95

Asp Thr Ser Ser Asn Thr Ala Tyr Leu Gln Leu Ser Ser Leu Thr Ser
                100                 105                 110

Glu Asp Thr Ala Val Tyr Tyr Cys Thr Tyr Ala Met Glu Tyr Trp Gly
            115                 120                 125

Gln Gly Thr Ser Val Thr Val Ser Ser Ala Lys Thr Thr Pro Pro Ser
        130                 135                 140

Val Tyr Pro Leu Ala
145
```

```
<210> SEQ ID NO 3
<211> LENGTH: 8
<212> TYPE: PRT
<213> ORGANISM: Homo sapiens

<400> SEQUENCE: 3

Phe Asn Ile Lys Asp Thr Tyr Val
1               5

<210> SEQ ID NO 4
<211> LENGTH: 14
<212> TYPE: PRT
<213> ORGANISM: Homo sapiens

<400> SEQUENCE: 4

Trp Ile Gly Arg Ile Asp Pro Ala Asn Gly Leu Thr Thr Phe
1               5                   10

<210> SEQ ID NO 5
<211> LENGTH: 6
<212> TYPE: PRT
<213> ORGANISM: Homo sapiens

<400> SEQUENCE: 5

Thr Tyr Ala Met Glu Tyr
1               5

<210> SEQ ID NO 6
<211> LENGTH: 428
<212> TYPE: DNA
<213> ORGANISM: Homo sapiens

<400> SEQUENCE: 6
ggaccaaagt tcaaagacaa aatggatttt caagtgcaga ttttcagctt cctgctaatc      60
agtgcctcag tcatgctgtc cagaggacaa attgttctca cccagtctcc agcaatcatg     120
tctgcatctc caggggagag ggtcaccatg acctgcagtg ccaggtcaga tgtaagttac     180
atgtattggt atcagcagaa gccaggatcc tcccccagac tcctgattta tgacacatcc     240
aacctggctt ctggagtccc tgttcgcttc agtgccagtg gtctgggac ctcttactct      300 ctcacaatca gccgaatgga ggctgaagat gctgccactt attactgcca gcagtggagt     360
agttacccac cgtggacgtt cggtggaggc accaagctgg aaatcaaacg ggctgatgct     420
gcaccaac                                                              428

<210> SEQ ID NO 7
<211> LENGTH: 142
<212> TYPE: PRT
<213> ORGANISM: Homo sapiens

<400> SEQUENCE: 7

Gly Pro Lys Phe Lys Asp Lys Met Asp Phe Gln Val Gln Ile Phe Ser
1               5                   10                  15

Phe Leu Leu Ile Ser Ala Ser Val Met Leu Ser Arg Gly Gln Ile Val
                20                  25                  30

Leu Thr Gln Ser Pro Ala Ile Met Ser Ala Ser Pro Gly Glu Arg Val
            35                  40                  45

Thr Met Thr Cys Ser Ala Arg Ser Asp Val Ser Tyr Met Tyr Trp Tyr
        50                  55                  60

Gln Gln Lys Pro Gly Ser Ser Pro Arg Leu Leu Ile Tyr Asp Thr Ser
65                  70                  75                  80
```

```
Asn Leu Ala Ser Gly Val Pro Val Arg Phe Ser Ala Ser Gly Ser Gly
                85                  90                  95

Thr Ser Tyr Ser Leu Thr Ile Ser Arg Met Glu Ala Glu Asp Ala Ala
            100                 105                 110

Thr Tyr Tyr Cys Gln Gln Trp Ser Ser Tyr Pro Pro Trp Thr Phe Gly
        115                 120                 125

Gly Gly Thr Lys Leu Glu Ile Lys Arg Ala Asp Ala Ala Pro
    130                 135                 140
```

<210> SEQ ID NO 8
<211> LENGTH: 8
<212> TYPE: PRT
<213> ORGANISM: Homo sapiens

<400> SEQUENCE: 8

```
Arg Ser Asp Val Ser Tyr Met Tyr
1               5
```

<210> SEQ ID NO 9
<211> LENGTH: 11
<212> TYPE: PRT
<213> ORGANISM: Homo sapiens

<400> SEQUENCE: 9

```
Leu Leu Ile Tyr Asp Thr Ser Asn Leu Ala Ser
1               5                   10
```

<210> SEQ ID NO 10
<211> LENGTH: 9
<212> TYPE: PRT
<213> ORGANISM: Homo sapiens

<400> SEQUENCE: 10

```
Gln Gln Trp Ser Ser Tyr Pro Pro Trp
1               5
```

<210> SEQ ID NO 11
<211> LENGTH: 431
<212> TYPE: DNA
<213> ORGANISM: Homo sapiens

<400> SEQUENCE: 11

```
gcccaagtct tagacatcat ggattggctg tggaacttgc tattcctgat ggcagctgcc    60
caaagtgccc aagcacagat ccagttggtg cagtctggac ctgagctgaa gaagcctgga   120
gagacagtca agatctcctg caaggcttct gggtatacct tcacaaactt tgaaatgaac   180
tgggtgaagc aggctccagg acagggttta aactggatgg ctgtataaaa cacctacact   240
ggagacccaa tatatgctga tgacttcagg ggacggtttg ccttctcttt ggaaacctct   300
gccagcactg cctatttgca gatcaacaac ctcaaaaatg aggacatggc tacatatttc   360
tgttcaagag agggagggg ggactactgg ggccagggca ccactctcac ggtctcctca   420
gccaaaacga c                                                       431
```

<210> SEQ ID NO 12
<211> LENGTH: 143
<212> TYPE: PRT
<213> ORGANISM: Homo sapiens

<400> SEQUENCE: 12

```
Ala Gln Val Leu Asp Ile Met Asp Trp Leu Trp Asn Leu Leu Phe Leu
1               5                   10                  15
```

Met Ala Ala Ala Gln Ser Ala Gln Ala Gln Ile Gln Leu Val Gln Ser
                20                  25                  30
Gly Pro Glu Leu Lys Lys Pro Gly Glu Thr Val Lys Ile Ser Cys Lys
            35                  40                  45
Ala Ser Gly Tyr Thr Phe Thr Asn Phe Glu Met Asn Trp Val Lys Gln
        50                  55                  60
Ala Pro Gly Gln Gly Leu Asn Trp Met Gly Cys Ile Asn Thr Tyr Thr
65                  70                  75                  80
Gly Asp Pro Ile Tyr Ala Asp Asp Phe Arg Gly Arg Phe Ala Phe Ser
                85                  90                  95
Leu Glu Thr Ser Ala Ser Thr Ala Tyr Leu Gln Ile Asn Asn Leu Lys
            100                 105                 110
Asn Glu Asp Met Ala Thr Tyr Phe Cys Ser Arg Glu Gly Gly Gly Asp
        115                 120                 125
Tyr Trp Gly Gln Gly Thr Thr Leu Thr Val Ser Ser Ala Lys Thr
130                 135                 140

<210> SEQ ID NO 13
<211> LENGTH: 10
<212> TYPE: PRT
<213> ORGANISM: Homo sapiens

<400> SEQUENCE: 13

Gly Tyr Thr Phe Thr Asn Phe Glu Met Asn
1               5                   10

<210> SEQ ID NO 14
<211> LENGTH: 17
<212> TYPE: PRT
<213> ORGANISM: Homo sapiens

<400> SEQUENCE: 14

Cys Ile Asn Thr Tyr Thr Gly Asp Pro Ile Tyr Ala Asp Asp Phe Arg
1               5                   10                  15
Gly

<210> SEQ ID NO 15
<211> LENGTH: 6
<212> TYPE: PRT
<213> ORGANISM: Homo sapiens

<400> SEQUENCE: 15

Glu Gly Gly Gly Asp Tyr
1               5

<210> SEQ ID NO 16
<211> LENGTH: 432
<212> TYPE: DNA
<213> ORGANISM: Homo sapiens

<400> SEQUENCE: 16
ggaaatacat caggcaggca agggcatcaa gatgaagtca cagacccagg tcttcgtatt      60
tctactgctc tgtgtgtctg gtgctcatgg gagtattgtg atgacccaga ctcccaaatt     120
cctgcttgta tcagcaggag acagggttac cataacctgc aaggccagtc agagtgtgac     180
taatgatgta gcttggtacc aacagaaagcc agggcagtct cctagattgc tgatatacca     240
tgcatccaat cgctacactg gagtccctga gcgcttcact ggcagtggat atgggacgga     300
tttcactttc accatcaaca ctgtgcaggc tgaagacctg gcagtttatt tctgtcagca     360

```
ggattatagc tctcctcgga cgttcggtgg aggcaccaag ctggaaatca aacgggctga    420
tgctgcacca ac                                                        432
```

<210> SEQ ID NO 17
<211> LENGTH: 143
<212> TYPE: PRT
<213> ORGANISM: Homo sapiens

<400> SEQUENCE: 17

Glu Ile His Gln Ala Gly Lys Gly Ile Lys Met Lys Ser Gln Thr Gln
1               5                   10                  15

Val Phe Val Phe Leu Leu Leu Cys Val Ser Ala Gly Ala His Gly Ser Ile
            20                  25                  30

Val Met Thr Gln Thr Pro Lys Phe Leu Leu Val Ser Ala Gly Asp Arg
        35                  40                  45

Val Thr Ile Thr Cys Lys Ala Ser Gln Ser Val Thr Asn Asp Val Ala
    50                  55                  60

Trp Tyr Gln Gln Lys Pro Gly Gln Ser Pro Arg Leu Leu Ile Tyr His
65                  70                  75                  80

Ala Ser Asn Arg Tyr Thr Gly Val Pro Glu Arg Phe Thr Gly Ser Gly
                85                  90                  95

Tyr Gly Thr Asp Phe Thr Phe Thr Ile Asn Thr Val Gln Ala Glu Asp
            100                 105                 110

Leu Ala Val Tyr Phe Cys Gln Gln Asp Tyr Ser Ser Pro Arg Thr Phe
        115                 120                 125

Gly Gly Gly Thr Lys Leu Glu Ile Lys Arg Ala Asp Ala Ala Pro
    130                 135                 140

<210> SEQ ID NO 18
<211> LENGTH: 11
<212> TYPE: PRT
<213> ORGANISM: Homo sapiens

<400> SEQUENCE: 18

Lys Ala Ser Gln Ser Val Thr Asn Asp Val Ala
1               5                   10

<210> SEQ ID NO 19
<211> LENGTH: 7
<212> TYPE: PRT
<213> ORGANISM: Homo sapiens

<400> SEQUENCE: 19

His Ala Ser Asn Arg Tyr Thr
1               5

<210> SEQ ID NO 20
<211> LENGTH: 9
<212> TYPE: PRT
<213> ORGANISM: Homo sapiens

<400> SEQUENCE: 20

Gln Gln Asp Tyr Ser Ser Pro Arg Thr
1               5

<210> SEQ ID NO 21
<211> LENGTH: 4
<212> TYPE: PRT
<213> ORGANISM: Homo sapiens

<400> SEQUENCE: 21

Pro Leu Pro Trp
1

<210> SEQ ID NO 22
<211> LENGTH: 4
<212> TYPE: PRT
<213> ORGANISM: Homo sapiens

<400> SEQUENCE: 22

Val Leu Asp Arg
1

<210> SEQ ID NO 23
<211> LENGTH: 5
<212> TYPE: PRT
<213> ORGANISM: Homo sapiens

<400> SEQUENCE: 23

Asn Arg Arg Thr His
1               5

<210> SEQ ID NO 24
<211> LENGTH: 4
<212> TYPE: PRT
<213> ORGANISM: Homo sapiens

<400> SEQUENCE: 24

Ser Asn Arg Arg
1

<210> SEQ ID NO 25
<211> LENGTH: 783
<212> TYPE: DNA
<213> ORGANISM: Homo sapiens

<400> SEQUENCE: 25
atgcacagct gggagcgcct ggcagttctg gtcctcctag agcggccgc ctgcggtgag      60
gaggcctggg cctgggcggc ccgccccgt ggtcggatcc tgggcggcag agaggccgag     120
gcgcacgcgc ggccctacat ggcgtcggtg cagctgaacg gcgcgcacct gtgcggcggc     180
gtcctggtgg cggagcagtg ggtgctgagc gcggcgcact gcctgaagga cgcggccgac     240
gggaaggtgc aggttctcct gggcgcgcac tccctgtcgc agccggagcc ctccaagcgc     300
ctgtacgacg tgctccgcgc agtgccccac ccggacagcc agcccgacac catcgaccac     360
gacctcctgc tgctacagct gtcggagaag gccacactgg gccctgctgt gcgcccctg     420
ccctggcagc gcgtggaccg cgacgtggca ccgggaactc tctgcgacgt ggccggctgg     480
ggcatagtca accacgcggg ccgccgcccg acagcctgc agcacgtgct cttgccagtg     540
ctggaccgcg ccacctgcaa ccggcgcacg caccacgacg cgccatcac cgagcgcttg     600
atgtgcgcgg agagcaatcg ccgggacagc tgcaagggtg actccggggg cccgctggtg     660
tgcggggcg tgctcgaggg cgtggtcacc tcggctcgc gcgtttgcgg caaccgcaag     720
aagcccggga tctacacccg cgtggcgagc tatgcggcct ggatcgacag cgtcctggcc     780
tag                                                                  783

<210> SEQ ID NO 26
<211> LENGTH: 20
<212> TYPE: DNA
<213> ORGANISM: Homo sapiens

```
<400> SEQUENCE: 26
gtcagggtgc catgcaggag                                           20

<210> SEQ ID NO 27
<211> LENGTH: 21
<212> TYPE: DNA
<213> ORGANISM: Homo sapiens

<400> SEQUENCE: 27
cccaggagaa cctgcacctt c                                         21

<210> SEQ ID NO 28
<211> LENGTH: 20
<212> TYPE: DNA
<213> ORGANISM: Homo sapiens

<400> SEQUENCE: 28
cctcccaccc ttagctatcc                                           20

<210> SEQ ID NO 29
<211> LENGTH: 20
<212> TYPE: DNA
<213> ORGANISM: Homo sapiens

<400> SEQUENCE: 29
acccagactg tgtccctcac                                           20

<210> SEQ ID NO 30
<211> LENGTH: 20
<212> TYPE: DNA
<213> ORGANISM: Homo sapiens

<400> SEQUENCE: 30
cagcgcgtgg accgcgacgt                                           20

<210> SEQ ID NO 31
<211> LENGTH: 20
<212> TYPE: DNA
<213> ORGANISM: Homo sapiens

<400> SEQUENCE: 31
gcgcacagca gggcccagtg                                           20

<210> SEQ ID NO 32
<211> LENGTH: 20
<212> TYPE: DNA
<213> ORGANISM: Homo sapiens

<400> SEQUENCE: 32
ggccgccgcc cggacagcct                                           20

<210> SEQ ID NO 33
<211> LENGTH: 21
<212> TYPE: DNA
<213> ORGANISM: Homo sapiens

<400> SEQUENCE: 33
gccccagccg gccacgtcgc a                                         21

<210> SEQ ID NO 34
<211> LENGTH: 21
<212> TYPE: DNA
```

```
<213> ORGANISM: Homo sapiens

<400> SEQUENCE: 34
gccacctgca accggcgcac g                                              21

<210> SEQ ID NO 35
<211> LENGTH: 23
<212> TYPE: DNA
<213> ORGANISM: Homo sapiens

<400> SEQUENCE: 35
tggcaagagc acgtgctgca ggc                                            23

<210> SEQ ID NO 36
<211> LENGTH: 18
<212> TYPE: DNA
<213> ORGANISM: Homo sapiens

<400> SEQUENCE: 36
ggcccgctgg tgtgcggg                                                  18

<210> SEQ ID NO 37
<211> LENGTH: 21
<212> TYPE: DNA
<213> ORGANISM: Homo sapiens

<400> SEQUENCE: 37
gtcccggcga ttgctctccg c                                              21

<210> SEQ ID NO 38
<211> LENGTH: 20
<212> TYPE: DNA
<213> ORGANISM: Homo sapiens

<400> SEQUENCE: 38
ggccgccgcc cggacagcct                                                20

<210> SEQ ID NO 39
<211> LENGTH: 20
<212> TYPE: DNA
<213> ORGANISM: Homo sapiens

<400> SEQUENCE: 39
gcgcacagca gggcccagtg                                                20

<210> SEQ ID NO 40
<211> LENGTH: 21
<212> TYPE: DNA
<213> ORGANISM: Homo sapiens

<400> SEQUENCE: 40
gccacctgca accggcgcac g                                              21

<210> SEQ ID NO 41
<211> LENGTH: 20
<212> TYPE: DNA
<213> ORGANISM: Homo sapiens

<400> SEQUENCE: 41
gcgcacagca gggcccagtg                                                20

<210> SEQ ID NO 42
<211> LENGTH: 18
```

-continued

```
<212> TYPE: DNA
<213> ORGANISM: Homo sapiens

<400> SEQUENCE: 42
ggcccgctgg tgtgcggg                                                18

<210> SEQ ID NO 43
<211> LENGTH: 20
<212> TYPE: DNA
<213> ORGANISM: Homo sapiens

<400> SEQUENCE: 43
gcgcacagca gggcccagtg                                              20

<210> SEQ ID NO 44
<211> LENGTH: 21
<212> TYPE: DNA
<213> ORGANISM: Homo sapiens

<400> SEQUENCE: 44
gccacctgca accggcgcac g                                            21

<210> SEQ ID NO 45
<211> LENGTH: 21
<212> TYPE: DNA
<213> ORGANISM: Homo sapiens

<400> SEQUENCE: 45
gccccagccg gccacgtcgc a                                            21

<210> SEQ ID NO 46
<211> LENGTH: 18
<212> TYPE: DNA
<213> ORGANISM: Homo sapiens

<400> SEQUENCE: 46
ggcccgctgg tgtgcggg                                                18

<210> SEQ ID NO 47
<211> LENGTH: 21
<212> TYPE: DNA
<213> ORGANISM: Homo sapiens

<400> SEQUENCE: 47
gtcccggcga ttgctctccg c                                            21

<210> SEQ ID NO 48
<211> LENGTH: 23
<212> TYPE: DNA
<213> ORGANISM: Homo sapiens

<400> SEQUENCE: 48
tgctgtgcgc gccctgccct ggc                                          23

<210> SEQ ID NO 49
<211> LENGTH: 22
<212> TYPE: DNA
<213> ORGANISM: Homo sapiens

<400> SEQUENCE: 49
gggcccagtg tggccttctc cg                                           22

<210> SEQ ID NO 50
```

-continued

```
<211> LENGTH: 24
<212> TYPE: DNA
<213> ORGANISM: Homo sapiens

<400> SEQUENCE: 50
tgtgcgcccc gccccctggc agcg                                              24

<210> SEQ ID NO 51
<211> LENGTH: 18
<212> TYPE: DNA
<213> ORGANISM: Homo sapiens

<400> SEQUENCE: 51
gcagggccca gtgtggcc                                                     18

<210> SEQ ID NO 52
<211> LENGTH: 23
<212> TYPE: DNA
<213> ORGANISM: Homo sapiens

<400> SEQUENCE: 52 gcgcccctg gcctggcagc gcg                                                23

<210> SEQ ID NO 53
<211> LENGTH: 27
<212> TYPE: DNA
<213> ORGANISM: Homo sapiens

<400> SEQUENCE: 53
acagcagggc ccagtgtggc cttctcc                                           27

<210> SEQ ID NO 54
<211> LENGTH: 23
<212> TYPE: DNA
<213> ORGANISM: Homo sapiens

<400> SEQUENCE: 54 cccctgccc gcccagcgcg tgg                                                23

<210> SEQ ID NO 55
<211> LENGTH: 18
<212> TYPE: DNA
<213> ORGANISM: Homo sapiens

<400> SEQUENCE: 55
cgcacagcag ggcccagt                                                     18

<210> SEQ ID NO 56
<211> LENGTH: 23
<212> TYPE: DNA
<213> ORGANISM: Homo sapiens

<400> SEQUENCE: 56
gctcttgcca gccctggacc gcg                                               23

<210> SEQ ID NO 57
<211> LENGTH: 18
<212> TYPE: DNA
<213> ORGANISM: Homo sapiens

<400> SEQUENCE: 57
acgtgctgca ggctgtcc                                                     18
```

```
<210> SEQ ID NO 58
<211> LENGTH: 25
<212> TYPE: DNA
<213> ORGANISM: Homo sapiens

<400> SEQUENCE: 58
cttgccagtg gccgaccgcg ccacc                                    25

<210> SEQ ID NO 59
<211> LENGTH: 18
<212> TYPE: DNA
<213> ORGANISM: Homo sapiens

<400> SEQUENCE: 59
agcacgtgct gcaggctg                                            18

<210> SEQ ID NO 60
<211> LENGTH: 23
<212> TYPE: DNA
<213> ORGANISM: Homo sapiens

<400> SEQUENCE: 60
gccagtgctg gcccgcgcca cct                                      23

<210> SEQ ID NO 61
<211> LENGTH: 23
<212> TYPE: DNA
<213> ORGANISM: Homo sapiens

<400> SEQUENCE: 61
aagagcacgt gctgcaggct gtc                                      23

<210> SEQ ID NO 62
<211> LENGTH: 25
<212> TYPE: DNA
<213> ORGANISM: Homo sapiens

<400> SEQUENCE: 62
agtgctggac gccgccacct gcaac                                    25

<210> SEQ ID NO 63
<211> LENGTH: 18
<212> TYPE: DNA
<213> ORGANISM: Homo sapiens

<400> SEQUENCE: 63
ggcaagagca cgtgctgc                                            18

<210> SEQ ID NO 64
<211> LENGTH: 24
<212> TYPE: DNA
<213> ORGANISM: Homo sapiens

<400> SEQUENCE: 64
gccgcccagc gcgtggaccg cgac                                     24

<210> SEQ ID NO 65
<211> LENGTH: 24
<212> TYPE: DNA
<213> ORGANISM: Homo sapiens

<400> SEQUENCE: 65
ggcggcgcgc acagcagggc ccag                                     24
```

```
<210> SEQ ID NO 66
<211> LENGTH: 24
<212> TYPE: DNA
<213> ORGANISM: Homo sapiens

<400> SEQUENCE: 66
gccgccgcca cctgcaaccg gcgc                                          24

<210> SEQ ID NO 67
<211> LENGTH: 25
<212> TYPE: DNA
<213> ORGANISM: Homo sapiens

<400> SEQUENCE: 67
ggcggctggc aagagcacgt gctgc                                         25

<210> SEQ ID NO 68
<211> LENGTH: 23
<212> TYPE: DNA
<213> ORGANISM: Homo sapiens

<400> SEQUENCE: 68
cctgcgcacg taccacgacg gcg                                           23

<210> SEQ ID NO 69
<211> LENGTH: 21
<212> TYPE: DNA
<213> ORGANISM: Homo sapiens

<400> SEQUENCE: 69
ttgcaggtgg cgcggtccag c                                             21

<210> SEQ ID NO 70
<211> LENGTH: 23
<212> TYPE: DNA
<213> ORGANISM: Homo sapiens

<400> SEQUENCE: 70
caccgagcgc atgatgtgcg cgg                                           23

<210> SEQ ID NO 71
<211> LENGTH: 18
<212> TYPE: DNA
<213> ORGANISM: Homo sapiens

<400> SEQUENCE: 71
atggcgccgt cgtggtac                                                 18

<210> SEQ ID NO 72
<211> LENGTH: 23
<212> TYPE: DNA
<213> ORGANISM: Homo sapiens

<400> SEQUENCE: 72
gaggtgaagc tggtggagac agg                                           23

<210> SEQ ID NO 73
<211> LENGTH: 17
<212> TYPE: DNA
<213> ORGANISM: Homo sapiens

<400> SEQUENCE: 73
ggggccagtg gatagac                                                  17
```

```
<210> SEQ ID NO 74
<211> LENGTH: 32
<212> TYPE: DNA
<213> ORGANISM: Homo sapiens

<400> SEQUENCE: 74
ccagttccga gctccagatg acccagactc ca                                32

<210> SEQ ID NO 75
<211> LENGTH: 32
<212> TYPE: DNA
<213> ORGANISM: Homo sapiens

<400> SEQUENCE: 75
ccagttccga gctcgtgctc acccagtctc ca                                32

<210> SEQ ID NO 76
<211> LENGTH: 32
<212> TYPE: DNA
<213> ORGANISM: Homo sapiens

<400> SEQUENCE: 76
ccagttccga gctccagatg acccagtctc ca                                32

<210> SEQ ID NO 77
<211> LENGTH: 32
<212> TYPE: DNA
<213> ORGANISM: Homo sapiens

<400> SEQUENCE: 77
ccagttccga gctcgtgatg acacagtctc ca                                32

<210> SEQ ID NO 78
<211> LENGTH: 17
<212> TYPE: DNA
<213> ORGANISM: Homo sapiens

<400> SEQUENCE: 78
gttggtgcag catcagc                                                 17
```